US008507539B2

(12) United States Patent
Harvey et al.

(10) Patent No.: US 8,507,539 B2
(45) Date of Patent: Aug. 13, 2013

(54) POTASSIUM CHANNEL BLOCKERS AND USES THEREOF

(75) Inventors: Andrew John Harvey, Goodwood (AU); Bernard Luke Flynn, Vermont (AU); Jorgen Alvar Mould, Semaphore (AU); Dharam Paul, Torrensville (AU); Gurmit Singh Gill, Craigieburn (AU); Justin Anthony Ripper, Cumberland Park (AU); Rachel Christine Cooke, Morphett Vale (AU); Julia Stephanie Crossman, South Plympton (AU); Jonathan Bayldon Baell, Ivanhoe (AU); Nathan Wayne Kuchel, Clarence Park (AU); Rajinder Singh, Torrensville (AU)

(73) Assignee: Bionomics Limited, Thebarton, South Austrialia (AU)

( * ) Notice: Subject to any disclaimer, the term of this patent is extended or adjusted under 35 U.S.C. 154(b) by 283 days.

(21) Appl. No.: 12/997,864

(22) PCT Filed: Jun. 12, 2009

(86) PCT No.: PCT/AU2009/000739
§ 371 (c)(1), (2), (4) Date: Mar. 18, 2011

(87) PCT Pub. No.: WO2009/149508
PCT Pub. Date: Dec. 17, 2009

(65) Prior Publication Data
US 2011/0166130 A1 Jul. 7, 2011

Related U.S. Application Data

(60) Provisional application No. 61/061,497, filed on Jun. 13, 2008.

(51) Int. Cl.
*A61K 31/423* (2006.01)
*C07D 263/54* (2006.01)

(52) U.S. Cl.
USPC .......................................... 514/375; 548/217

(58) Field of Classification Search
USPC .......................................... 548/217; 514/375
See application file for complete search history.

(56) References Cited

U.S. PATENT DOCUMENTS

| | | | |
|---|---|---|---|
| 3,250,767 A | | 5/1966 | Bencze |
| 4,420,486 A | * | 12/1983 | Ohyama et al. ............... 514/375 |
| 5,126,351 A | | 6/1992 | Luzzio et al. |
| 5,494,895 A | | 2/1996 | Garcia et al. |
| 6,051,590 A | | 4/2000 | Boa et al. |
| 6,077,680 A | | 6/2000 | Kem et al. |
| 2004/0224936 A1 | | 11/2004 | Chiba et al. |
| 2006/0079535 A1 | | 4/2006 | Wulff et al. |

FOREIGN PATENT DOCUMENTS

| | | |
|---|---|---|
| EP | 0 338 937 B1 | 12/1993 |
| JP | 51095033 | 8/1976 |
| JP | 10-316853 | 12/1998 |
| JP | 10316617 | 12/1998 |
| JP | 10316853 | 12/1998 |
| WO | WO 97/16437 A1 | 5/1997 |
| WO | WO 97/16438 A1 | 5/1997 |
| WO | WO 03/076407 A1 | 9/2003 |
| WO | WO 03/076424 A1 | 9/2003 |
| WO | WO 2008/040057 A1 | 4/2008 |

OTHER PUBLICATIONS

Baell, J. et al. 2004 "Khellinone Derivatives as Blockers of Voltage-Gated Potassium Channel Kv1.3: Synthesis and Immunosuppressive Activity." *J. Med. Chem.* 47(9):2326-2336.
Bencze, W.L. 1966 "1,1,2-Triaryl ethanes, ethenes and ethanols" *CAPLUS*, copyright 2011, Abstract of U.S. Patent No. 3,250,767, pp. 1-2.
Diabetes, 2011, http://www.diabetes.org/diabetes-basics/prevention/.
Ion Channel, 2011 "Ion Channels as Drug Targets" http://www.icagen.com/technology/ionchannels.html.
Whitelaw, M. L. et al. 1991 "Synthesis and sensory evaluation of ring-substituted dihydrochalcone sweeteners." *Journal of Agricultural and Food Chemistry* 39(1):44-51.
Aiyar, J. et al. 1996 "The Signature Sequence of Voltage-gated Potassium Channels Projects into the External Vestibule" *The Journal of Biological Chemistry* 271: 31013-31016.
Basabe, Pilar et al. 2008 "Synthesis of isoprenyl flavonoids: (+)-denticulaflavonol, Macarangin, and Isomacarangin" *SYNLRTT* 8: 1149-1152.
Beeton, C. et al. 2001 "Selective blockade of T lymphocyte $K^+$ channels ameliorates experimental autoimmune encephalomyelitis, a model for multiple sclerosis" *PNAS* 98: 13942-13947.
Beeton, C. et al. 2005 "Targeting Effector Memory T Cells with a Selective Peptide Inhibitor of Kv1.3 Channels for Therapy of Autoimmune Diseases" *Molecular Pharmacology* 67: 1369-1381.
Bhaskar A. & Seshadri, T.R. 1974 "Syntheses of Pashanone & Its Isomers & Their Derivatives" *Indian Journal of Chemistry* 12: 557-560.
Cahalan, M. D. et al. 1985 "A Voltage-Gated Potassium Channel in Human T Lymphocytes" *J. Physiol.* 358: 197-237.
Cahalan, M. D. & Chandy, K.G. 1997 "Ion channels in the immune system as targets for immunosuppression" *Current Opinion in Biotechnology* 8: 749-756.

(Continued)

Primary Examiner — Kamal Saeed
Assistant Examiner — Janet L Coppins
(74) Attorney, Agent, or Firm — Knobbe, Martens, Olson & Bear, LLP

(57) ABSTRACT

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

22 Claims, No Drawings

(56) References Cited

OTHER PUBLICATIONS

Elix, J. A. et al. 1998 "Synthesis of New Lichen Tridepsides" *Australian Journal of Chemistry* 51: 1045-1052.
Fanger, C.M. et al. 1999 "Calmodulin Mediates Calcium-dependent Activation of the Intermediate Conductance $K_{Ca}$ Channel, *IKCa1*" *The Journal of Biological Chemistry* 274: 5746-5754.
Fuchs, P. et al. 2002 "A Thermotropic Mesophase Comprised of Closed Micellar Aggregates of the Normal Type" *Angew. Chem. Int. Ed.* 41: 628-631.
Ghanshani, S. et al. 1998 "Human Calcium-Activated Potassium Channel Gene *KCNN4* Maps to Chromosome 19q13.2 in the REgion Deleted in Diamond-Blackfan Anemia" *Genomics* 51: 160-161.
Grissmer, S. et al. 1990 "Expression and chromosomal localization of a lymphocyte $K^+$ channel gene" *Proc. Natl. Acad. Sci. USA* 87: 9411-9415.
Grissmer, S. et al. 1993 "Calcium-activated Potassium Channels in Resting and Activated Human T Lymphocytes *Expression Levels, Calcium Dependence, Ion Selectivity, and Pharmacology*" *The Journal of General Physiology* 102: 601-630.
Gunzinger, J. & Tabacchi, R. 1985 "Synthesis of a New Depsidone, Derivative of Furfuric Acid: Methyl 3,8-Dimethoxy-9-(2,4-dimethoxy-5-methoxycarbonyl-3,6-dimethylbenzyl)-1,4,6-trimethy-11-oxo-11H dibenzo[b,e][ 1,4Idioxepin-7-carboxylate" *Helvetica Chimica Acta* 68: 1940-1947.
Hatakeda, K. et al. 1977 "Synthesis of 2-Alkoxy-3, 4, 6-trihydroxyacetophenones" *Bulletin of the Chemical Society of Japan* 50: 1649-1650.
Horie, T. et al. 1983 "Studies of the Selective *O*-Alkylation and Dealkylation of Flavonoids. VI. Demethylation of 8-Hydroxy-5,7-dimethoxyflavones with Anhydrous Aluminum Chloride or Bromide in Acetonitrile" *The Chemical Society of Japan* 56: 3773-3780.
Joiner, W.J. et al. 1997 "hSK4, a member of a novel subfamily of calcium-activated potassium channels" *Proc. Natl. Acad. Sci USA* 94: 11013-11018.
Khanna, R. et al. 1999 "hSK4/hIK1, a Calmodulin-binding $K_{Ca}$ Channel in Human T Lymphocytes *Roles in Proliferation and Volume Regulation*" *The Journal of Biological Chemistry* 274: 14838-14849.
Logsdon, N.J. et al. 1997 "A Novel Gene, *hKCa4*, Encodes the Calcium-activated Potassium Channel in Human T Lymphocytes" *The Journal of Biological Chemistry* 272: 32723-32726.
Rauer, H. et al. 1999 "Structural Conservation of the Pores of Calcium-activated and Voltage-gated Potassium Channels Determined by a Sea Anemone Toxin" *The Journal of Biological Chemistry* 274: 21885-21892.
Robertson, A. & Williamson, W.R.N. 1957 "Vitexin. Part II. The Synthesis of 3-Acetyl-2-hydroxy-4: 6-dimethoxyphenylacetaldehyde Dimethyl Acetal" *Journal of the Chemical Society* 5018-5019.
Schmalhofer, W.A. et al. 2002 "Identification of a New Class of Inhibitor of the Voltage-Gated Potassium Channel, Kv1.3, with Immunosuppressant Properties" *Biochemistry* 41: 7781-7794.
Schmalhofer, W.A. et al. 2003 "Di-Substituted Cyclohexyl Derivatives Bind to two Identical Sites with Positive Cooperativity on the Voltage-Gated Potassium Channel, Kv1.3" *Biochemistry* 42: 4733-4743.
Schmitz, A. et al. 2005 "Design of PAP-1, a Selective Small Molecule Kv1.3 Blocker, for the Suppression of Effector Memory T Cells in Autoimmune Diseases" *Molecular Pharmacology* 68: 1254-1270.
Vandorpe. D.H. et al. 1998 "cDNA Cloning and Functional Characterization of the Mouse $Ca^{2+}$-gated $K^+$ Channel, mIK1" *The Journal of Biological Chemistry* 273: 21542-21553.
Vennekamp, J. et al. 2004 "Kv1.3-Blocking 5-Phenylalkoxypsoralens: A New Class of Immunomodulators" *Molecular Pharmacology* 65: 1364-1374.
Verheugen, J.A.H. et al. 1995 "Voltage-gated and $Ca^{2+}$-activated $K^+$ channels in Intact Human T lymphocytes; Noninvasive Measurements of Membrane Current, Membrane Potential, and Intracellular Calcium" *J. Gen. Physiol.* 105: 765-794.
Whitelaw, M.L. et al. 1991 "Synthesis and sensory evaluation of ring-substituted dihydrochalcone sweeteners. 2. Analogues of 3'-carboxyhesperetin dihydrochalcone, a high-potency dihydrochalcone sweetener" *J Agric Chem* 39: 663-667.
Wulff, H. et al. 2003 "Potassium channels as therapeutic targets for autoimmune disorders" *Current Opinion in Drug Discovery & Development* 6: 640-647.
Wulff, H. et al. 2003 "The voltage-gated Kv1.3 K+ channel in effector memory T cells as new target for MS" *The Journal of Clinical Investigation* 111: 1703-1713. (Erratum attached).
Xu, Jianchao et al. 2004 "The voltage-gated potassium channel Kv1.3 regulates peripheral insulin sensitivity" *PNAS* 101: 3112-3117.
Cianci, J. et al. 2008 Synthesis and biological evaluation of chalcones as inhibitors of the voltage-gated potassium channel Kv1.3. *Bioorg. & Med. Chem. Lett.* 18:2055-2061.
Harvey, A.J. et al. 2006 "A new class of Blockers of the Voltage-Gated Potassium Channel Kv1.3 via Modification of the 4- or 7-Position of Khellinone" *J. Med. Chem.* 49:1433-1441.
Satuluri, V.S.A.K. et al. 2008 "A Quantitative Structure-Activity Relationship Study on Some Series of Potassium Channel Blockers" *Med. Chem.* 5(1):87-92.
Wulff, H. et al. 2007 "Targeting effector memory T-cells with Kv1.3 blockers" *Current Opinion in Drug Discovery & Development* 10(4):438-445.

* cited by examiner

POTASSIUM CHANNEL BLOCKERS AND USES THEREOF

RELATED APPLICATIONS

This application is a U.S. National Phase of International Application No.: PCT/AU2009/000739, filed Jun. 12, 2009, designating the U.S. and published in English on Dec. 17, 2009 as WO 2009/149508 A1, which claims the benefit of U.S. Provisional Application No. 61/061,497, filed Jun. 13, 2008.

FIELD OF THE INVENTION

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

BACKGROUND

Many autoimmune and chronic inflammatory diseases are related to immunoregulatory abnormalities. Diseases such as systemic lupus erythematosis, type I diabetes mellitus, chronic rheumatoid arthritis, multiple sclerosis and psoriasis have in common the appearance of autoantibodies and self-reactive lymphocytes.

Multiple sclerosis is the most common neurological disease of young people. It is believed to cost more in medical care and lost income than any other neurological disease of young adults.

Multiple sclerosis affects the myelin sheaths of nerves. Myelin is an insulating material that coats most axons and allows rapid signal conduction over long distances by saltatory conduction. It is thought that antibodies and specialised cells of the immune system attack the myelin coating. This process leads to inflammation and scarring (sclerosis) which damages blood vessels in the area by the formation of a lesion known as a plaque. These plaques are characterised by being infiltrated by macrophages and T cells. This results in demyelination with the consequential loss of the rapid signal conduction.

A possible method of treating these autoimmune and inflammatory diseases is by suppressing T-cell proliferation and modulating their activation.

The early stages of T-cell activation may be conceptually separated into pre-$Ca^{2+}$ and post-$Ca^{2+}$ events (Cahalan and Chandy 1997, *Curr. Opin. Biotechnol.* 8 749). Following engagement of the T-cell receptor by an antigen, activation of tyrosine kinases and the generation of inositol 1,4,5-triphosphate lead to the influx of $Ca^{2+}$ and a rise in the cytoplasmic $Ca^{2+}$ concentration. The rise in $Ca^{2+}$ activates the phosphatase calcineurin, which then dephosphorylates a cytoplasmically localized transcription factor (N-FAT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{2+}$ signals while others require only a transient rise of $Ca^{2+}$ Ion channels underlie the $Ca^{2+}$ signal of T-lymphocytes. $Ca^{2+}$ ions move across the plasma membrane through a channel termed the store-operated $Ca^{2+}$ channel or the calcium release-activated $Ca^{2+}$ channel. Two distinct types of potassium channels indirectly determine the driving force of calcium entry. The first is the voltage-gated Kv1.3 channel (Cahalan 1985, *J. Physiol.* 385: 197; Grissmer 1990, *Proc. Natl. Acad. Sci. USA* 87 9411; Verheugen 1995, *J. Gen. Physiol.* 105 765; Aiyar 1996, *J. Biol. Chem.* 271 31013; Cahalan and Chandy 1997, *Curr. Opin. Biotechnol.* 8 749) and the second is the intermediate-conductance calcium-activated potassium channel, IKCa1 (Grissmer 1993, *J. Gen. Physiol.* 102 601; Fanger 1999 *J. Biol. Chem.* 274 5746; Rauer 1999, *J. Biol. Chem.* 274 21885; VanDorpe 1998, *J. Biol. Chem.* 273 21542; Joiner 1997, *Proc. Natl. Acad. Sci. USA* 94 11013; Khanna 1999, *J. Biol. Chem.* 274 14838; Lodgson 1997, *J. Biol. Chem.* 272 32723; Ghanshani 1998, *Genomics* 51 160). When these potassium channels open, the resulting efflux of $K^+$ hyperpolarizes the membrane, which in turn accentuates the entry of $Ca^{2+}$, which is absolutely required for downstream activation events (Cahalan and Chandy 1997, *Curr. Opin. Biotechnol.* 8: 749).

The predominant voltage-gated channel in human T-lymphocytes is encoded by Kv1.3, a Shaker-related gene. Kv1.3 has been characterised extensively at the molecular and physiological level and plays a vital role in controlling T-lymphocyte proliferation, mainly by maintaining the resting membrane potential of resting T-lymphocytes. Inhibition of this channel depolarises the cell membrane sufficiently to decrease the influx of $Ca^{2+}$ and thereby prevents downstream activation events.

Accordingly, compounds which are selective Kv1.3 blockers are potential therapeutic agents as immunosuppressants for the prevention of graft rejection, and the treatment of autoimmune and inflammatory disorders. They could be used alone or in conjunction with other immunosuppressants, such as selective IKCa1 blockers or cyclosporin, in order to achieve synergism and/or to reduce toxicity, especially of cyclosporin.

Developments in the field of voltage-gated K-channel electrophysiology have strengthened the case for treating of multiple sclerosis and also diabetes mellitus by inhibiting the Kv1.3 channel. It was found that autoreactive T-cells from multiple sclerosis patients exhibit highly elevated levels of Kv1.3 (Wulff, H et al (2003) J. Clin Invest. 111 (11) 1703-1713). ShK-K22Dap, a selective peptide blocker of Kv1.3, potently inhibited the proliferation of T-cells with this high-Kv1.3 phenotype. (Beeton, C. et al (2001) PNAS 98 13942-13947). The connection between T-cell replication and Kv1.3 blockade has also been shown through the use of a small molecule, a psoralen derivative, that is an active and relatively specific inhibitor of the Kv1.3 channel. The derivative showed specificity in inhibiting the proliferation of the high Kv1.3 T-cells over peripheral blood T-cells (Vennekamp et al (2004) Mol. Pharm. 65 1364-1374).

The Kv1.3 channel has also been associated with diabetes. Studies of Kv1.3 knockout mice found that the mice have increased insulin sensitivity. The selective inhibition of the Kv1.3 channel also led to increased insulin sensitivity (Xu, J. et al. (2004) *PNAS* 101 (9), 3122-3117). It has been suggested by Wulff that diabetes also involves autoreactive T-cells that express very high levels of Kv1.3 (Wulff, H. et al. (2003) *Curr. Op. DDD.* 6 640-647).

At present there exist a number of non-selective potassium channel blockers that will inhibit lymphocyte proliferation, but have adverse side effects. Other potassium channels exist in a wide range of tissues including the heart and brain, and generally blocking these channels is undesirable. Accordingly it would be advantageous to provide or identify compounds, which are selective inhibitors of the Kv1.3 channel.

U.S. Pat. No. 5,494,895 discloses the use of a thirty-nine amino acid peptide, scorpion peptide margatoxin, as a selective inhibitor and probe of Kv1.3 channels present in human lymphocytes, and also as an immunosuppressant. However the use of this compound is limited by its potent toxicity.

International Patent Application publication No's WO 97/16438 and WO 09/716,437, and U.S. Pat. No. 6,051,590 describe the use of the triterpene, correolide and related compounds as immunosuppressants. The potential for these compounds to become immunosuppressants was illustrated by experiments showing their attenuation of the delayed-type hypersensitivity (DTH) response in mini-swine.

U.S. Pat. No. 6,077,680 describes DNA segments and proteins derived from sea anemone species, more particularly ShK toxin from *Stichodactyla helianthus*. The ShK toxin was found to block Kv1.1, Kv1.3, Kv1.4 and Kv1.6, but a mutant ShK-K22DAP was found to selectively block Kv1.3. However, the mutant did not exhibit the requisite pharmacokinetic profile for clinical use. A recently reported ShK analog, ShK (L5), was at least 100-fold more active against Kv1.3 ($K_d$=69 pM) than Kv1.1 and furthermore it showed at least 250-fold selectivity over every other relevant member of the Kv1 family (Beeton et al. (2005) *Mol. Pharm.* 67, 1369-1381)).

Both ShK toxin and ShK(L5) were shown to both prevent and treat adoptive transfer experimental autoimmune encephalomyelitis in Lewis rats, an animal model for human multiple sclerosis (Beeton, et al. (2001) *Proc. Natl. Acad. Sci. USA* 98 13942; Beeton et al. (2005) *Mol. Pharm.* 67, 1369-1381), by selectively targeting T-cells chronically activated by the myelin antigen, MBP (myelin basic protein). The same study also indicated that chronically activated encephalitogenic rat T cells express a unique channel phenotype characterised by high expression of Kv1.3 channels (approximately 1500 per cell) and low numbers of IKCa1 channels (approximately 120 per cell). This channel phenotype is distinct from that seen in quiescent and acutely activated cells and may be a functionally relevant marker for chronically activated rat T lymphocytes.

Other compounds which are blockers of Kv1.3 include psoralens (Vennekamp et al. (2004) *Mol. Pharm.* 65, 1365-1374 and Wulff et al., US 2006/0079535) and selected benzamides (Schalhofer et al. (2002) *Biochem.* 41, 7781-7794 and Schalhofer et al (2003) *Biochem.* 42, 4733-4743).

Khellinone, a substituted benzofuran and natural product from certain plants, and 8-Methoxypsoralen (8-MOP), both commercially available products, have been found to exhibit blocking activity on the Kv1.3 channel.

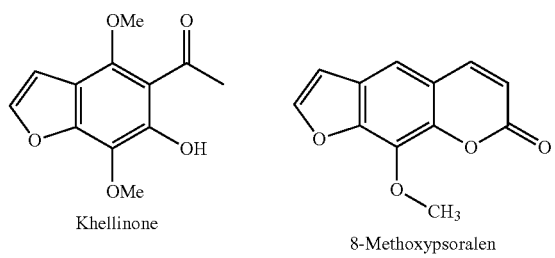 [SMILES: COc1c(C(C)=O)c(O)c(OC)c2occc12 ; COc1c2occc2cc2ccc(=O)oc12]

Khellinone

8-Methoxypsoralen

Khellinone, 8-MOP and four dimeric variants thereof were described in a Poster (abstract. No. 1078) at a meeting of the American Physiological Society in Snowmass, Colo. (*The Physiologist* 42: A12 (1999)). The authors were testing whether linking two active units with a spacer, improved activity. Some of the bivalent derivatives were said to be ineffective, and others were said to block the Kv1.3 channel, but lack therapeutic utility due to their extreme sensitivity to hydrolysis (very poor stability) and high lipophilicity (poor solubility in clinical conditions).

The present invention provides a novel class of compounds which are useful in the treatment of disease states which would benefit from the modulation of potassium channel activity in vivo.

SUMMARY OF THE INVENTION

The invention provides compounds of formula (I) or salts thereof,

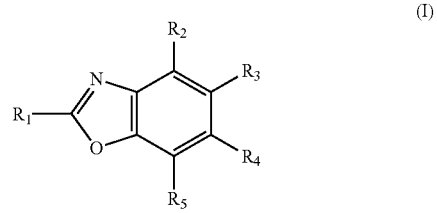

(I)

wherein
$R_1$ is selected from hydrogen, halo, optionally substituted lower alkyl, optionally substituted aryl, optionally substituted heteroaryl, optionally substituted heterocyclyl, optionally substituted $C_{3-7}$ cycloalkyl, —OR, —C(O)R, —C(O)OR, —OC(O)R (where R is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from hydrogen, lower alkyl or aryl);

$R_2$ is selected from halo, cyano, optionally substituted lower alkyl, optionally substituted aryl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from hydrogen, lower alkyl or aryl);

$R_3$ is selected from —C(O)$R_6$, where $R_6$ is selected from lower haloalkyl, optionally substituted alkyl, optionally substituted $C_{3-7}$ cycloalkyl, optionally substituted heterocyclyl, optionally substituted heteroaryl, optionally substituted aryl, —OR, —C(O)R, —C(O)OR, —OC(O)R, SR, (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R'', —NR'C(O)R'' and —NR'R'' (where R' and R'' are independently selected from hydrogen or lower alkyl); —S(O)$_m$R''' (where m is 1 or 2 and R''' is independently selected from NH$_2$, dialkylamino, monoalkylamino, optionally substituted alkyl, optionally substituted $C_{3-7}$ cycloalkyl, optionally substituted heterocyclyl, optionally substituted heteroaryl and optionally substituted aryl); —SR (where and R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); —C(OH)HR (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); optionally substituted heterocyclyl; optionally substituted heteroaryl; NR'R" (where R' and R" are independently selected from hydrogen or lower alkyl); NR'C(O)R" (where R' and R" are independently selected from hydrogen or lower alkyl); and —C(O)NR'R" (where R' and R" are independently selected from hydrogen or lower alkyl);

$R_4$ is $XR_7$, where X is —O—, —S—, —CH$_2$—, —CH=CH—, —C≡C— or NR' (where R' is selected from hydrogen or lower alkyl) and where $R_7$ is selected from optionally substituted alkyl, optionally substituted alkenyl, optionally substituted aryl, optionally substituted heteroaryl, optionally substituted heterocyclyl, optionally substituted alkynyl, optionally substituted $C_{3-7}$ cycloalkyl, optionally substituted $C_{4-7}$ cycloalkenyl, —C(O)R, (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and —C(O)NR'R' (where R' and R" are independently selected from hydrogen or lower alkyl); and $R_5$ is selected from optionally substituted alkyl, optionally substituted aryl, optionally substituted heteroaryl, optionally substituted heterocyclyl, —OR, —C(O)R, —C(O)OR, —OC(O)R, —C(O)NRR', —NRC(O)R', —NRR', SR, SOR, SO$_2$R, and SO$_2$NRR' (where R is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl and R' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In an aspect of the invention there is provided a method for the treatment or prevention of autoimmune or chronic inflammatory diseases, or the prevention of rejection of foreign organ transplants and/or related afflictions, by the administration of a compound of formula I or a pharmaceutically acceptable salt thereof, or a composition containing a compound of formula I or pharmaceutically acceptable salt thereof.

In another aspect the invention provides the use of a compound of formula I or a salt thereof in the manufacture of a medicament for the treatment or prevention of autoimmune or chronic inflammatory diseases, or the prevention of rejection of foreign organ transplants and/or related afflictions.

In another aspect of the invention there is provided a method of intentionally modulating potassium ion channel activity of T-cells by the application of a compound of Formula I, or a pharmaceutically acceptable salt thereof, to said T-cells.

In a further aspect of the invention there is provided a pharmaceutical composition for use as an immunosuppressant, the composition comprising an effective amount of a compound of Formula I or pharmaceutically acceptable salt thereof and optionally a carrier or diluent.

In another aspect of the invention there is provided a process for the preparation of compounds of formula I or salts thereof.

DETAILED DESCRIPTION OF THE INVENTION

The invention is based on the discovery that compounds of the general formula I, as described in the above Summary of the Invention can have useful properties as inhibitors of potassium ion channels, and particularly the Kv1.3 channel. Such compounds have significant potential as immunosuppressants for the treatment of autoimmune disorders such as multiple sclerosis, rheumatoid arthritis, type I diabetes mellitus and psoriasis. They may also be useful in the treatment or prevention of graft rejection and cardiac arrhythmia such as atrial fibrillation (AF).

The term "alkyl" as used alone or in combination herein refers to a straight or branched chain saturated hydrocarbon group. The term "$C_{1-12}$ alkyl" refers to such a group containing from one to twelve carbon atoms and the terms "$C_{1-6}$ alkyl" and "lower alkyl" refer to such groups containing from one to six carbon atoms, such as methyl ("Me"), ethyl ("Et"), n-propyl, isopropyl, n-butyl, isobutyl, sec-butyl, tert-butyl and the like.

The term "alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), propylene isomers (e.g., —CH$_2$CH$_2$CH$_2$— and —CH(CH$_3$)CH$_2$—), butylene isomers (e.g., —CH$_2$CH$_2$—CH(CH$_3$)— and —CH$_2$CH$_2$CH$_2$CH$_2$— and the like.

The term "$C_{3-7}$ cycloalkyl" refers to non-aromatic, saturated non-aromatic carbocycles having from 3 to 7 carbon atoms. Examples include cyclopentyl and cyclohexyl.

The term "cycloalkylene" refers to a divalent cycloalkyl group preferably having from 3 to 7 carbon atoms.

The term "alkenyl" refers to a straight or branched hydrocarbon containing one or more double bonds, preferably one or two double bonds. The term "$C_{2-12}$ alkenyl" refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "alkenylene" refers to divalent alkenyl groups preferably having from 2 to 8 carbon atoms and more preferably 2 to 6 carbon atoms. Examples include ethenylene (—CH=CH—), and the propenylene isomers (e.g., —CH$_2$CH=CH— and —C(CH$_3$)=CH—), and the like.

The term "$C_{4-7}$ cycloalkenyl" refers to non aromatic carbocycles having 4 to 7 carbon atoms and having one or more double bonds. Examples include cyclopentenyl, 1-methylcyclopentenyl, cyclohexenyl, 1,3-cyclopentadienyl, 1,3-cyclohexadienyl and 1,4-cyclohexadienyl.

The term "alkynyl" refers to a straight or branched hydrocarbon containing one or more triple bonds, preferably one or two triple bonds. The term "$C_{2-12}$ alkynyl" refers to such a group containing from two to twelve carbon atoms. Examples include 2-propynyl and 2- or 3-butynyl.

The term "alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The terms "alkenyloxy" and "alkynyloxy" as used alone or in combination respectively refer to an alkenyl and alkynyl group as earlier described linked via an oxygen linkage (—O—).

The term "aromatic" when used alone or in combination refers to monocyclic or bicyclic aryl rings and ring systems (aromatic hydrocarbon rings or ring systems) and also aromatic heterocyclic rings or ring systems, as known as heteroaryl or heteroaromatic rings. Preferred aromatic rings are optionally substituted phenyl ("Ph") rings.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl or benzothienyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

The above heterocycles may be optionally substituted with a broad range of substituents, such as $C_{1-6}$ alkyl, $C_{1-6}$ alkoxy, $C_{2-6}$ alkenyl, $C_{2-6}$ alkynyl, halo, hydroxy, mercapto, trifluoromethyl, phenyl, phenyloxy, phenylalkyl, phenylalkyloxy, amino, cyano or mono or di($C_{1-6}$alkyl)amino.

As referred to above heterocycle or heteroaryl may be fused to a carbocyclic ring such as phenyl, naphthyl, indenyl, azulenyl, fluorenyl, and anthracenyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, cyano, phenyl, phenyloxy, phenylalkyl, phenylalkyloxy, amino and mono or di($C_{1-6}$alkyl) amino.

Examples of some preferred heterocyclic and heteroaromatic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines, quinoxalines, furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1H thieno[2,3-c]pyrazolyl, thieno[2,3-b]furyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl, and cytosinyl. These radicals can be optionally substituted with, by example, $C_{1-6}$alkyl, $C_{1-6}$alkoxy, $C_{2-6}$alkenyl, $C_{2-6}$alkynyl, halo, hydroxy, mercapto, trifluoromethyl, amino, phenyl, phenyloxy, phenylalkyl, phenylalkyloxy, cyano or mono or di($C_{1-6}$alkyl)amino.

Heteroaryl or heteroaromatic rings may preferably be selected from isoxazolyl, oxazolyl, imidazolyl, thiazolyl, thiadiazolyl, isothiazolyl, furazanyl, triazolyl, pyridyl, pyrimidinyl, furyl, pyrazolyl, pyridazinyl, thienyl and aryl fused heteroaromatic rings such as benzfuranyl, benzothiophenyl and benzoisoxazolyl.

Heterocyclyl or heterocyclic rings may preferably be selected from pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

The term "arylalkyl" refers to carbocyclic aromatic rings or ring systems as previously described and substituted by an alkyl group, also as previously described. Unless otherwise indicated the aryl substituent is attached by the alkyl part of the substituent. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "halo alkyl" group has one or more of the hydrogen atoms on an alkyl group replaced with halogens. A notable example is —$CF_3$ and —$CHF_2$.

The term "aryloxy" refers to an aryl group as earlier described linked to the parent structure via an oxygen linkage (—O—). Notable examples include phenoxy and 4-fluorophenoxy. Similarly the term "heteroaryloxy" refers to a heteroaryl group as earlier described linked to the parent structure via an oxygen group. Notable examples include pyrazinyloxy and pyrimidinyloxy.

The term "optionally substituted" means that a group may include one or more substituents. One or more hydrogen atoms on the group may be replaced by substituent groups independently selected from halogen, guanidino, halo $C_{1-3}$ alkyl, $C_{1-6}$ alkyl, $C_{2-6}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$(CH_2)_p$ heteroaryl, —$C_6H_4S(O)_q$ $C_{1-6}$ alkyl, —C(Ph)$_3$, —CN, —OR, —O—$(CH_2)_{1-6}$—R, —O—$(CH_2)_{1-6}$—OR, —OC(O)R, —C(O)R, —C(O)OR, —OC(O)NR'R", —NR'R", —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)', —OS(O)$_2$R, —PO(OR)$_2$ and —NO$_2$;
where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —$CO_2H$, $CF_3$, CN, phenyl, $NH_2$ and —$NO_2$; or when R' and R" are attached to the same nitrogen atom, they may, together with the atom to which they are attached, form a 5 to 7 membered nitrogen containing heterocyclic ring.

In the case of an alkylene divalent group, for instance, the term "optionally substituted" also indicates that one or more saturated carbon atoms may be substituted for a heteroatom or heterogroup, such as O, S, NH and the like. For example an optionally substituted alkylene group could be represented by a group such as —$CH_2CH_2OCH_2$—, —$CH_2$—O—$CH_2$—, —$CH_2CH_2OCH_2CH_2OCH_2CH_2$—, —$CH_2CH_2NH$—$CH_2$—, —$CH_2NHCH_2$—, and the like. Optionally substituted alkylene also includes the situation where the alkylene chain is interrupted by a cycloalkyl moiety such as, for instance,

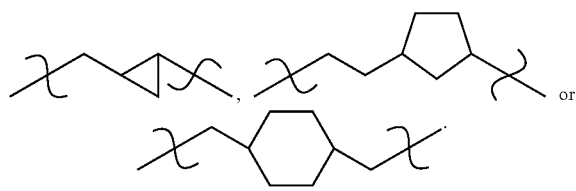

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, cycloalkenyl, aryl, heteroaryl or heterocyclyl group, the group may itself be optionally substituted with one to six of the same or different substituents selected from halogens, $C_{1-6}$ alkyl, $C_{2-6}$ alkenyl, $C_{2-6}$ alkynyl, $C_{1-6}$ haloalkyl (in particular —$CF_3$ and —$CHF_2$), $C_{1-6}$ haloalkoxy (such as —$OCF_3$), —OH, phenyl, benzyl, phenoxy, benzyloxy, benzoyl, —$NH_2$, guanidino, —$NHC_{1-4}$ alkyl, —N($C_{1-4}$ alkyl)$_2$, —CN, —$NO_2$, mercapto, $C_{1-6}$ alkylcarbonyl, $C_{1-6}$ alkoxycarbonyl and $CO_2H$.

The salts of the compound of the present invention are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of the present invention, and the salts thereof, can be presented in the form of pharmaceutically acceptable derivatives. The term "pharmaceutically acceptable derivative" includes pharmaceutically acceptable esters, prodrugs, solvates and hydrates of the compounds of the present invention or salts thereof. Pharmaceutically acceptable derivatives may include any pharmaceutically acceptable hydrate or any other compound or prodrug which, upon administration to a subject, is capable of providing (directly or indirectly) a compound of the present invention or an active metabolite or residue thereof.

The pharmaceutically acceptable salts include acid addition salts, base addition salts, and the salts of quaternary amines (for example, ammonium and guanidinium salts) and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the present invention of salt thereof.

It will be appreciated that the compounds of the present invention and some derivatives thereof may have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

Furthermore, depending on the substitution pattern the compounds of the present invention may be capable of undergoing tautomerism. Accordingly, all possible tautomers of a compound of the present invention fall within the scope and spirit of the invention.

In some preferred embodiments of the invention, and with reference to the general formula I, one or more of the following preferred definitions apply:

a) $R_1$ is selected from hydrogen, lower alkyl, lower halo alkyl, optionally substituted cycloalkyl, optionally substituted aryl, optionally substituted heteroaryl, and lower alkoxy.

b) $R_2$ is selected from optionally substituted lower alkyl, halo, cyano, optionally substituted heteroaryl, and optionally substituted heterocyclyl;

c) $R_3$ is selected from —C(O)—$R_6$ where $R_6$ is lower haloalkyl, optionally substituted alkyl, optionally substituted $C_{3-7}$ cycloalkyl, optionally substituted heterocyclyl, optionally substituted heteroaryl, optionally substituted aryl, or NR'R" (where R' and R" are independently selected from hydrogen, lower alkyl or optionally substituted heteroaryl); —S(O)$_m$R''' (where m is 1 or 2 and where R''' is independently selected from NH$_2$, dialkylamino, monoalkylamino, optionally substituted alkyl, optionally substituted $C_{3-7}$ cycloalkyl, optionally substituted heterocyclyl, optionally substituted heteroaryl and optionally substituted aryl); or —C(OH)HR (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

d) $R_4$ is OR$_7$ where R$_7$ is selected from optionally substituted alkyl, optionally substituted alkenyl, optionally substituted aryl, optionally substituted heteroaryl, optionally substituted heterocyclyl, optionally substituted alkynyl, optionally substituted $C_{3-7}$ cycloalkyl, optionally substituted $C_{4-7}$ cycloalkenyl, —C(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and —C(O)NR'R" (where R' and R" are independently selected from hydrogen or lower alkyl). Preferably $R_4$ is selected from a terminally substituted $C_{1-10}$ alkoxy, optionally substituted heteroaryloxy, optionally substituted heterocyclyloxy, and optionally substituted cycloalkyloxy; and e) $R_5$ is preferably defined by the group —Y-L-$R_8$ wherein: Y is selected from a single bond, —O—, —C(O)—, —S—, —NR'''—, —C(O)NR''''—, or —NR'''C(O)— (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

L is selected from a divalent linker group of 2-6 atoms in length selected from optionally substituted $C_{2-6}$ alkylene, optionally substituted $C_{3-6}$ cycloalkylene, optionally substituted $C_{2-6}$ alkenylene, and optionally substituted $C_{2-6}$ alkynylene; and $R_8$ is selected from optionally substituted aryl, optionally substituted heterocyclyl, optionally substituted heteroaryl, optionally substituted aryloxy, optionally substituted heterocyclyloxy, optionally substituted heteroaryloxy, —NHR''' (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and SR''' (where is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In an embodiment, the compound of formula (I) is a compound of formula (Ia) or salt thereof

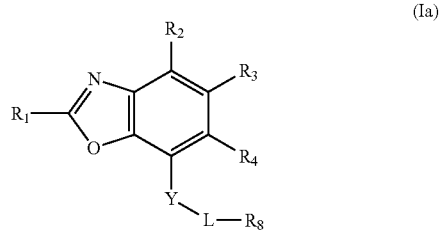

(Ia)

wherein:

$R_1$ is selected from hydrogen, halo, optionally substituted lower alkyl, optionally substituted aryl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from hydrogen, lower alkyl or aryl);

$R_2$ is selected from halo, cyano, optionally substituted lower alkyl, optionally substituted aryl, optionally substituted heteroaryl, optionally substituted heterocyclyl, optionally substituted $C_{3-7}$ cycloalkyl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from hydrogen, lower alkyl or aryl);

$R_3$ is selected from —C(O)R$_6$, where R$_6$ is selected from lower haloalkyl, optionally substituted alkyl, optionally substituted $C_{3-7}$ cycloalkyl, optionally substituted heterocyclyl, optionally substituted heteroaryl, optionally substituted aryl, —OR, —C(O)R, —C(O)OR, —OC(O)R, SR, (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl); —S(O)$_m$R''' (where m is 1 or 2 and R''' is independently selected from NH$_2$, dialkylamino, monoalkylamino, optionally substituted alkyl, optionally substituted $C_{3-7}$ cycloalkyl, optionally substituted heterocyclyl, optionally substituted heteroaryl and optionally substituted aryl); —SR (where and R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); —C(OH)HR (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); optionally substituted heterocyclyl; optionally substituted heteroaryl; NR'R" (where R' and R" are independently selected from hydrogen or lower alkyl); NR'C(O)R" (where R' and R" are independently selected from hydrogen or lower alkyl); and —C(O)NR'R" (where R' and R" are independently selected from hydrogen or lower alkyl);

$R_4$ is $XR_7$, where X is —O—, —S—, —CH$_2$—, —CH=CH—, or NR' (where R' is selected from hydrogen or lower alkyl) and where $R_7$ is selected from optionally substituted alkyl, optionally substituted alkenyl, optionally substituted aryl, optionally substituted heteroaryl, optionally substituted heterocyclyl, optionally substituted alkynyl, optionally substituted $C_{3-7}$ cycloalkyl, optionally substituted $C_{4-7}$ cycloalkenyl, —C(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and —C(O)NR'R" (where R' and R" are independently selected from hydrogen or lower alkyl);

Y is selected from a single bond, —O—, —C(O)—, —S—, —NR'"—, —C(O)NR'"—, or —NR'"C(O)— (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

L is selected from a divalent linker group of 2-6 atoms in length selected from optionally substituted $C_{2-6}$ alkylene, optionally substituted $C_{3-6}$ cycloalkylene, optionally substituted $C_{2-6}$ alkenylene, and optionally substituted $C_{2-6}$ alkynylene; and $R_8$ is selected from optionally substituted aryl, optionally substituted heterocyclyl, optionally substituted heteroaryl, optionally substituted aryloxy, optionally substituted heterocyclyloxy, optionally substituted heteroaryloxy, —NHR'" (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and SR'" (where is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In a preferred embodiment the present invention provides compounds of formula (Ia') or salts thereof,

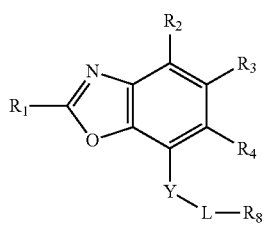

wherein:

$R_1$ is selected from hydrogen, lower alkyl, lower halo alkyl, optionally substituted cycloalkyl, optionally substituted aryl, optionally substituted heteroaryl, and lower alkoxy;

$R_2$ is selected from optionally substituted lower alkyl, halo, cyano, optionally substituted heteroaryl, and optionally substituted heterocyclyl;

$R_3$ is selected from —C(O)—$R_6$ where $R_6$ is lower haloalkyl, optionally substituted alkyl, optionally substituted $C_{3-7}$ cycloalkyl, optionally substituted heterocyclyl, optionally substituted heteroaryl, optionally substituted aryl, or NR'R" (where R' and R" are independently selected from hydrogen, optionally substituted heteroaryl, or lower alkyl); —S(O)$_m$R'" (where m is 1 or 2 and where R'" is independently selected from optionally substituted alkyl, optionally substituted $C_{3-7}$ cycloalkyl, optionally substituted heterocyclyl, optionally substituted heteroaryl and optionally substituted aryl); or —C(OH)HR (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

$R_4$ is a terminally substituted $C_{1-10}$ alkoxy, optionally substituted heteroaryloxy, optionally substituted heterocyclyloxy or optionally substituted cycloalkyloxy;

Y is selected from a single bond, —O—, —C(O)—, —S—, —NR'"—, —C(O)NR'"—, and —NR'"C(O)— (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

L is selected from a divalent linker group of 2-6 atoms in length selected from optionally substituted $C_{2-6}$ alkylene, optionally substituted $C_{3-6}$ cycloalkylene, optionally substituted $C_{2-6}$ alkenylene, and optionally substituted $C_{2-6}$ alkynylene; and $R_8$ is selected from optionally substituted aryl, optionally substituted heterocyclyl, optionally substituted heteroaryl, optionally substituted aryloxy, optionally substituted heterocyclyloxy, optionally substituted heteroaryloxy, —NHR'" (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and SR'" (where is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In other preferred embodiments of the invention, and with reference to the general formulae I, Ia, and Ia', one or more of the following preferred definitions may apply:

f) $R_5$ is defined by —Y-L-$R_8$
where Y is O or single bond;
L is optionally substituted $C_{2-6}$ alkylene or optionally substituted $C_{3-6}$ cycloalkylene; and
$R_8$ is selected from optionally substituted aryl, optionally substituted heterocyclyl, optionally substituted heteroaryl, optionally substituted aryloxy, optionally substituted heterocyclyloxy, optionally substituted heteroaryloxy, —NHR'" (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and SR'" (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

g) $R_1$ is hydrogen, $C_1$-$C_4$ alkyl, or halo $C_{2-4}$ alkyl;
h) $R_3$ is selected from —C(O)$C_1$-$C_3$ alkyl, —C(OH)$C_1$-$C_3$ alkyl, —S(O)$_2$ $C_1$-$C_3$alkyl, —C(O)NH($C_1$-$C_3$ alkyl), —C(O)N($C_1$-$C_3$ alkyl)$_2$, and —C(O)halo $C_{2-4}$ alkyl; and
i) $R_4$ is selected from a terminally substituted $C_{1-6}$ alkyloxy (preferably substituted by NH$_2$, dialkylamino, monodialkylamino, guanidino, optionally substituted aryl, optionally substituted heteroaryl, optionally substituted heterocyclyl, optionally substituted aryloxy, optionally substituted heteroaryloxy, or optionally substituted heterocyclyloxy), optionally substituted heterocyclyloxy, optionally substituted heteroaryloxy, or optionally substituted cycloalkyloxy.

In further preferred embodiments of the invention, and with reference to the general formulae I, Ia, and Ia', one or more of the following further definitions may apply:

j) $R_5$ is defined by —Y-L-$R_8$ where Y is O; L is optionally substituted $C_{2-6}$ alkylene or optionally substituted $C_{3-8}$ cycloalkylene; and $R_8$ is optionally substituted aryl, optionally substituted heteroaryl, or optionally substituted heterocyclyl;

k) $R_4$ is selected from $C_{1-4}$ alkoxy terminally substituted by a group selected from $NH_2$, dialkylamino, monodialkylamino, guanidino, optionally substituted aryl, and optionally substituted heteroaryl; optionally substituted heterocyclyl; optionally substituted heterocyclyloxy; and optionally substituted heteroaryloxy;

l) $R_3$ is —C(O)$C_{1-3}$ alkyl or —C(OH)$C_{1-3}$ alkyl;

m) $R_2$ is $C_{1-4}$ alkyl or halo (preferably chloro); and n) $R_1$ is selected from $C_{1-4}$ alkyl (preferably methyl, ethyl, n-propyl, and isopropyl), $C_{3-6}$ cycloalkyl (preferably cyclopropyl), and halo $C_{1-3}$ alkyl (preferably $CHF_2$ and $CF_3$).

More specific embodiments of $R_4$ include:

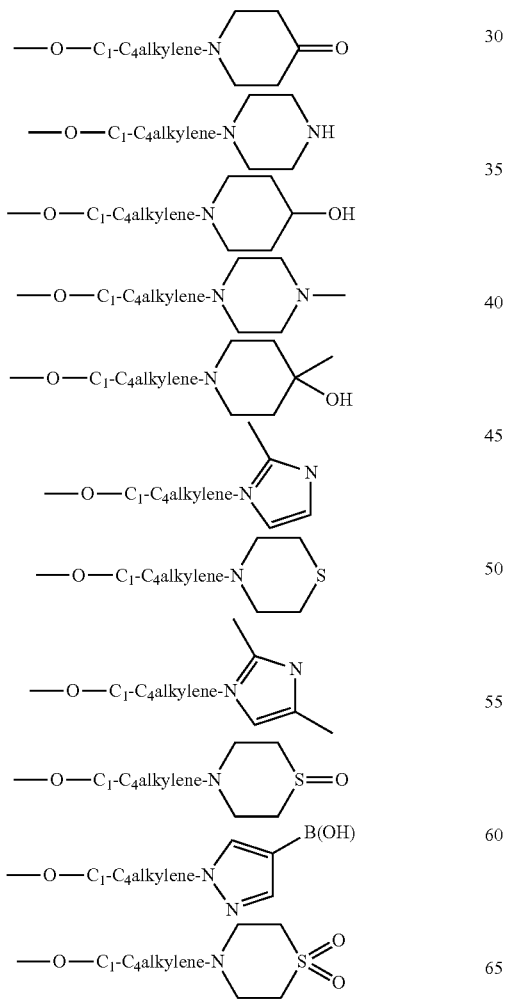

-continued

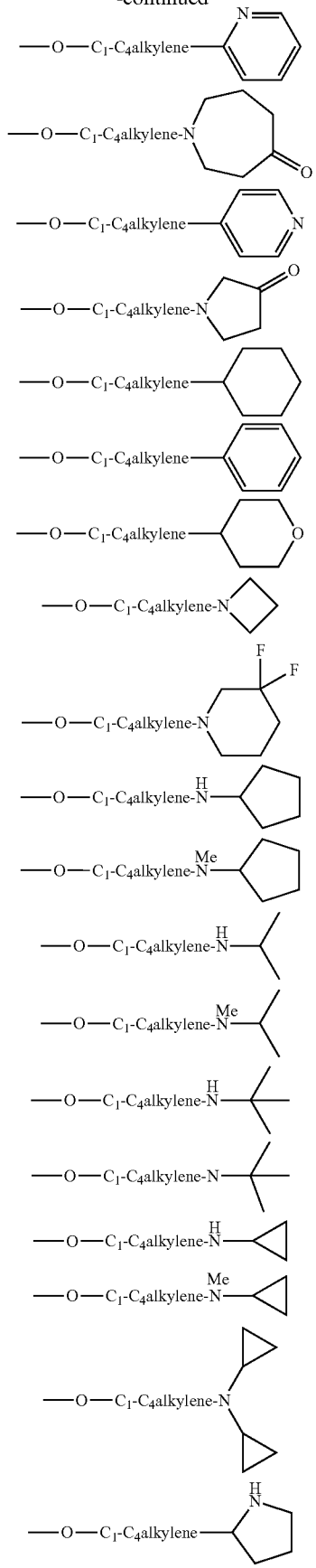

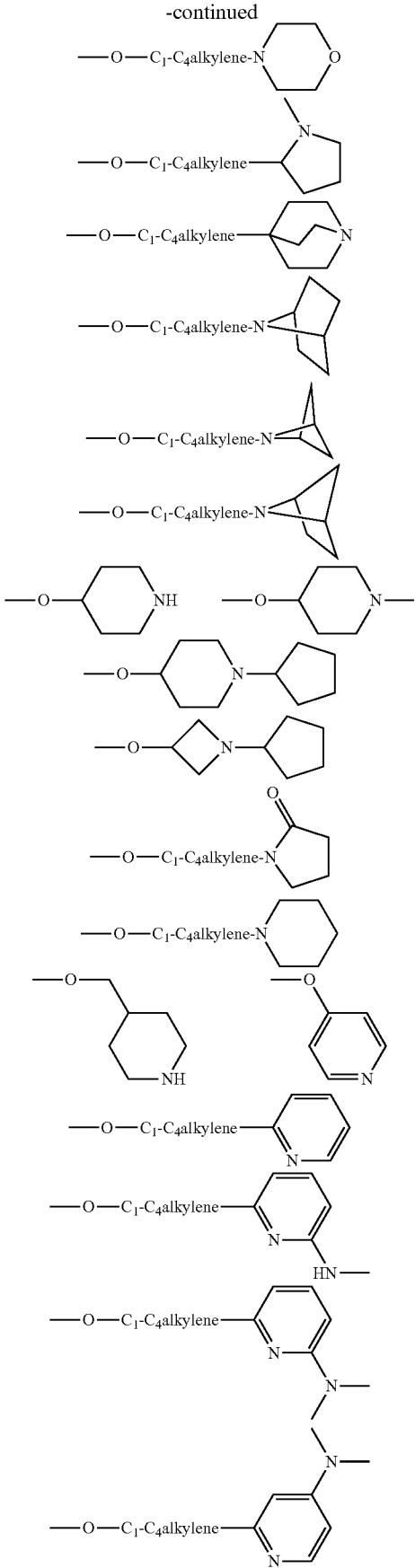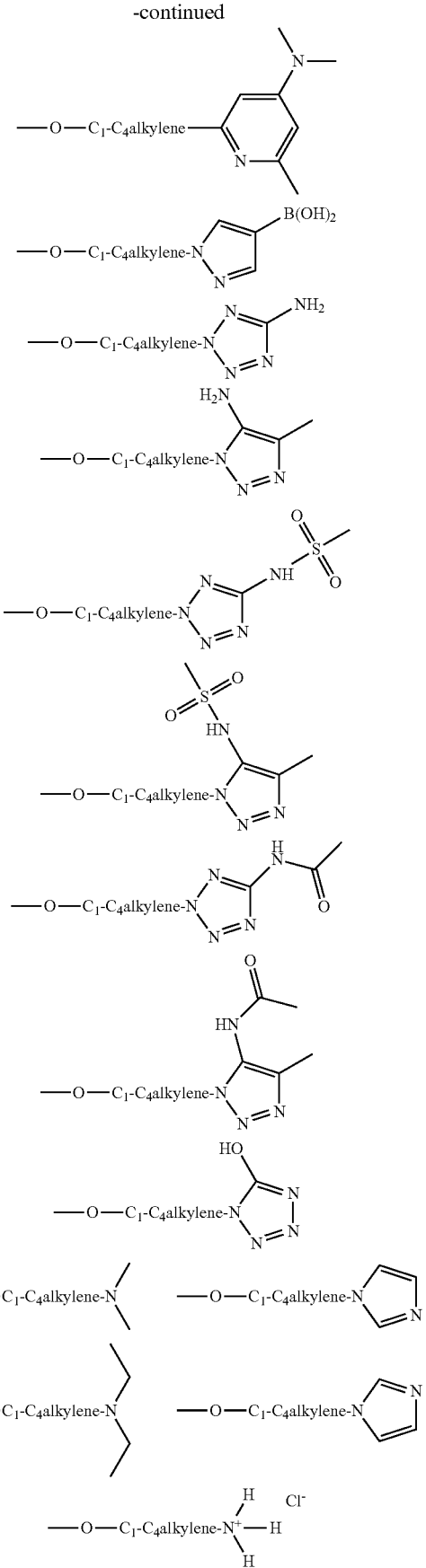

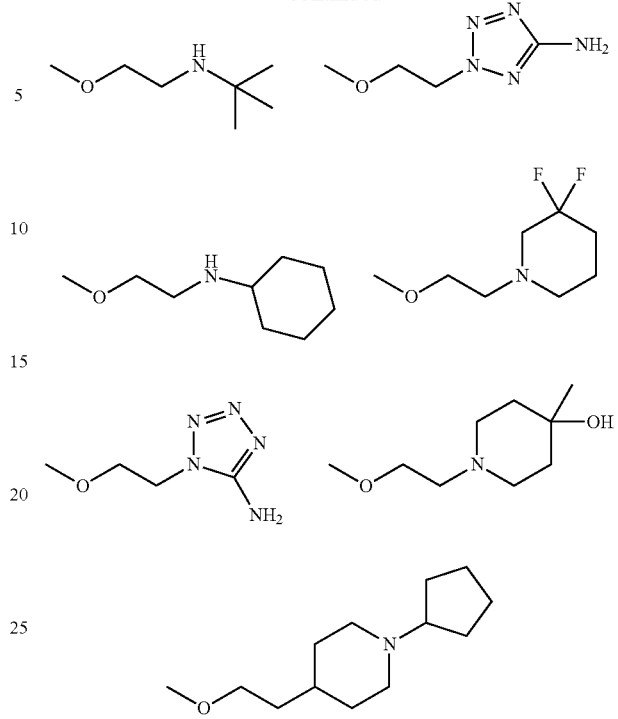

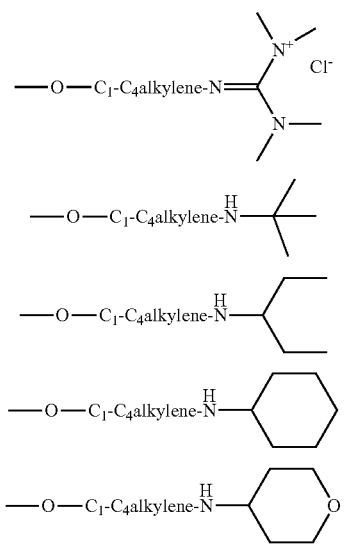

Preferably the $C_{1-4}$ alkylene group in the above embodiments is a $C_{1-3}$ alkylene group and more preferably, ethylene.

Even more specific embodiments of $R_4$ include:

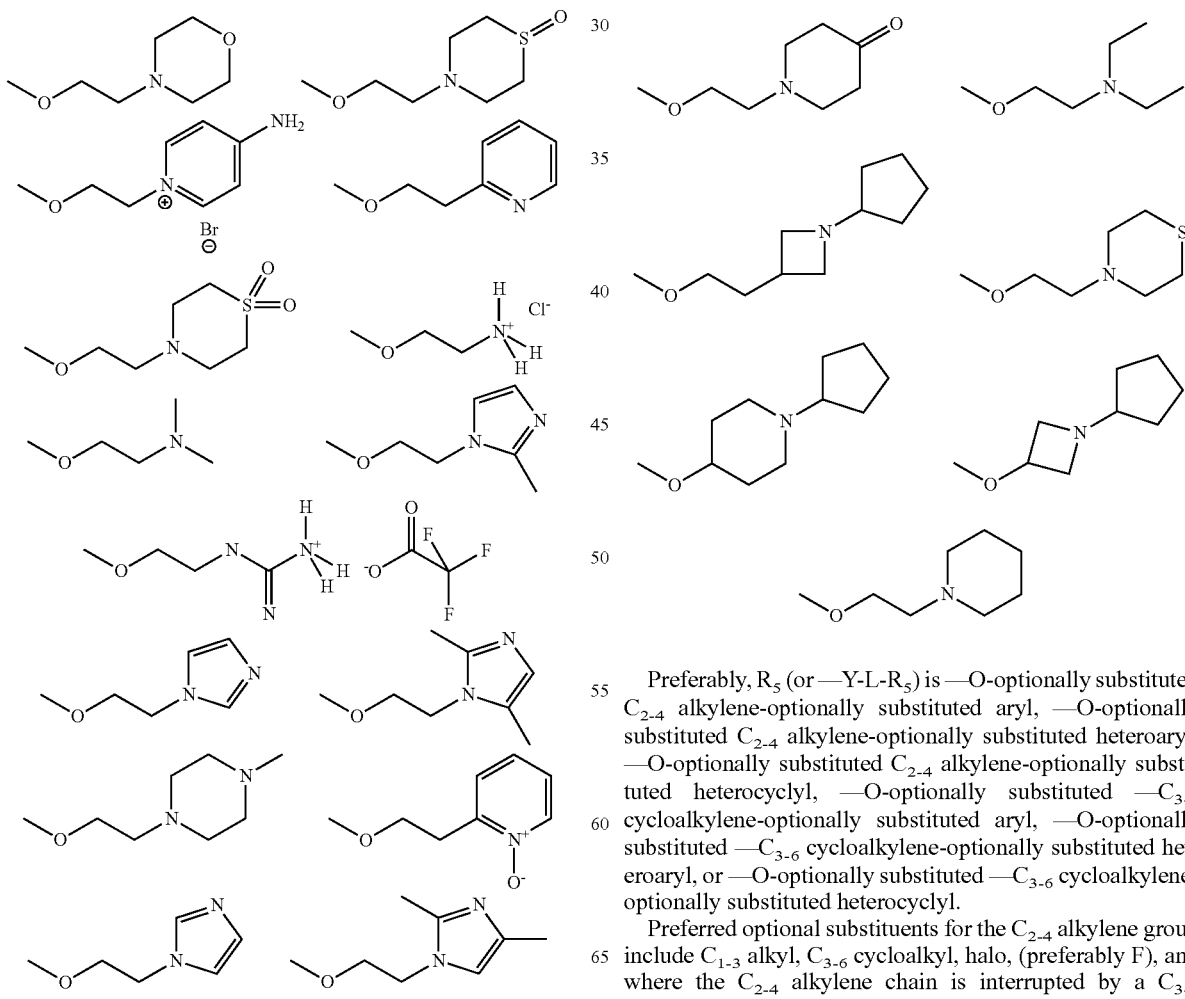

Preferably, $R_5$ (or —Y-L-$R_5$) is —O-optionally substituted $C_{2-4}$ alkylene-optionally substituted aryl, —O-optionally substituted $C_{2-4}$ alkylene-optionally substituted heteroaryl, —O-optionally substituted $C_{2-4}$ alkylene-optionally substituted heterocyclyl, —O-optionally substituted —$C_{3-6}$ cycloalkylene-optionally substituted aryl, —O-optionally substituted —$C_{3-6}$ cycloalkylene-optionally substituted heteroaryl, or —O-optionally substituted —$C_{3-6}$ cycloalkylene-optionally substituted heterocyclyl.

Preferred optional substituents for the $C_{2-4}$ alkylene group include $C_{1-3}$ alkyl, $C_{3-6}$ cycloalkyl, halo, (preferably F), and where the $C_{2-4}$ alkylene chain is interrupted by a $C_{3-6}$ cycloalkyl group.

More specific embodiments of $R_5$ or (—Y-L-$R_8$) include:

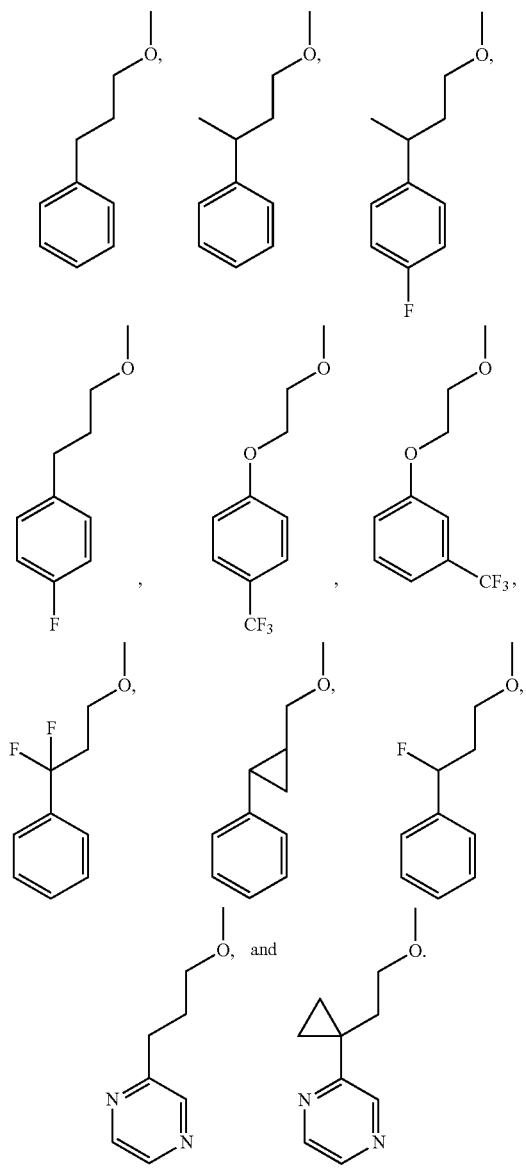

Most preferably, $R_5$ (or —Y-L-$R_8$) is

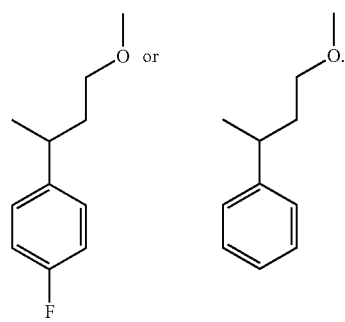

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds of formulae I, Ia, or Ia' or pharmaceutically acceptable salts thereof, including pharmaceutically acceptable derivatives thereof, and optionally a pharmaceutically acceptable carrier or diluent.

In another aspect, the present invention provides pharmaceutical compositions for use as a Kv1.3 ion channel blocker, more particularly as an immunosuppressant, the composition comprising an effective amount of a compound of Formulae I, Ia, or Ia' or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of compound of Formulae I/Ia/Ia' administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The compositions may further contain one or more other immunosuppressants or other multiple sclerosis therapeutics.

For example the compositions may contain a second immunosuppressive agent or other multiple sclerosis therapeutic such as azathioprine, brequinar sodium, deoxyspergualin, mizaribine, mycophenolic acid morpholino ester, cyclosporin, FK-506, rapamycin, interferon beta-1b, interferon beta-1a, glatiramer acetate, natalizumab or mitoxantrone.

The compounds of the present invention may be useful in the therapeutic or prophylactic treatment of the resistance to transplantation of organs or tissue (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases; rheumatoid arthritis, systemic lupus erythematosus, nephrotic syndrome lupus, Palmo-planter pustulosis, Hashimoto's thyroiditis, multiple sclerosis, Guillain-Barre syndrome, myasthenia gravis, type I diabetes uveitis, juvenile-onset or recent-onset diabetes mellitus, diabetic neuropathy, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Meniere's disease, polyneuritis, multiple neuritis, mononeuritis, radiculopathy, hyperthyroidism, Basedow's disease, pure red cell aplasia, aplastic anaemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T-cell lymphoma, arteriosclerosis, atherosclerosis, aortitis syndrome, polyarteritis nodosa, myocardosis, scleroderma, Wegener's granuloma, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Sjoegren's syndrome, Addison's disease, ischemia-reperfusion injury of organs which occurs upon preservation, transplantation or ischemic disease, for example, thrombosis and cardiac infarction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Berger's disease, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, preventing or treating activity of cytomegalovirus infection, HCMV infection, and anti-inflammatory activity.

For certain of the abovementioned conditions it is clear that the compounds may be used prophylactically as well as for the alleviation of acute symptoms.

References herein to "treatment" or the like are to be understood to include such prophylactic treatment, as well as therapeutic treatments.

It is envisaged that the compounds may be particularly useful in the treatment of multiple sclerosis. This chronic neurological disorder affects the nerves of the central nervous system. As discussed earlier most nerves in the body are normally insulated by a protective sheath of fatty substance called myelin. Multiple sclerosis causes demyelination, in which this protective sheath becomes inflamed and ultimately destroyed.

By modulating or changing the immune system response that is thought to be responsible for the attack on the central nervous system it should be possible to attack the cause of the disease itself, rather than the more traditional method of controlling the symptoms.

The nature of the disease is such that it may be possible to control multiple sclerosis without unduly suppressing the patient's immune system. Based on the earlier discussed chronically activated human T-lymphocytes study, it is speculated that multiple sclerosis may be a product of chronically activated T-cells having a channel phenotype characterised by high expression of Kv1.3 channels and low numbers of IKCa1 channels. As this channel phenotype is distinct from that seen in quiescent and acutely activated cells it may provide a useful means for controlling multiple sclerosis without the significant side effects of less specific drugs.

Thus in another aspect of the invention there is provided a method of preventing or treating autoimmune or chronic inflammatory diseases, the prevention of rejection of foreign organ transplants and/or related afflictions, said method including the step of administrating a compound of formulae I, Ia, or Ia', or salt thereof, or a composition comprising the compound or salt thereof.

Accordingly in a preferred form of the invention, there is provided a means for controlling multiple sclerosis by the application of a blocker of the Kv1.3 channel, preferably a selective channel blocker of the Kv1.3 channel, by the application of a compound of formulae I/Ia/Ia' or salt thereof, including a pharmaceutically acceptable derivative thereof, or a composition comprising the compound of formulae I, Ia, or Ia' or salt thereof, or a pharmaceutically acceptable derivative thereof.

In another preferred form of the invention there is provided a method for preventing or treating diabetes mellitus including the step of administrating a compound of formulae I/Ia/Ia' or a pharmaceutically acceptable salt thereof, including a pharmaceutically acceptable derivative thereof, or a composition comprising the compound or pharmaceutically acceptable salt thereof, or pharmaceutically acceptable derivative thereof.

In another preferred form of the invention there is provided a method for preventing or treating rheumatoid arthritis including the step of administrating a compound of formulae I/Ia/Ia' or a pharmaceutically acceptable salt thereof, including a pharmaceutically acceptable derivative thereof, or a composition comprising the compound or pharmaceutically acceptable salt thereof, or pharmaceutically acceptable derivative thereof.

In another preferred form of the invention there is provided a method for preventing or treating psoriasis including the step of administrating a compound of formulae I/Ia/I' or a pharmaceutically acceptable salt thereof, including a pharmaceutically acceptable derivative thereof, or a composition comprising the compound or pharmaceutically acceptable salt thereof, or pharmaceutically acceptable derivative thereof.

In another preferred form of the invention there is provided a method for preventing or treating cardiac arrhythmia including the step of administrating a compound of formulae I/Ia/I' or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect, the invention provides a method of modulating potassium ion channel activity of T-cells by the application of a compound of Formulae I, Ia, or Ia' or a pharmaceutically acceptable salt thereof, including a pharmaceutically acceptable derivative thereof, or a composition comprising the same, to said T cells. Preferably the compounds of the invention inhibit the potassium ion channel activity of T-cells.

Preferably the potassium channel activity inhibited by the compound of Formulae I, Ia, or Ia' is a voltage-gated potassium channel, for example, Kv1.1-Kv1.7. More preferably the potassium ion channel activity is the voltage-gated potassium channel, Kv1.3 of a T-cell. Preferably the compound selectively inhibits the Kv1.3 channel.

In a further aspect of the present invention, there is provided the use of a compound of formulae I, Ia, or Ia' or salt thereof, in the preparation of a medicament for the treatment (therapeutic or prophylactic) of disease states mediated by potassium channels, and in particular by blocking the Kv1.3 channel.

In a further aspect of the invention there is provided a process for the production of the compounds of Formulae I, Ia, or Ia' or salts thereof, including pharmaceutically acceptable derivatives thereof.

The compounds of the invention can be made from building up specifically substituted/functionalised benzenes using standard aromatic (electrophilic and nucleophilic) chemistry.

Scheme 1 illustrates a general procedure for preparing benzoxazoles of the present invention:

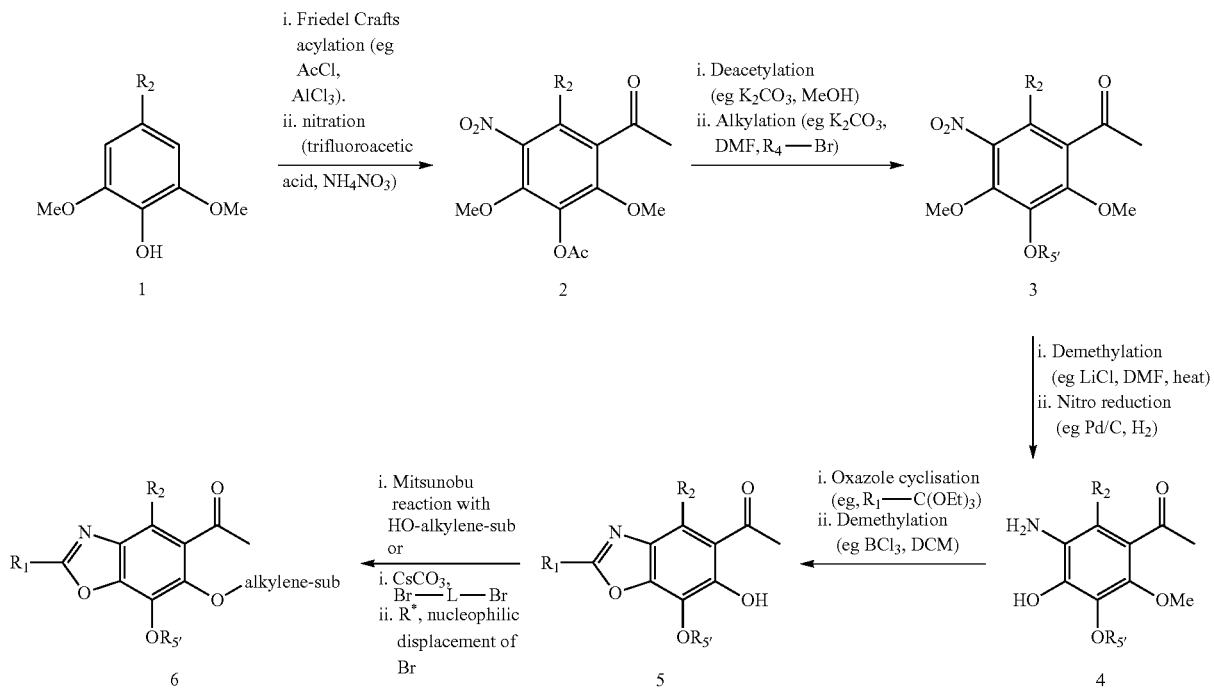

Compounds of formulae I/Ia/Ia' where $R_6$ is other than Me may be prepared by transformation of the C5 acetyl group. For instance the reaction of this group with an α-haloester in the presence of zinc (ie under Reformatsky conditions) may afford a β-hydroxyester which may then be suitably oxidized to form a β-carbonylester (ie where —C(O)—$R_6$ is —C(O)—CR'R"—$CO_2$R (where R' and R" are independently selected from H and lower alkyl, and R is lower alkyl, optionally substituted alkyl, optionally substituted aryl or optionally substituted arylalkyl). Alternatively, other acid chlorides may be used in the Friedel Crafts reaction in place of acetyl chloride (AcCl), for examples propionyl chloride, butyryl chloride, pentanoic acid chloride etc. Additionally, other compounds of the invention can be made by reduction of the ketone with NaBH$_4$ or other reducing agents to give an alcohol.

Also, further substituents for R$_6$ can be added by initially halogenating the C5 acetyl group with, for instance, Br$_2$ to form —C(O)CH$_2$Br. Substitution of the halogen with a suitable nucleophilic group may afford —C(O)R$_6$ where R$_6$ is —CH$_2$OR, and —CH$_2$SR, (where R is selected from hydrogen, optionally substituted alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), or —CH$_2$NR'R'' (where R' and R'' are independently selected from hydrogen or lower alkyl).

Furthermore, with the use of excess base and a halogen, the acetyl methyl group can be trihalogenated and cleaved via the haloform reaction to form a carboxylic acid (ie where R$_6$ is OH). Further transformation of the carboxylic acid, under conditions known in the art may produce esters (where R$_6$ is OR) and amides (where R$_6$ is —NR'R'').

Also, the methyl or methylene groups α to the carbonyl (eg where R$_6$ is CH$_3$ or CH$_2$CH$_3$) can be oxidized with selenium dioxide to give respectively, a ketoaldehydes (ie R$_6$ is —C(O)H) and α-diketones (ie R$_6$ is —C(O)CH$_3$). In addition reacting the C5 acetyl with an appropriate base and reacting the formed enolate with suitable acyl halides or dialkylcarbonates may afford compounds where R$_6$ is —CH$_2$C(O)R and —CH$_2$C(O)OR respectively, where R is preferably lower alkyl.

Compounds of formulae I/Ia/Ia' where R$_2$ is —CN may be prepared by the synthetic route shown in Scheme 1 from commercially available 2,6-dimethoxy-4-cyanophenol as compound 1. Compounds of formulae I/Ia/Ia' where R$_2$ is heterocyclyl/heteroaryl may be prepared by the synthetic route shown in Scheme 2.

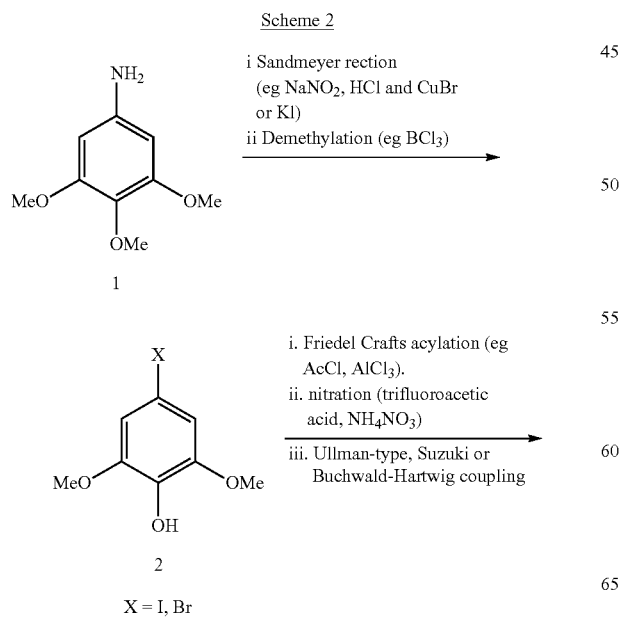

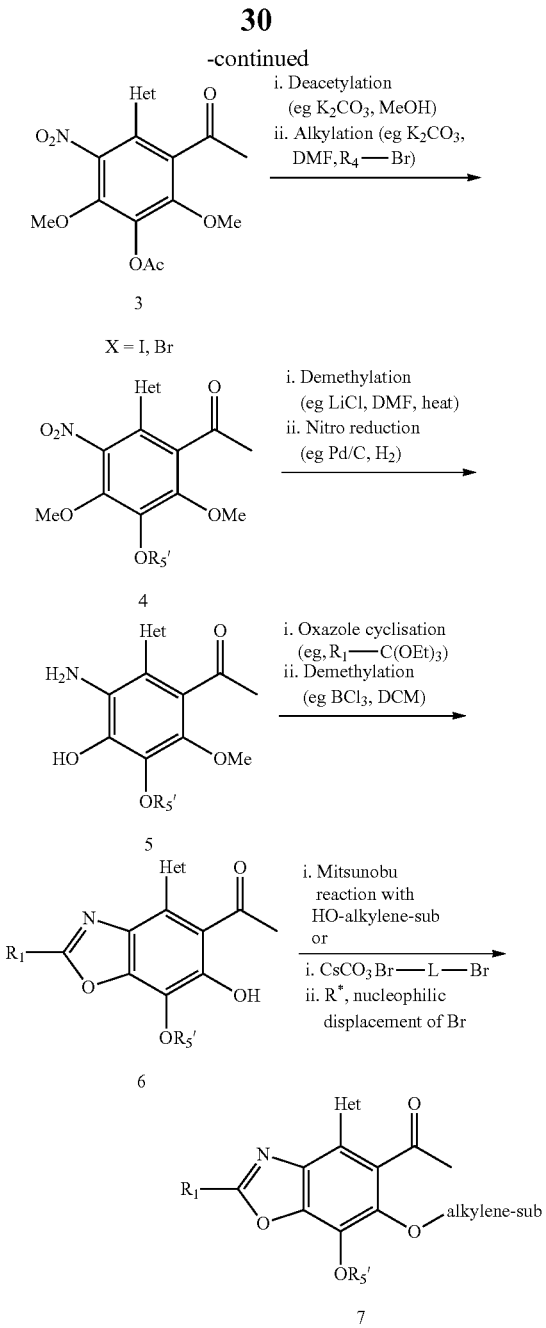

In the above schemes the following abbreviations were used:—
TFA trifluoroacetic acid
TFAA trifluoroacetic acid anhydride
PMBCl para methoxybenzyl chloride
DMAP 4-(dimethylamino)pyridine
Aq aqueous
Tf$_2$O triflic anhydride
Het optionally substituted heterocyclyl or optionally substituted heteroaryl Another variation is to add, remove or modify the substituents of the product to form new derivatives. This could be achieved by using standard techniques for functional group inter-conversion, well known in the industry such as those described in Comprehensive organic transformations: a guide to functional group preparations by Larock R C, New York, VCH Publishers, Inc. 1989.

Examples of possible functional group inter-conversions are: —C(O)NRR' from —CO$_2$CH$_3$ by heating with or without catalytic metal cyanide, e.g. NaCN, and HNRR' in CH$_3$OH; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R")SR''' with H$_3$NR$^+$OAc$^-$ by heating in alcohol; —C(NR'R")SR from —C(S)NR'R" with R—I in an inert solvent, e.g. acetone; —C(S)NR'R" (where R' or R" is not hydrogen) from —C(S)NH$_2$ with HNR'R"; —C(=NCN)—NR'R" from —C(=NR'R")—SR with NH$_2$CN by heating in anhydrous alcohol, alternatively from —C(=NH)—NR'R" by treatment with BrCN and NaOEt in EtOH; —NR—C(=NCN)SR from —NHR' by treatment with (RS)$_2$C=NCN; —NR"SO$_2$R from —NHR' by treatment with ClSO$_2$R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR' with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R' from RC(O)R' by R"CO$_3$H; —CCH$_2$OH from —C(O)OR' with Na/R'OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH; —S(O)$_2$R from —SR with mCPBA.

In order that the present invention may be more readily understood, we provide the following non-limiting examples.

EXAMPLES

General Procedure

General Procedures
General Procedure A: Alkylation of 2,6-Dimethoxyphenols

NaH (60% dispersion in oil, 1.2 eq.) was added to a stirred solution of the 2,6-dimethoxyphenol (1.0 eq.) in dry DMF (1.0 M) at room temperature. After the reaction mixture was stirred for 0.25 h, a solution of the bromoalkane (1.03 eq.) in dry DMF (5.0 M) was added, followed by stirring at room temperature overnight. The mixture was quenched with NH$_4$Cl$_{(aq)}$ (sat.), extracted with EtOAc and washed with water. The organic layer was separated, dried over MgSO$_4$ and concentrated in vacuo. The crude product was purified by flash chromatography (silica gel).

General Procedure B: Friedel-Crafts Reaction with Acetyl Chloride

A mixture of the substituted benzene (1.0 eq.) and acetyl chloride (1.1 eq.) were stirred under nitrogen at room temperature for 0.25 h, then TiCl$_4$ (1.10 eq.) was added dropwise. The dark brown mixture was stirred at room temperature for 0.5 h and then quenched with NH$_4$Cl$_{(aq)}$ (sat.), extracted with EtOAc and washed with water. The organic layer was separated, dried over MgSO$_4$, and purified by flash chromatography (silica gel, EtOAc). The solution was concentrated in vacuo to give the ketone.

General Procedure C: Selective Demethylation of Methyl Ether

A solution of BCl$_3$ in CH$_2$Cl$_2$ (1.0 M, 1.1 eq.) was added to a stirred solution of the methyl ether (1.0 eq.) in dry CH$_2$Cl$_2$ (0.25 M) under nitrogen at 0° C. The mixture was stirred for 1-2 h, quenched with NH$_4$Cl$_{(aq)}$ (sat.), extracted with EtOAc (30 mL) and washed with water. The organic layer was separated, dried over MgSO$_4$ and passed through silica gel to give the phenol.

General Procedure D: Alkylation of Phenols

A suspension of the phenol (1.0 eq., 0.2 M), Cs$_2$CO$_3$ or K$_2$CO$_3$ (1.5 eq.) and alkyl or benzyl halide or mesylate (generally 1.2 eq.) in dry DMF was stirred under N$_2$ at 60° C. until completion as determined by TLC (1-5 h). The reaction mixture was then diluted with EtOAc and washed twice with either citric acid$_{(aq.)}$ (10%) or HCl$_{(aq.)}$ (2 M) and then brine, dried over MgSO$_4$, and concentrated in vacuo. The crude residue was purified flash chromatography (silica gel).

General Procedure E: Alkylation of Amines and N-Heterocycles

To a solution of the bromide (0.2-0.5 M) in dry dimethylformamide was added the amine or N-heterocycle (3-15 eq.) and the reaction was stirred at 80-90° C. under a N$_2$ atmosphere until the reaction was complete by TLC (~5 h). The reaction was quenched with NH$_4$Cl$_{(aq.)}$ (sat.) and extracted with EtOAc. The organic layer was washed with water, then brine, dried over MgSO$_4$ and concentrated in vacuo. The crude residue was purified by flash chromatography (silica gel).

General Procedure F: Alkylation of Phenols Using an Alkyl Chloride

To a stirred suspension the phenol (1.0 eq.), K$_2$CO$_3$ or Cs$_2$CO$_3$ (2.0 eq.) and NaI (0.30 eq.), pre-dried under vacuum at 100° C. for 5 h in dry DMF or DMSO (0.1 M of phenol) was added the alkyl chloride (2.0 eq.) and the reaction was heated at 60° C. for 16 h. After this time the reaction was cooled, diluted with EtOAc and washed thrice with water. The organic layer was dried over MgSO$_4$, concentrated in vacuo and the crude residue was purified by flash chromatography (silica gel).

Example 1i

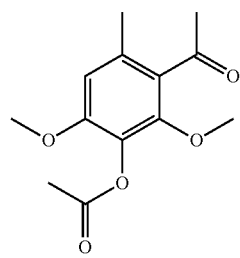 [SMILES: COc1cc(C)c(C(C)=O)c(OC)c1OC(C)=O]

1a) 3-Acetyl-2,6-dimethoxy-4-methylphenylacetate

A stirred solution of 3,5-dimethoxy-4-hydroxytoluene (10.63 g, 0.063 mol) in acetyl chloride (26.6 mL, 0.373 mol) was heated at 40° C. for 0.5 h. LCMS showed complete conversion to the acetate intermediate. The reaction mixture was cooled to 0° C. and DCM (100 mL) was added. TiCl$_4$ (7.6 mL, 0.069 mol) was added dropwise and the reaction mixture warmed to room temperature. After 1.5 h, LCMS showed complete conversion to the bisacetylated product. The reaction was quenched by pouring onto ice/H$_2$O (500 mL) and the product extracted with DCM (200 mL). The organic phase was washed with H$_2$O (2×100 mL), dried over MgSO$_4$ and concentrated in vacuo. The product was recrystallised from 3:1 hexane/EtOAc yielding the title compound (11.1 g, 69%) as a red/brown crystalline solid. $^1$H NMR (300 MHz, CDCl$_3$) δ 6.53 (s, 1H), 3.80 (s, 3H), 3.76 (s, 3H), 2.47 (s, 3H), 2.32 (s, 3H), 2.24 (s, 3H), MS (ES$^+$) m/z [M+H]$^+$ 253.2.

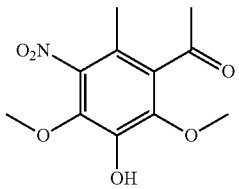 [SMILES: COc1c(O)c(OC)c([N+](=O)[O-])c(C)c1C(C)=O]

1b) 1-(3-Hydroxy-2,4-dimethoxy-6-methyl-5-nitrophenyl)ethanone

To a stirred solution of Example 1a) (14.28 g, 56.54 mmol) in a mixture of CHCl$_3$ (28 mL) and trifluoroacetic anhydride (27.5 mL, 197.89 mmol) at 0° C. was added solid NH$_4$NO$_3$ (5.04 g, 62.97 mmol) and the reaction mixture was stirred for 2 h. Heat was liberated as the NH$_4$NO$_3$ dissolved. By LCMS there was complete consumption of 1a) at 2 h. The reaction mixture was cooled to 0° C. and quenched with NH$_4$Cl$_{(aq)}$ (sat., 100 mL) The organic layer was separated and dried over MgSO$_4$. The solution was concentrated in vacuo to give a pale oil (10.59 g), which was used in the next step without purification. To a stirred solution of the crude intermediate (10.59 g) in methanol (30 mL) was added K$_2$CO$_3$ (12.32 g, 89.14 mmol). The reaction was stirred for 3 h at room temperature. Excess K$_2$CO$_3$ was filtered and the solution concentrated in vacuo. The crude material was redissolved in Et$_2$O (200 mL) and acidified with HCl (2 N, pH=2). The phases were separated and the organic layer washed with H$_2$O (2×100 mL) and brine (100 mL), and dried over Na$_2$SO$_4$. The crude product was purified by flash chromatography (silica gel, CH$_2$Cl$_2$) to give the title compound (10.10 g, 70% over 2 steps) as pale oil. $^1$H NMR (300 MHz, CDCl$_3$) δ 5.70 (s, 1H), 3.95 (s, 3H), 3.85 (s, 3H), 2.49 (s, 3H), 2.07 (s, 3H), MS (ES$^+$) m/z [M+H]$^+$ 256.2.

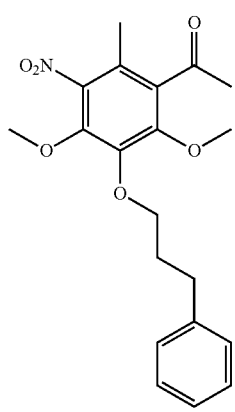 [SMILES: COc1c(OCCCc2ccccc2)c(OC)c([N+](=O)[O-])c(C)c1C(C)=O]

1c) 1-(2,4-Dimethoxy-6-methyl-5-nitro-3-(3-phenylpropoxy)phenyl) ethanone

Example 1b) (1.10 g, 4.3 mmol) and 3-bromo-1-phenylpropane (0.73 mL, 4.7 mmol) were reacted as described under General Procedure A to give the title compound (1.60 g, 99%) as a creamy oil. $^1$H NMR (300 MHz, CDCl$_3$) δ 7.31-7.19 (m, 5H), 4.06 (t, J=6.4 Hz, 2H), 3.95 (s, 3H), 3.90 (s, 3H), 2.81 (t, J=7.7 Hz, 2H), 2.46 (s, 3H), 2.10-2.05 (m, 2H), 2.10 (s, 3H), ESIMS m/z [M+H]$^+$ 374.2.

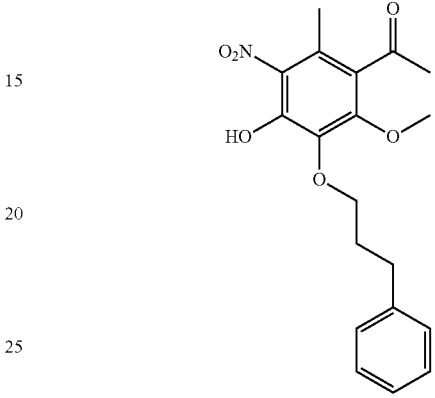

1d) 1-(4-Hydroxy-2-methoxy-6-methyl-5-nitro-3-(3-phenylpropoxy)phenyl)ethanone

LiCl (600 mg, 14.0 mmol) was added to a solution of Example 1c) (1.0 g, 2.68 mmol) in dry DMF (6 mL). The mixture was stirred at 110° C. for 3 h (TLC). The solution was concentrated in vacuo and the residue was dissolved in EtOAc (100 mL) and this solution was washed with water. The organic layer was dried over MgSO$_4$ and concentrated in vacuo and the crude product was purified by flash chromatography (silica gel, hexane/diethyl ether 100:0, 70:30) to give the title compound (450 mg, 47%) as a pale oil. $^1$H NMR (300 MHz, CDCl$_3$) δ 9.67 (s, 1H), 7.31-7.17 (m, 5H), 4.09 (t, J=6.4 Hz, 2H), 3.97 (s, 3H), 2.82 (t, J=7.3 Hz, 2H), 2.47 (s, 3H), 2.32 (s, 3H), 2.16-2.07 (m, 2H), ESIMS m/z [M+H]$^+$ 360.3.

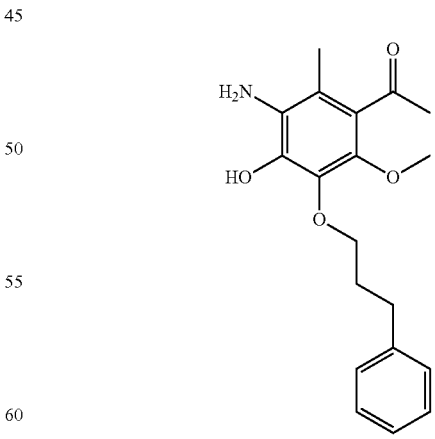

1e) 1-(3-Amino-4-hydroxy-6-methoxy-2-methyl-5-(3-phenylpropoxy)phenyl)ethanone

A mixture of Example 1d) (360 mg, 1.00 mmol) and Pd/C (10%; 150 mg) in EtOAc (30 mL) was stirred at room temperature under an atmosphere of hydrogen for 2 h (TLC). The mixture was filtered through Celite and the solution was concentrated in vacuo to gave the crude product (291 mg, 88%) as a light green oil, which was used in the next step without purification. $^1$H NMR (300 MHz, CDCl$_3$) δ 7.31-7.19 (m, 5H), 4.09 (t, J=6.6 Hz, 2H), 3.77 (s, 3H), 2.79 (t, J=7.2 Hz, 2H), 2.50 (s, 3H), 2.13-2.06 (m, 2H), 1.98 (s, 3H).

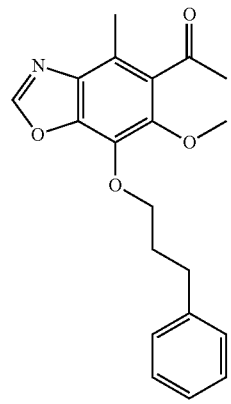 [SMILES: COc1c(C(C)=O)c(C)c2ncoc2c1OCCCc1ccccc1]

1f) 5-Acetyl-6-methoxy-4-methyl-7-(3-phenylpropoxy)benzo[d]oxazole

A solution of Example 1e) (258 mg, 0.78 mmol), dry DMF (4 mL) and triethylorthoformate (2 mL, excess) was stirred at 60° C. for 0.5 h. The solution was concentrated in vacuo and the residue was taken up in CH$_2$Cl$_2$ (15 mL) and washed with water and dried over MgSO$_4$ to give the title compound (152 mg, 57%) as a pale oil. $^1$H NMR (300 MHz, CDCl$_3$) δ 7.98 (s, 1H), 7.30-7.19 (m, 5H), 4.37 (t, J=6.4 Hz, 2H), 3.90 (s, 3H), 2.86 (t, J=7.40 Hz, 2H), 2.52 (s, 3H), 2.43 (s, 3H), 2.17-2.08 (m, 2H).

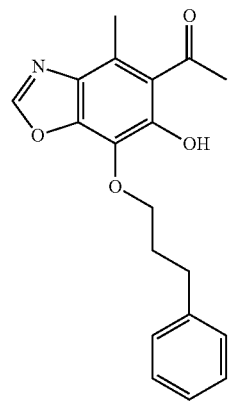 [SMILES: CC(=O)c1c(O)c(OCCCc2ccccc2)c2ocnc2c1C]

1g) 5-Acetyl-6-hydroxy-4-methyl-7-(3-phenylpropoxy)benzo[d]oxazole

Example 1f) (120 mg, 0.35 mmol) was reacted as described under General Procedure C. The crude residue was purified by flash chromatography (silica gel, CH$_2$Cl$_2$) to give the title compound (92 mg, 80%) as a pale oil. $^1$H NMR (300 MHz, CDCl$_3$) δ 9.99 (s, 1H), 7.91 (s, 1H), 7.30-7.16 (m, 5H), 4.37 (t, J=6.4 Hz, 2H), 2.84 (t, J=7.3 Hz, 2H), 2.70 (s, 3H), 2.68 (s, 3H), 2.17-2.03 (m, 2H), ESIMS m/z [M+H]$^+$ 326.3.

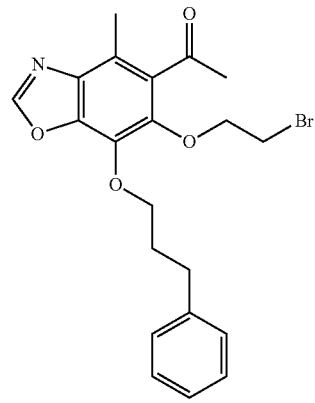 [SMILES: CC(=O)c1c(OCCBr)c(OCCCc2ccccc2)c2ocnc2c1C]

1h) 5-Acetyl-6-(2-bromoethoxy)-4-methyl-7-(3-phenylpropoxy)benzo[d]oxazole

Example 1g) (70 mg, 0.16 mmol) was reacted with dibromoethane (200 uL, excess) as described under General Procedure D to give the title compound (76 mg, 82%) as pale oil, which was used in the next step without purification. $^1$H NMR (300 MHz, CDCl$_3$) δ 7.98 (s, 1H), 7.31-7.19 (m, 5H), 4.41 (t, J=6.37 Hz, 2H), 4.33 (t, J=6.2 Hz, 2H), 3.55 (t, J=6.20 Hz, 2H), 2.85 (t, J=7.4 Hz, 2H), 2.55 (s, 3H), 2.43 (s, 3H), 2.26-2.05 (m, 2H).

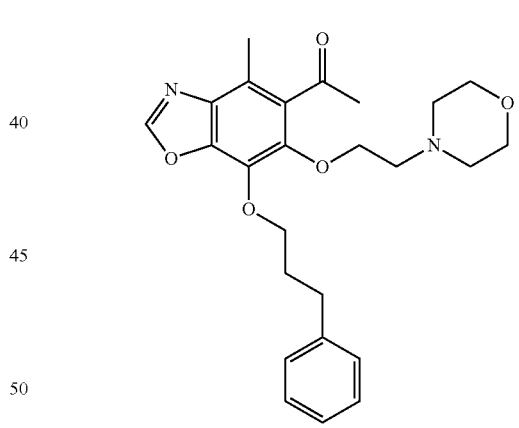

1i) 5-Acetyl-4-methyl-6-(2-morpholinoethoxy)-7-(3-phenylpropoxy)-benzo[d]oxazole Example 1h) (70 mg, 0.16 mmol) was reacted with morpholine as described under General Procedure E. The crude produced was purified by preparative TLC to give the title compound (11 mg, 15%) as pale oil. $^1$H NMR (300 MHz, CDCl$_3$) δ 7.97 (s, 1H), 7.31-7.16 (m, 5H), 4.39 (t, J=6.5 Hz, 2H), 4.15 (t, J=5.6 Hz, 2H), 3.70 (t, J=3.4 Hz, 4H), 2.84 (t, J=7.4 Hz, 2H), 2.68 (t, J=5.6 Hz, 2H), 2.55 (s, 3H), 2.52-2.49 (m, 4H), 2.42 (s, 3H), 2.14-2.08 (m, 2H). ESIMS m/z [M+H]$^+$ 439.

Example 2e

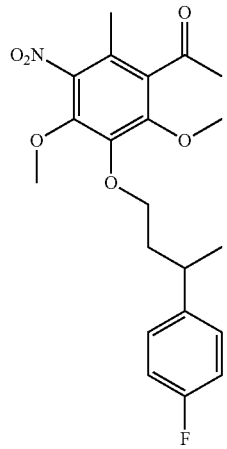 [SMILES: COc1c(OCCC(C)c2ccc(F)cc2)c(OC)c([N+](=O)[O-])c(C)c1C(C)=O]

2a) 1-{3-[3-(4-Fluorophenyl)butoxy]-2,4-dimethoxy-6-methyl-5-nitro-phenyl}-ethanone Example 1b) (3.05 g, 12.0 mmol) and 1-(3-bromo-1-methyl-propyl)-4-fluorobenzene (3.07 g, 13.3 mmol) were reacted as described under General Procedure D. The crude product was purified by flash chromatography (silica gel, hexane/diethyl ether, 1:4) to give the title compound (4.05 g, 84%) as a pale oil. $^1$H NMR (300 MHz, CDCl$_3$) δ 7.19-7.14 (m, 2H), 7.00-6.95 (m, 2H), 3.98-3.83 (m, 8H), 3.03-2.95 (m, 1H), 2.46 (s, 3H), 2.09 (s, 3H), 2.08-2.01 (m, 2H), 1.28 (d, J=6.9 Hz, 3H). ESIMS m/z [M+H]$^+$ 406.2.

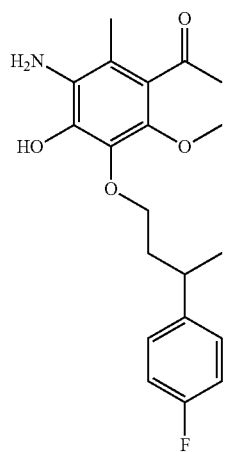 [SMILES: COc1c(OCCC(C)c2ccc(F)cc2)c(O)c(N)c(C)c1C(C)=O]

2b) 1-{3-[3-(4-Fluorophenyl)butoxy]-4-hydroxy-2-methoxy-6-methyl-5-amino-phenyl}-ethanone Example 2a) (0.42 g, 1.03 mmol) was treated with LiCl as described for Example 1d) and the resulting o-nitrophenol was treated with hydrogen in the presence of Pd/C as described for Example 1e). The crude product was not purified further. $^1$H NMR (300 MHz, CDCl$_3$) δ 7.21-7.15 (m, 2H), 7.03-6.96 (m, 2H), 3.97 (t, J=6.6 Hz, 2H), 3.69 (s, 3H), 3.03-2.89 (m, 1H), 2.46 (s, 3H), 2.10-1.95 (m, 5H), 1.29 (d, J=7.2 Hz, 3H). ESIMS m/z [M+H]$^+$ 362.3.

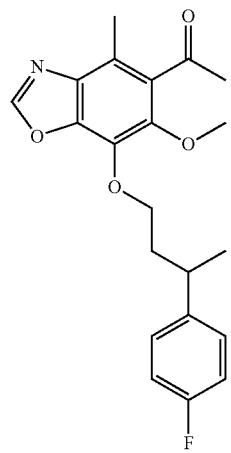 [SMILES: COc1c(C(C)=O)c(C)c2ncoc2c1OCCC(C)c1ccc(F)cc1]

2c) 5-Acetyl-7-[3-(4-fluorophenyl)butoxy]-6-methoxy-4-methyl-benzo[d]oxazole

Example 2b) (446 mg, 1.23 mmol) was treated with trimethyl orthoformate as described for Example 1f. The resulting crude product was purified by flash chromatography (silica gel, hexane/EtOAc, 9:1) to give the title compound (269 mg, 59%) as an oil. $^1$H NMR (300 MHz, CDCl$_3$) δ 7.97 (s, 1H), 7.26-7.16 (m, 2H), 7.00-6.94 (m, 2H), 4.31-4.20 (m, 2H), 3.88 (s, 3H), 3.09-3.06 (m, 1H), 2.53 (s, 3H), 2.42 (s, 3H), 2.12-2.00 (m, 2H), 1.31 (d, J=7.2 Hz, 3H), ESIMS m/z [M+H]$^+$ 372.3.

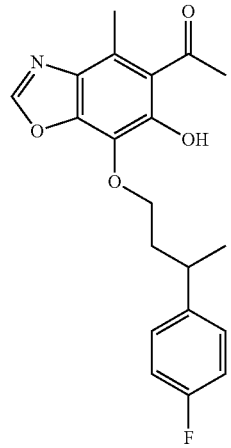 [SMILES: CC(=O)c1c(O)c(OCCC(C)c2ccc(F)cc2)c2ocnc2c1C]

2d) 5-Acetyl-7-[3-(4-fluorophenyl)butoxy]-6-hydroxy-4-methyl-benzo[d]oxazole

Example 2c) (269 mg, 0.72 mmol) was reacted as described under General Procedure C. The crude product was purified by flash chromatography (silica gel, hexane I EtOAc 9:1) to give the title compound (152 mg, 59%). $^1$H NMR (300 MHz, CDCl$_3$) δ 10.19 (s, 1H), 7.97 (s, 1H), 7.26-7.15 (m, 2H), 7.01-6.94 (m, 2H), 4.31-4.15 (m, 2H), 3.10-3.02 (m, 1H), 2.71 (s, 3H), 2.68 (s, 3H), 2.14-1.96 (m, 2H), 1.29 (d, J=7.8 Hz, 3H), ESIMS m/z [M+H]$^+$ 358.3.

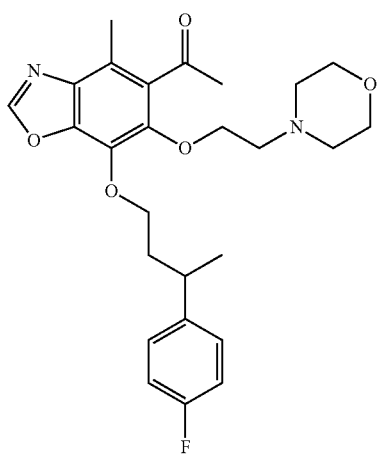 [SMILES: CC(=O)c1c(OCCN2CCOCC2)c(OCCC(C)c2ccc(F)cc2)c2ocnc2c1C]

2e) 5-Acetyl-7-[3-(4-fluorophenyl)butoxy]-4-methyl-6-(2-morpholin-4-yl-ethoxy)benzooxazole Example 2d) (108 mg, 0.30 mmol) was reacted with 4-(2-chloroethyl)morpholine as described under General Procedure F to give the title compound (91 mg, 65%) as brown oil. $^1$H NMR (300 MHz, CDCl$_3$) δ 8.01 (s, 1H), 7.25-7.20 (m, 2H), 7.06-6.99 (m, 2H); 4.34-4.26 (m, 2H); 4.15 (t, J=5.7 Hz, 2H), 3.77 (t, J=4.5 Hz, 2H), 3.15-3.05 (m, 1H), 2.72 (t, J=5.7 Hz, 2H), 2.61 (s, 3H), 2.56 (m, 4H), 2.47 (s, 3H), 2.15-2.04 (m, 2H), 1.36 (d, J=6.9 Hz, 3H), MS (ES$^+$) m/z 471.3 (M+H$^+$).

Example 3

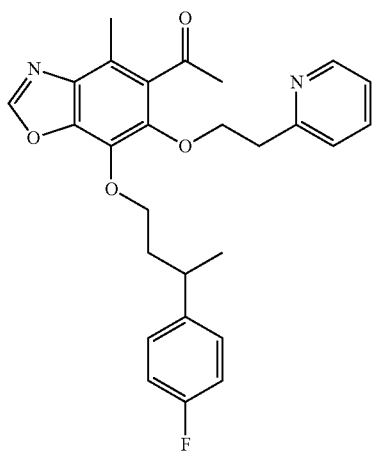 [SMILES: CC(=O)c1c(OCCc2ccccn2)c(OCCC(C)c2ccc(F)cc2)c2ocnc2c1C]

5-Acetyl-7-[3-(4-fluorophenyl)butoxy]-4-methyl-6-(2-pyridin-2-yl-ethoxy)benzooxazole Example 2d) (111 mg, 0.31 mmol) was reacted with 2-(2-mesylethyl)pyridine as described under General Procedure D to give the title compound (51 mg, 36%) as an orange/brown oil. $^1$H NMR (CDCl$_3$) δ 8.54 (dddd, J=5.1, 2.7, 1.8, 0.9 Hz, 1H), 7.95 (s, 1H), 7.61 (dt, J=7.8, 2.1 Hz, 1H), 7.25 (m, 1H), 7.17-7.12 (m, 3H), 6.99-6.93 (m, 2H), 4.34 (t, J=6.6 Hz, 2H), 4.27-4.10 (m, 2H), 3.18 (t, J=6.6 Hz, 2H), 3.05-2.98 (m, 1H), 2.39 (s, 3H), 2.34 (s, 3H), 2.08-1.93 (m, 2H), 1.29 (d, J=6.9 Hz, 3H), MS (ES$^+$) m/z 463.3 (M+H$^+$).

Example 4b

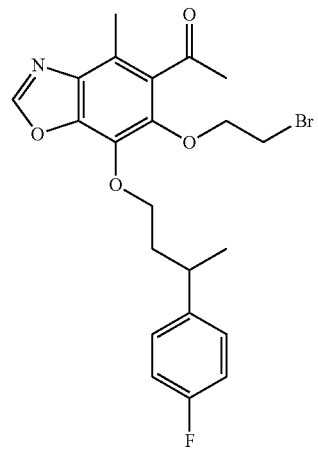 [SMILES: CC(=O)c1c(OCCBr)c(OCCC(C)c2ccc(F)cc2)c2ocnc2c1C]

4a) 5-Acetyl-6-(2-bromoethoxy)-7-[3-(4-fluorophenyl)butoxy]-4-methyl-benzo[d]oxazole Example 2d) (140 mg, 0.39 mmol) was reacted with dibromoethane (339 uL, excess) as described under General Procedure D to give the title compound (173 mg, 95%) as pale-yellow oil, which was used in the next step without purification. $^1$H NMR (300 MHz, CDCl$_3$) δ 7.98 (s, 1H), 7.22-7.17 (m, 2H), 7.01-6.96 (m, 2H), 4.36-4.20 (m, 4H), 3.56 (t, J=6.3 Hz, 2H), 3.12-3.01 (m, 1H), 2.56 (s, 3H), 2.43 (s, 3H), 2.16-1.93 (m, 2H), 1.29 (d, J=6.9 Hz, 3H), MS (ES$^+$) m/z 464.2 (M+H$^+$).

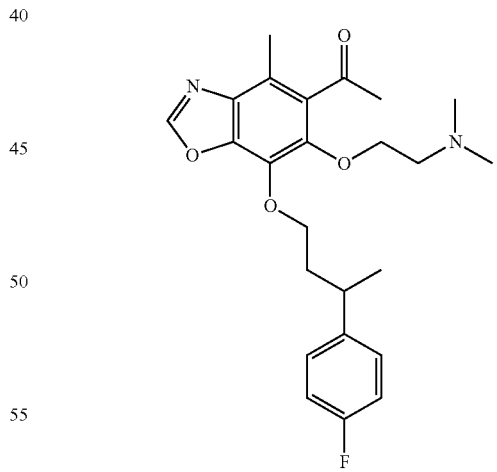

4b) 5-Acetyl-7-[3-(4-fluorophenyl)butoxy]-4-methyl-6-(2-N,N-dimethylamino-ethoxy)benzooxazole Example 4a) (46 mg, 0.10 mmol) was reacted with 2.0M N,N-dimethylamine in THF as described under General Procedure E. The crude produced was purified by preparative TLC to give the title compound (16 mg, 32%) as pale oil. $^1$H NMR (300 MHz, CDCl$_3$) δ 7.96 (s, 1H), 7.21-7.16 (m, 2H), 7.02-6.95 (m, 2H), 4.31-4.22 (m, 2H), 4.08 (t, J=6.0 Hz, 2H), 3.56 (t, J=6.3 Hz, 2H), 3.10-3.02 (m, 1H), 2.63 (t, J=5.4 Hz, 2H), 2.55 (s, 3H), 2.42 (s, 3H), 2.30 (s, 6H), 2.16-1.95 (m, 2H), 1.31 (d, J=6.9 Hz, 3H), MS (ES⁺) m/z 429.2 (M+H⁺).

Example 5

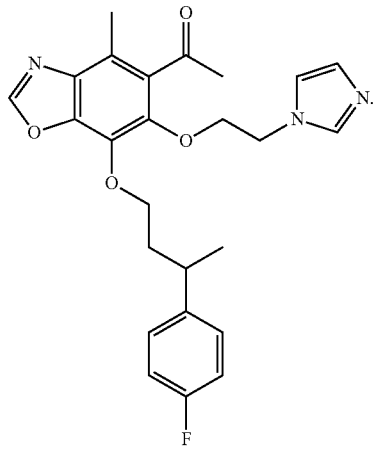 [SMILES: CC(=O)c1c(OCCn2ccnc2)c(OCCC(C)c2ccc(F)cc2)c2ocnc2c1C]

5-Acetyl-7-[3-(4-fluorophenyl)butoxy]-4-methyl-6-(2-N-imidazolyl-ethoxy)benzooxazole Example 4a) (46 mg, 0.10 mmol) was reacted with imidazole (68 mg, 1.0 mmol) as described under General Procedure E to give the title compound (40 mg, 89%) as a yellow oil. $^1$H NMR (300 MHz, CDCl$_3$) δ 7.97 (s, 1H), 7.57 (bs, 1H), 7.16-7.09 (m, 3H), 7.00-6.94 (m, 3H), 4.22 (s, 4H), 4.20-4.12 (m, 2H), 2.97-2.90 (m, 1H), 2.40 (s, 3H), 2.38 (s, 3H), 2.00-1.89 (m, 2H), 1.29 (d, J=6.9 Hz, 3H), ESIMS m/z [M+H]⁺ 452.2.

Example 6c

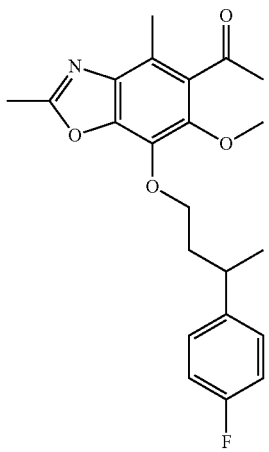

6a 5-Acetyl-7-[3-(4-fluorophenyl)butoxy]-6-methoxy-2,4-dimethylbenzooxazole

Example 2b) (4.16 g, 11.5 mmol) was treated as described for Example 1f) but with triethyl orthoacetate (22.13 g, 140 mmol) at 90° C. for 3 h. The crude residue was purified by flash chromatography (silica gel, Et$_2$O/hexane, 2:3) to give the title compound (3.71 g, 83%) as an oil. $^1$H NMR (300 MHz, CDCl$_3$) δ 7.21-7.17 (m, 2H), 7.01-6.95 (m, 2H), 4.31-4.12 (m, 2H), 3.85 (s, 3H), 3.14-3.02 (m, 1H), 2.59 (s, 3H), 2.51 (s, 3H), 2.38 (s, 3H), 2.18-2.03 (m, 2H), 1.33 (d, J=6.3 Hz, 3H), ESIMS m/z [M+H]⁺ 386.2.

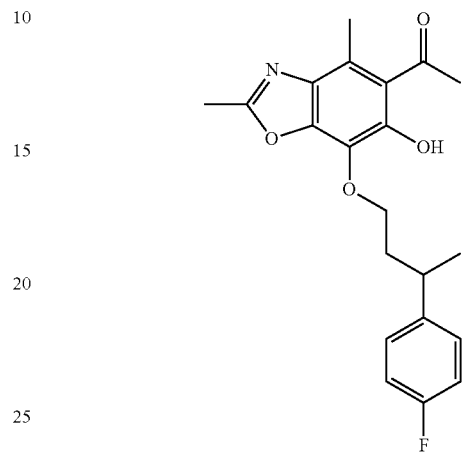

6b) 5-Acetyl-7-[3-(4-fluorophenyl)butoxy]-6-hydroxy-2,4-dimethylbenzooxazole

Example 6a) (312 mg, 0.81 mmol) was reacted as described under General Procedure C to give the title compound (300 mg, 100%). $^1$H NMR (300 MHz, CDCl$_3$) δ 10.69 (s, 1H), 7.21-7.16 (m, 2H), 7.00-6.94 (m, 2H), 4.29-4.10 (m, 2H), 3.13-3.01 (m, 1H), 2.68 (s, 6H), 2.60 (s, 3H), 2.38 (s, 3H), 2.17-1.93 (m, 2H), 1.31 (d, J=6.9 Hz, 3H), ESIMS m/z [M+H]⁺ 372.3.

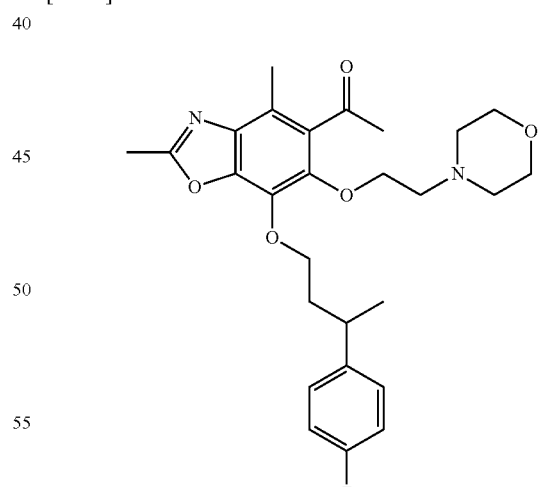

6c) 5-Acetyl-7-[3-(4-fluorophenyl)butoxy]-2,4-dimethyl-6-(2-morpholin-4-yl-ethoxy)-benzooxazole Example 6b) (77 mg, 0.21 mmol) was reacted with 2-(2-chloroethyl)morpholine as described under General Procedure F (room temperature for 2.5 d) to give the title compound (45 mg, 47%) as a yellow oil. $^1$H NMR (300 MHz, CDCl$_3$) δ

7.26-7.15 (m, 2H), 7.01-6.95 (m, 2H), 4.27-4.15 (m, 2H), 4.08 (t, J=5.7 Hz, 2H), 3.73 (t, J=4.5 Hz, 2H), 3.10-3.03 (m, 1H), 2.67 (t, J=5.7 Hz, 2H), 2.58 (s, 3H), 2.55 (s, 3H), 2.52-2.50 (m, 4H), 2.37 (s, 3H), 2.12-1.95 (m, 2H), 1.32 (d, J=7.2 Hz, 3H), ESIMS m/z [M+H]+ 485.2.

Example 7

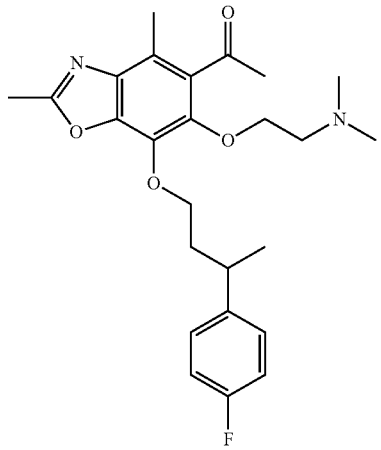

5-Acetyl-6-(2-dimethylaminoethoxy)-7-[3-(4-fluorophenyl)butoxy]-2,4-dimethyl-benzooxazole Example 6b) (65 mg, 0.18 mmol) was reacted with 2-chloroethyldimethylamine as described under General Procedure F (room temperature, 1 d) to give the title compound (34 mg, 42%) as a brown oil. $^1$H NMR (300 MHz, CDCl$_3$) δ 7.26-7.17 (m, 2H), 7.01-6.95 (m, 2H); 4.27-4.18 (m, 2H); 4.08 (t, J=6.0 Hz, 2H), 3.09-3.04 (m, 1H), 2.62 (t, J=6.0 Hz, 2H), 2.58 (s, 3H), 2.54 (s, 3H), 2.37 (s, 3H), 2.30 (s, 6H), 2.14-1.99 (m, 2H), 1.31 (d, J=6.9 Hz, 3H), ESIMS m/z [M+H]+ 443.2.

Example 8

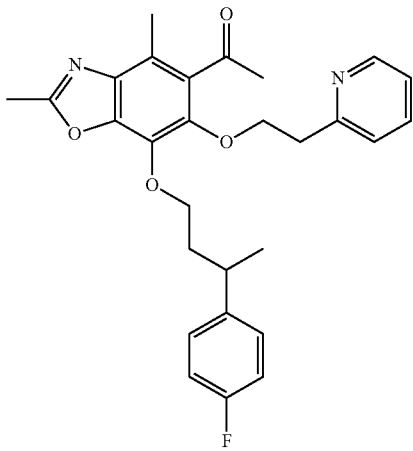 [SMILES: CC(=O)c1c(OCCc2ccccn2)c(OCCC(C)c2ccc(F)cc2)c2oc(C)nc2c1C]

5-Acetyl-7-[3-(4-fluorophenyl)butoxy]-2,4-dimethyl-6-(2-pyridin-2-yl-ethoxy)-benzooxazole Example 6b) (77 mg, 0.21 mmol) was reacted with 2-(2-mesylethyl)pyridine as described under General Procedure D to give the title compound (13 mg, 13%) as a yellow oil. $^1$H NMR (CDCl$_3$): δ 8.55 (m, 1H), 7.63-7.61 (td, J=7.8, 1.8 Hz, 1H), 7.26 (s, 1H), 7.24-7.14 (m, 3H), 6.99-6.93 (m, 2H), 4.41 (t, J=6.6 Hz, 2H), 4.21-4.10 (m, 2H), 3.19 (t, J=6.6 Hz, 2H), 3.03-2.99 (m, 1H), 2.57 (s, 3H), 2.34 (s, 3H), 2.32 (s, 3H), 2.07-1.92 (m, 2H), 1.29 (d, J=6.9 Hz, 3H), ESIMS m/z [M+H]+ 477.2.

Example 9

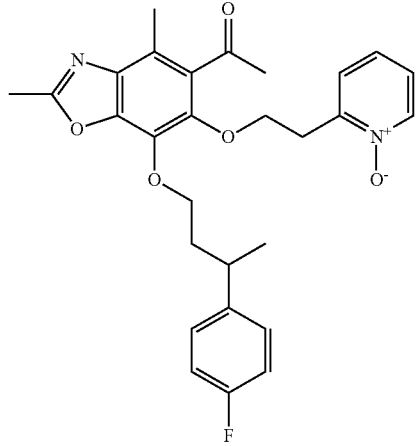 [SMILES: CC(=O)c1c(OCCc2cccc[n+]2[O-])c(OCCC(C)c2ccc(F)cc2)c2oc(C)nc2c1C]

2-(2-(5-acetyl-7-(3-(4-fluorophenyl)butoxy)-2,4-dimethylbenzo[d]oxazol-6-yloxy)ethyl)pyridine 1-oxide To a stirred solution of Example 8) (24 mg, 0.05 mmol) in acetic acid (0.5 mL) at room temperature was added H$_2$O$_2$ (30% aq.) and the solution heated to 100° C. for 23 h. The acetic acid was removed in vacuo and the brown oil partitioned between NaHCO$_3$ (20 mL) and EtOAc (20 mL). The aqueous phase (pH=10) was extracted with EtOAc (2×10 mL). The combined extracts were dried (MgSO$_4$) and concentrated in vacuo. The product was purified by column chromatography (silica gel, hexane/Et$_2$O (1:4) to Et$_2$O to MeOH/DCM (1:19)). The title compound (10 mg, 41%) eluted from the column with MeOH/DCM (1:19) as a pale yellow oil. $^1$H NMR (CDCl$_3$): δ 8.26-8.24 (m, 1H), 7.41-7.38 (m, 1H), 7.21 (m, 4H), 7.00-6.94 (m, 2H), 4.44 (t, J=6 Hz, 2H), 4.22-4.15 (m, 2H), 3.32 (t, J=6 Hz, 2H), 3.05-2.95 (m, 1H), 2.57 (s, 3H), 3.37 (s, 3H), 2.34 (s, 3H), 2.10-1.90 (m, 2H), 1.30 (d, J=6.9 Hz, 3H), ESIMS m/z [M+H]+ 493.2.

Example 10b

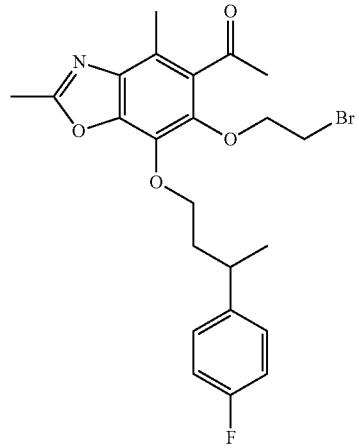 [SMILES: CC(=O)c1c(OCCBr)c(OCCC(C)c2ccc(F)cc2)c2oc(C)nc2c1C]

10a) 5-Acetyl-6-(2-bromoethoxy)-7-[3-(4-fluorophenyl)butoxy]-2,4-dimethyl-benzooxazole Example 6b) (79 mg, 0.21 mmol) was reacted with dibromoethane (350 μL, excess) as described under General Procedure D to give the title compound (76 mg, 82%) as a pale oil, which was used in the next step without purification. ¹H NMR (300 MHz, CDCl₃) δ 7.22-7.17 (m, 2H), 7.01-6.96 (m, 2H), 4.28 (t, J=6.3 Hz, 2H), 4.22-4.18 (m, 2H), 3.55 (t, J=6.3 Hz, 2H), 3.15-3.02 (m, 1H), 2.59 (s, 3H), 2.54 (s, 3H), 2.38 (s, 3H), 2.18-1.95 (m, 4H), 1.32 (d, J=6.9 Hz, 3H), ESIMS m/z [M+H]⁺ 478.3.

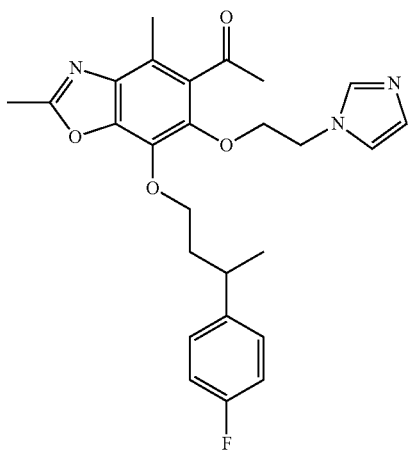 [SMILES: CC(=O)c1c(OCCn2ccnc2)c(OCCC(C)c2ccc(F)cc2)c2oc(C)nc2c1C]

10b) 5-Acetyl-7-[3-(4-fluorophenyl)butoxy]-6-(2-imidazol-1-yl-ethoxy)-2,4-dimethyl-benzooxazole Example 10a) (100 mg, 0.21 mmol) was reacted with imidazole (153 mg, 2.25 mmol) as described under General Procedure E to give the title compound (40 mg, 41%) as a yellow oil. ¹H NMR (300 MHz, CDCl₃) δ 7.60 (s, 1H), 7.26-7.01 (m, 2H), 7.09 (s, 2H), 7.00-6.94 (m, 2H), 4.21 (s, 4H), 4.15-4.09 (m, 2H), 3.00-2.90 (m, 1H), 2.58 (s, 3H), 2.38 (s, 3H), 2.36 (s, 3H); 2.00-1.89 (m, 2H), 1.29 (d, J=6.9 Hz, 3H), ESIMS m/z [M+H]⁺ 466.2.

Examples 11a and 11b

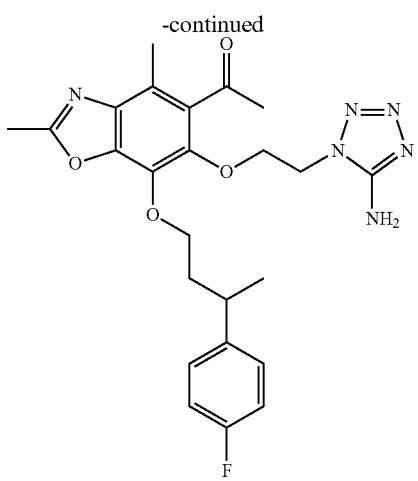

11a) 5-Acetyl-6-[2-(5-aminotetrazol-2-yl)-ethoxy]-7-[3-(4-fluorophenyl)butoxy]-2,4-dimethyl-benzooxazole and 11b) 5-Acetyl-6-[2-(5-amino-tetrazol-1-yl)-ethoxy]-7-[3-(4-fluorophenyl)butoxy]-2,4-dimethyl-benzooxazole Example 10a) (100 mg, 0.21 mmol) was reacted with 5-aminotetrazole (36 mg, 0.42 mmol) as described under General Procedure E. The crude product was purified by flash chromatography (silica gel, CH₂Cl₂/EtOAc, 7:3) to give Example 11a) (26 mg, 29%) as a pale oil. Further elution (silica gel, CH₂Cl₂/EtOAc 4:6) gave Example 11b) (23 mg, 21%) as a pale oil.

11b)—¹H NMR (300 MHz, CDCl₃) δ 7.16-7.12 (m, 2H), 7.01-6.95 (m, 2H), 5.04 (s, 2H), 4.46-4.36 (s, 4H), 4.18-4.13 (m, 2H), 2.90-2.80 (m, 1H), 2.56 (s, 3H), 2.45 (s, 3H), 2.37 (s, 3H); 1.95-1.86 (m, 2H), 1.29 (d, J=6.9 Hz, 3H), ESIMS m/z [M+H]⁺ 483.3.

11a)—¹H NMR (300 MHz, CDCl₃) δ 7.21-7.16 (m, 2H), 7.02-6.96 (m, 2H), 4.71 (t, J=5.1 Hz, 2H), 4.44 (t, J=5.1 Hz, 2H), 4.30 (s, 2H), 4.21-4.14 (s, 2H), 4.18-4.13 (m, 2H), 3.01-2.90 (m, 1H), 2.58 (s, 3H), 2.38 (s, 3H), 2.35 (s, 3H); 2.07-1.95 (m, 2H), 1.32 (d, J=6.9 Hz, 3H), ESIMS m/z [M+H]⁺ 483.3.

Example 12

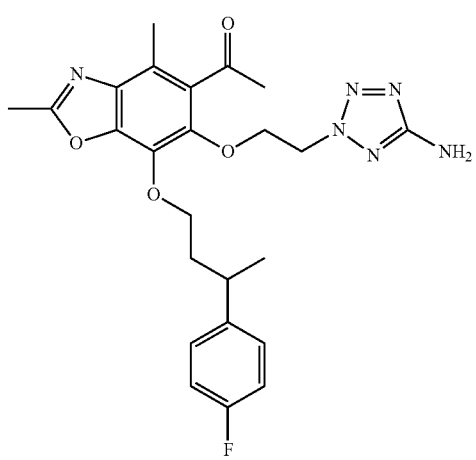

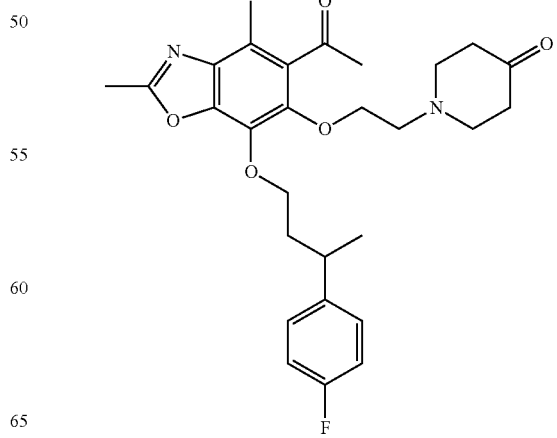

1-(2-{5-Acetyl-7-[3-(4-fluorophenyl)butoxy]-2,4-dimethyl-benzooxazol-6-yloxy}-ethyl)-piperidin-4-one Example 10a) (120 mg, 0.25 mmol) was reacted with piperidone (15 eq.) as described under General Procedure E to give the title compound. (80 mg, 66%) as a yellow oil. $^1$H NMR (300 MHz, CDCl$_3$) δ 7.21-7.16 (m, 2H), 7.01-6.96 (m, 2H); 4.28-4.20 (m, 2H); 4.12 (t, J=5.7 Hz, 2H), 3.10-3.00 (m, 1H), 2.84-2.77 (m, 6H), 2.59 (s, 3H), 2.56 (s, 3H), 2.47 (t, J=6.3 Hz, 4H), 2.11-1.99 (m, 2H), 1.32 (d, J=7.2 Hz, 3H), ESIMS m/z [M+H]$^+$ 497.5.

Example 13

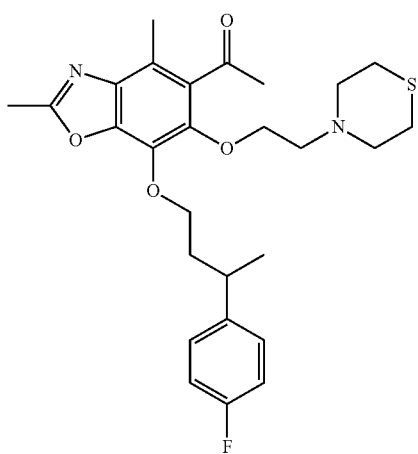 [SMILES: CC(=O)c1c(OCCN2CCSCC2)c(OCCC(C)c2ccc(F)cc2)c2oc(C)nc2c1C]

4-Acetyl-7-[3-(4-fluorophenyl)butoxy]-6-2,4-dimethyl-6-(2-thiomorpholin-4-ylethoxy)-benzooxazole Example 10a) (110 mg, 0.23 mmol) was reacted with thiomorpholine (15 eq.) as described under General Procedure E to give the title compound (82 mg, 72%) as a yellow oil. $^1$H NMR (300 MHz, CDCl$_3$) δ 7.20-7.16 (m, 2H), 7.02-6.95 (m, 2H); 4.29-4.15 (m, 2H); 4.04 (t, J=5.4 Hz, 2H), 3.10-3.02 (m, 1H), 2.79-2.75 (m, 4H), 2.71-2.66 (m, 4H), 2.58 (s, 3H), 2.57 (s, 3H), 2.38 (s, 3H), 2.13-1.71 (m, 2H), 1.32 (d, J=6.9 Hz, 3H) ES IMS m/z [M+H]$^+$ 501.2.

Example 14

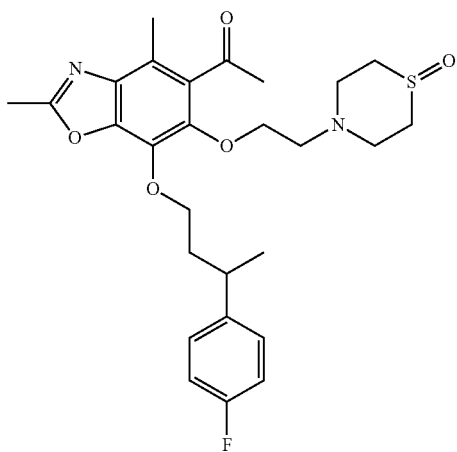 [SMILES: CC(=O)c1c(OCCN2CCS(=O)CC2)c(OCCC(C)c2ccc(F)cc2)c2oc(C)nc2c1C]

5-Acetyl-7-[3-(4-fluorophenyl)butoxy]-2,4-dimethyl-6-[2-(1-oxo-thiomorpholin-4-yl)-ethoxy]-benzooxazole Example 10a) (82 mg, 0.17 mmol) was reacted with the trifluoroacetate salt of 1-oxothiomorpholine as described under General Procedure D to give the title compound (16 mg, 18%) as a yellow oil. $^1$H NMR (300 MHz, CDCl$_3$) δ 7.20-7.16 (m, 2H), 7.01-6.95 (m, 2H); 4.27-4.19 (m, 2H); 4.08 (t, J=5.4 Hz, 2H), 3.16-3.00 (m, 3H), 2.86-2.82 (m, 4H), 2.78-2.72 (m, 4H), 2.58 (s, 3H), 2.53 (s, 3H), 2.36 (s, 3H), 2.31-1.90 (m, 2H), 1.32 (d, J=6.0 Hz, 3H), ESIMS m/z [M+H]$^+$ 517.3.

Example 15

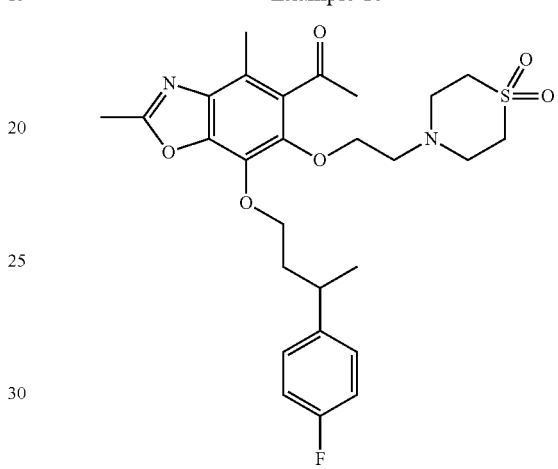

5-Acetyl-6-[2-(1,1-dioxo-thiomorpholin-4-yl)-ethoxy]-7-[3-(4-fluorophenyl)butoxy]-2,4-dimethyl-benzooxazole Example 10a) (142 mg, 0.30 mmol) was reacted with the trifluoroacetate salt of 1,1-dioxothiomorpholine as described under General Procedure D to give the title compound (37 mg, 23%) as a brown oil. $^1$H NMR (300 MHz, CDCl$_3$) δ 7.20-7.16 (m, 2H), 7.01-6.96 (m, 2H); 4.27-4.20 (m, 2H); 4.07 (t, J=5.4 Hz, 2H), 3.05 (s, 8H), 2.80 (t, J=5.4 Hz, 2H), 2.58 (s, 3H), 2.52 (s, 3H), 2.37 (s, 3H), 2.30-1.90 (m, 2H), 1.32 (d, J=6.9 Hz, 3H), ESIMS m/z [M+H]$^+$ 533.3.

Example 16

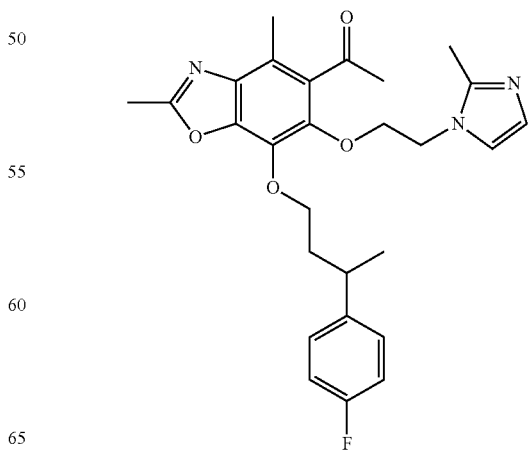

5-Acetyl-7-[3-(4-fluorophenyl)butoxy]-2,4-dimethyl-6-[2-(2-methylimidazol-1-yl)-ethoxy]-benzooxazole Example 10a) (112 mg, 0.23 mmol) was reacted with 2-methylimidazole (210 mg, 2.55 mmol) as described under General Procedure E to give the title compound (86 mg, 78%) as a light brown oil. $^1$H NMR (300 MHz, CDCl$_3$) δ 7.60-7.12 (m, 2H), 7.00-6.90 (m, 4H), 4.20-4.05 (m, 6H), 3.02-2.90 (m, 1H), 2.58 (s, 3H), 2.41 (s, 3H), 2.36 (s, 3H); 2.35 (s, 3H), 2.00-1.89 (m, 2H), 1.29 (d, J=7.2 Hz, 3H), ESIMS m/z [M+H]$^+$ 480.2.

Example 17a and 17b

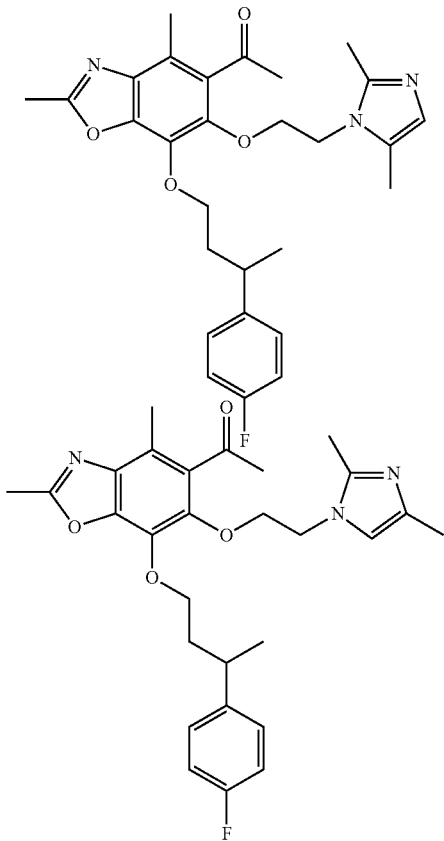

5-Acetyl-6-[2-(2,5-dimethyl-imidazol-1-yl)-ethoxy]-7-[3-(4-fluorophenyl)butoxy]-2,4-dimethyl-benzooxazole 17a and 5-Acetyl-6-[2-(2,4-dimethyl-imidazol-1-yl)-ethoxy]-7-[3-(4-fluorophenyl)butoxy]-2,4-dimethyl-benzooxazole 17b Example 10a) (98 mg, 0.20 mmol) was reacted with 2,4-dimethylimidazole (195 mg, 2.03 mmol) as described under General Procedure E to give a 1:4 mixture of regioisomers 17a and 17b as a light brown oil (69 mg, 70%). $^1$H NMR (300 MHz, CDCl$_3$) δ 7.16-7.12 (m, 2H), 6.99-6.94 (m, 2H), 6.64 (s, 0.2H), 6.60 (m, 0.8H), 4.17-4.03 (m, 6H), 2.98-2.95 (m, 1H), 2.57 (s, 3H), 2.36 (s, 3H), 2.36 (s, 3H), 2.36 (s, 3H), 2.35 (s, 3H), 2.16 (d, J=1.2 Hz, 2H), 1.29 (d, J=6.9 Hz, 3H), ESIMS m/z [M+H]$^+$ 494.2.

Example 18

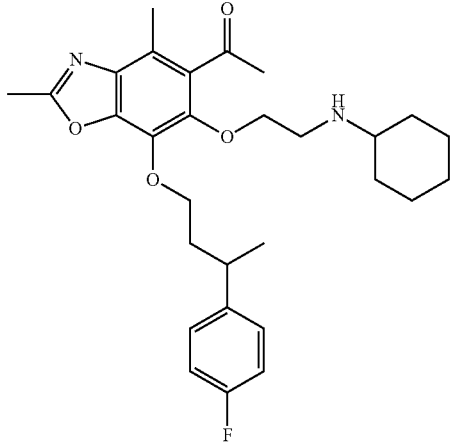 [SMILES: CC(=O)c1c(OCCNC2CCCCC2)c(OCCC(C)c2ccc(F)cc2)c2oc(C)nc2c1C]

5-Acetyl-6-(2-cyclohexylamino-ethoxy)-7-[3-(4-fluorophenyl)butoxy]-2,4-dimethyl-benzooxazole Example 10a) (129 mg, 0.27 mmol) was reacted with cyclohexylamine (303 mg, 3.07 mmol) as described under General Procedure E to give the title compound (111 mg, 83%) as a light yellow oil. $^1$H NMR (300 MHz, CDCl$_3$) δ 7.21-7.17 (m, 2H), 7.00-6.95 (m, 2H), 4.28-4.13 (m, 2H), 4.10 (t, J=5.4 Hz, 2H), 3.10-3.00 (m, 1H), 2.91 (t, J=5.4 Hz, 2H), 2.58 (s, 3H), 2.53 (s, 3H), 2.37 (s, 3H), 2.18-1.95 (m, 2H), 1.85-1.50 (m, 8H), 1.31 (d, J=7.2 Hz, 3H), 1.18-1.10 (m, 4H), ESIMS m/z [M+H]$^+$ 497.5.

Example 19

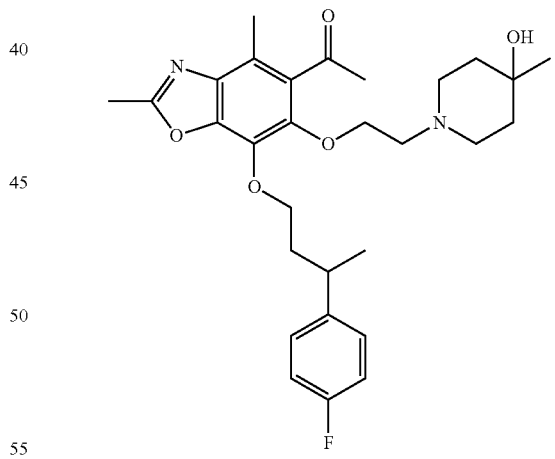

5-Acetyl-7-[3-(4-fluorophenyl)butoxy]-6-[2-(4-hydroxy-4-methyl-piperidin-1-yl)-ethoxy]-2,4-dimethyl-benzooxazole Example 10a) (102 mg, 0.21 mmol) was reacted with the trifluoroacetate salt of 4-methylpiperidin-4-ol (4 eq.) as described under General Procedure E to give the title compound (46 mg, 42%) as a light yellow oil. $^1$H NMR (300 MHz, CDCl$_3$) δ 7.21-7.17 (m, 2H), 7.01-6.95 (m, 2H), 4.28-4.13 (m, 2H), 4.10 (t, J=5.7 Hz, 2H), 3.21-3.10 (m, 1H), 2.75-2.4

(m, 4H), 2.57 (s, 3H), 2.54 (s, 3H), 2.37 (s, 3H), 2.10-1.95 (m, 2H), 1.80-1.54 (m, 4H), 1.32 (d, J=6.9 Hz, 3H), 1.25 (s, 3H), ESIMS m/z [M+H]⁺ 513.5.

Example 20

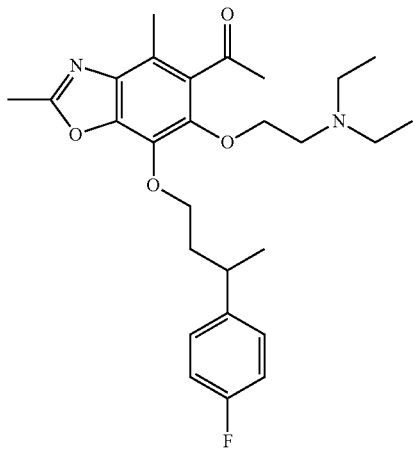 [SMILES: CCN(CC)CCOc1c(C(C)=O)c(C)c2nc(C)oc2c1OCCC(C)c1ccc(F)cc1]

5-Acetyl-6-(2-diethylamino-ethoxy)-7-[3-(4-fluorophenyl)butoxy]-2,4-dimethyl-benzooxazole Example 10a) (110 mg, 0.23 mmol) was reacted with diethylamine (15 eq.) as described under General Procedure E to give the title compound (83 mg, 83%) as a light yellow oil. ¹H NMR (300 MHz, CDCl₃) δ 7.21-7.16 (m, 2H), 7.00-6.95 (m, 2H), 4.30-4.12 (m, 2H), 4.06 (t, J=6.6 Hz, 2H), 3.02-3.14 (m, 1H), 2.79 (t, J=6.6 Hz, 2H), 2.58 (q, J=7.2 Hz, 4H), 2.58 (s, 3H), 2.53 (s, 3H), 2.37 (s, 3H), 2.11-1.98 (m, 2H), 1.31 (d, J=6.9 Hz, 3H), 1.03 (t, J=7.2 Hz, 6H), ESIMS m/z [M+H]⁺ 471.5.

Example 21

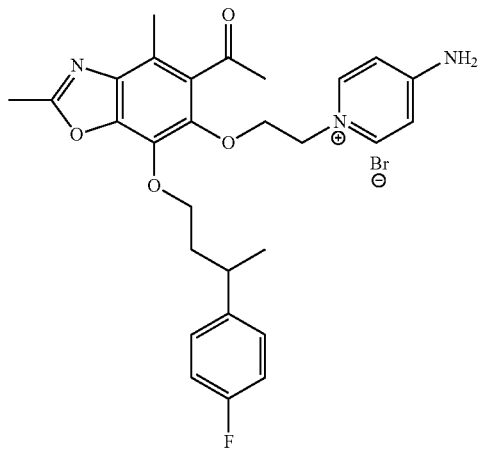 [SMILES: CC(=O)c1c(OCC[n+]2ccc(N)cc2)c(OCCC(C)c2ccc(F)cc2)c2oc(C)nc2c1C ; [Br-]]

5-Acetyl-6-(2-(4-aminopyridin-1-ium)ethoxy)-7-[3-(4-fluorophenyl)butoxy]-2,4-dimethyl-benzo[d]oxazole chloride Example 10a) (98 mg, 0.21 mmol) was reacted with p-aminopyridine (5 eq.) as described under General Procedure E to give the title compound (16 mg, 16%) as a white solid. ¹H NMR (300 MHz, CDCl₃) δ 8.48 (br s, 1H), 7.96 (br d, J=6.3 Hz, 2H), 7.25 (br d, J=6.3 Hz, 2H), 7.17-7.16 (m, 2H), 7.00- 6.95 (m, 2H), 4.48 (m, 2H), 4.27 (m, 2H), 4.17 (t, J=6.9 Hz, 2H), 2.98-2.86 (m, 1H), 2.55 (s, 3H), 2.32 (s, 3H), 2.30 (s, 3H), 2.17-1.83 (m, 3H) 1.29 (d, J=7.2 Hz, 3H), ESIMS m/z [M-Br]⁺ 492.3.

Example 22b

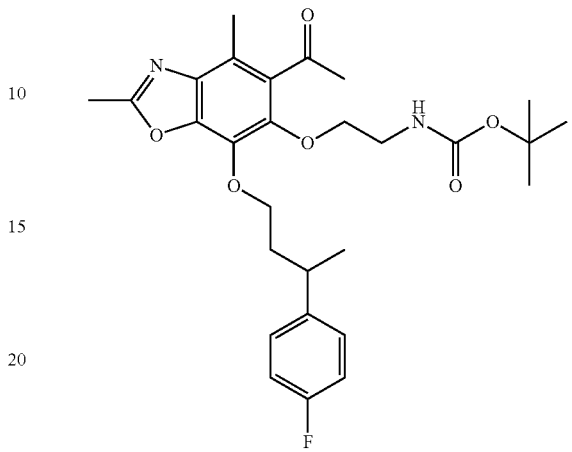

22a) 5-Acetyl-6-(2-(N-Boc-amino)ethoxy)-7-(3-(4-fluorophenyl)butoxy)-2,4-dimethylbenzo[d]oxazole To a solution of Example 6b) (50 mg, 0.14 mmol), triphenylphosphine (46 mg, 0.18 mmol) and tert-butyl N-(2-hydroxyethyl)carbamate (29 mg, 0.18) in toluene (2 mL) was added diisopropylazodicarboxylate (34 uL, 0.18 mmol). After 1.5 h, water (10 mL) was added and the mixture extracted with chloroform (50 mL). The organic phase was dried (Na₂SO₄), filtered and the solvent removed in vacuo. The product was purified by flash chromatography (neutral alumina, EtOAc/hexane 2:8) to give the title compound (52 mg, 74%). ¹H NMR (300 MHz, CDCl₃) δ 7.20-7.15 (m, 2H), 7.00-6.94 (m, 2H), 5.20 (br m, 1H), 4.23 (m, 2H), 4.05 (br t, J=5 Hz, 2H), 3.39 (app q, J=5 Hz, 2H), 3.42 (m, 1H), 2.57 (s, 3H), 2.50 (s, 3H), 2.37 (s, 3H), 2.15-1.96 (br m, 2H), 1.43 (s, 9H), 1.32 (d, J=7 Hz, 3H), ESIMS m/z [M+H (-Boc)]⁺ 415.3.

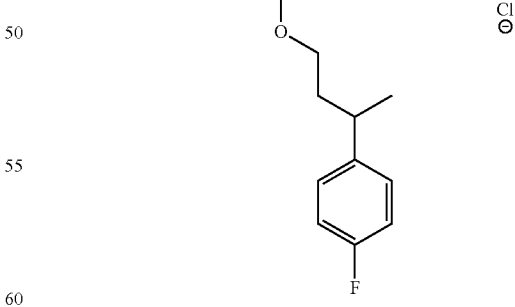

22b) 5-Acetyl-6-(2-aminiumethoxy)-7-[3-(4-fluorophenyl)butoxy]-2,4-dimethyl-benzo[d]oxazole chloride Example 22a) (42 mg, 0.08 mmol) was treated with a 3 M HCl solution (1 mL), prepared by addition of acetyl chloride (4.2 mL) to methanol (15.8 ml). The reaction mixture was stirred for 0.5 h and the volatiles removed to give the title compound (36 mg, quantitative). $^1$H NMR (300 MHz, CDCl$_3$) δ 8.50 (br s, 3H), 7.20-7.15 (m, 2H), 7.00-6.94 (m, 2H), 4.41 (br s, 2H), 4.27 (br m, 2H), 3.32 (br s, 2H), 2.98 (br m, 1H), 2.62 (s, 3H), 2.54 (s, 3H), 2.40 (s, 3H), 2.17-2.01 (br m, 2H), 1.31 (d, J=7 Hz, 3H), ESIMS m/z [M-Cl]$^+$ 415.3.

Example 23

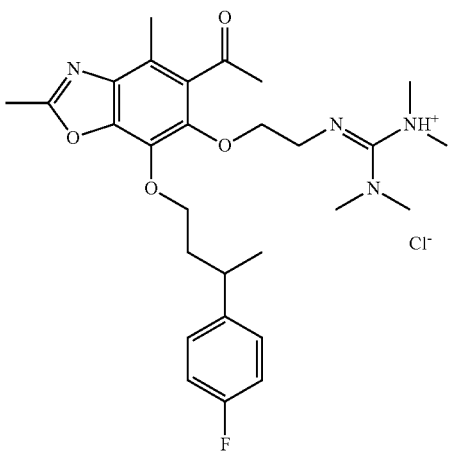

5-Acetyl-6-(2-(N,N,N',N'-tetramethylguanidinium) ethoxy)-7-[3-(4-fluorophenyl)butoxy]-2,4-dimethyl-benzo[d]oxazole chloride To a solution of Example 10a) (170 mg, 0.36 mmol) in dry dimethylformamide (3 ml) was added sodium azide and the reaction was stirred at 60° C. under a N$_2$ atmosphere until the reaction was complete by TLC and LCMS (2 h). The reaction was quenched with NH$_4$Cl$_{(aq.)}$ (sat.) and extracted with EtOAc. The organic layer was washed with water, then brine, dried over MgSO$_4$ and concentrated in vacuo. The crude residue was dissolved in ethyl acetate (20 ml), followed by addition of 10% Pd on charcoal and the reaction mixture was stirred under balloon pressure of H$_2$ gas until the reaction was complete by TLC and LCMS (2 h). The reaction mixture was filtered through small celite plug into a reaction vessel. Triethylamine (0.3 mL) and 2-chloro-N,N,N',N'-tetramethylguanidinium hydrochloride (192 mg, 1.42 mmol) were added to the filtrate and stirred at room temperature for 2 h. The reaction was quenched with NH$_4$Cl$_{(aq.)}$ (sat.) and extracted with ethyl acetate. The organic layer was washed with water, then brine, dried over MgSO$_4$ and concentrated in vacuo. The crude was purified by preparative TLC (silica gel, EtOAc/DCM 1:1) to give the title compound (22 mg, 12%) as a light brown oil. $^1$H NMR (300 MHz, CDCl$_3$) δ 9.73 (bs, 1H), 7.23-7.18 (m, 2H), 7.00-6.95 (m, 2H), 4.47 (t, J=4.5 Hz, 2H), 4.25 (t, J=6.6 Hz, 2H), 3.47 (bq, 2H), 3.08-2.91 (m, 13H), 2.57 (s, 3H), 2.44 (s, 3H), 2.33 (s, 3H); 2.22-1.89 (m, 2H), 1.33 (d, J=6.9 Hz, 3H), ESIMS m/z [M+H]$^+$ 513.2.

Example 24b

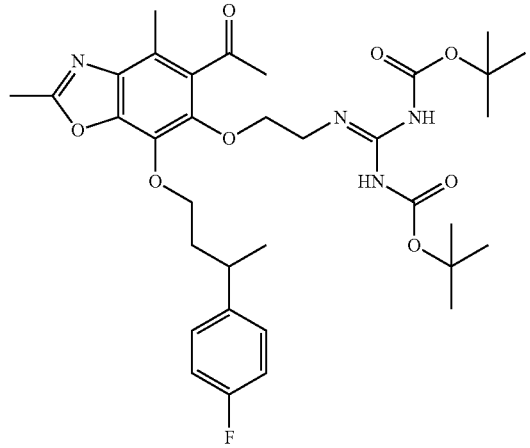 [SMILES: CC(=O)c1c(OCCN=C(NC(=O)OC(C)(C)C)NC(=O)OC(C)(C)C)c(OCCC(C)c2ccc(F)cc2)c2oc(C)nc2c1C]

24a) 5-Acetyl-6-(2-(N,N'-di-Boc-guanidino)ethoxy)-7-[3-(4-fluorophenyl) butoxy]-2,4-dimethyl-benzooxazole trifluoroacetate To a solution of Example 6b) (51 mg, 0.14 mmol), triphenylphosphine (46 mg, 0.18 mmol) and 1,3-di-Boc-2-(2-hydroxyethyl) guanidino (55 mg, 0.18 mmol) in toluene (2 mL) was added diisopropylazodicarboxylate (34 uL, 0.18 mmol). After 24 h, water (10 mL) was added and the mixture extracted with dichloromethane (50 mL). The organic phase was dried over Na$_2$SO$_4$, filtered and concentrated in vacuo. The product was purified by flash chromatography (neutral alumina, EtOAc/hexane 2:8) to give the title compound (44 mg, 50%). $^1$H NMR (300 MHz, CDCl$_3$) δ 11.53 (s, 1H), 8.74 (br m, 1H), 7.19-7.14 (m, 2H), 7.00-6.94 (m, 2H), 4.27-4.15 (m, 2H), 4.11 (t, J=5 Hz, 2H), 3.75 (app q, J=5 Hz, 2H), 3.02 (m, 1H), 2.57 (s, 3H), 2.52 (s, 3H), 2.36 (s, 3H), 2.09-1.95 (m, 2H), 1.50 (s, 9H), 1.48 (s, 9H), 1.30 (d, J=7 Hz, 3H), ESIMS m/z [M+H]$^+$ 657.5.

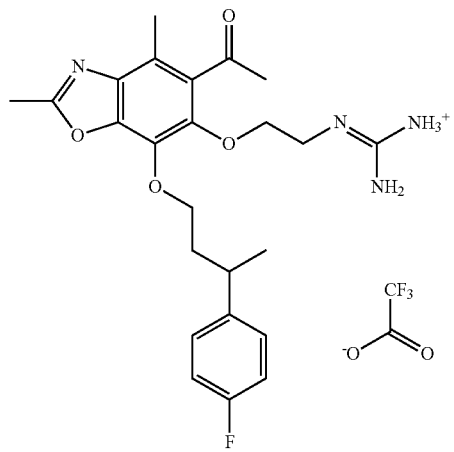

24b) 5-Acetyl-6-(2-(guanidinium)ethoxy)-7-[3-(4-fluorophenyl)butoxy]-2,4-dimethyl-benzooxazole trifluoroacetate Example 24a) (44 mg, 0.07 mmole) was treated with trifluoroacetic acid (1 mL) and DCM (1 mL) for 2 h. The volatiles were removed to give the title compound (38 mg, quantitative). ¹H NMR (300 MHz, CDCl₃) δ 7.91 (br s, 1H), 7.26-7.13 (br m, 4H), 7.00-6.91 (m, 2H), 4.72 (br s, 2H), 4.23 (t, J=6.5 Hz, 2H), 4.12 (br s, 2H), 3.48 (br s, 2H), 2.98 (m, 1H), 2.58 (s, 3H), 2.50 (s, 3H), 2.35 (s, 3H), 2.14-1.94 (m, 2H), 1.29 (d, J=7 Hz, 3H), ESIMS m/z [M-CF₃CO₂]⁺ 657.5.

Example 25

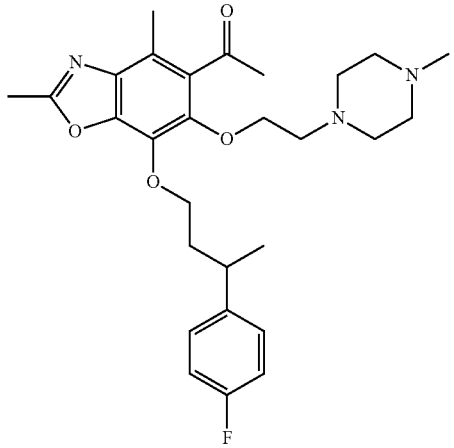

5-Acetyl-6-(2-(4-methylpiperidin-1-yl)ethoxy)-7-[3-(4-fluorophenyl)butoxy]-2,4-dimethyl-benzo[d]oxazole Example 10a) (110 mg, 0.23 mmol) was reacted with N-methyl piperidine (450 mg, 4.5 mmol) as described under General Procedure E to give the title compound (90 mg, 76%) as a yellow oil. ¹H NMR (300 MHz, CDCl₃) δ 7.21-7.16 (m, 2H), 7.00-6.95 (m, 2H), 4.25-4.18 (m, 2H), 4.08 (t, J=5.7 Hz, 2H), 3.10-3.02 (m, 1H), 2.70-2.28 (t+4s+bm, 22H), 2.15-1.94 (m, 2H), 1.29 (d, J=6.9 Hz, 3H), ESIMS m/z [M+H]⁺ 498.2.

Example 26

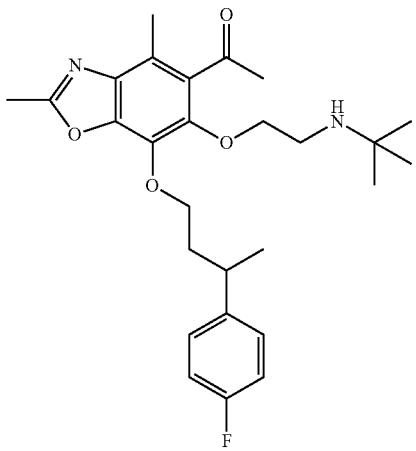 [SMILES: CC(=O)c1c(OCCNC(C)(C)C)c(OCCC(C)c2ccc(F)cc2)c2oc(C)nc2c1C]

5-Acetyl-6-(2-(N-tert butylamino)ethoxy)-7-[3-(4-fluorophenyl)butoxy]-2,4-dimethyl-benzo[d]oxazole Example 10a) (70 mg, 0.15 mmol) was reacted with t-butylamine (209 mg, 2.86 mmol) as described under General Procedure E to give the title compound (52 mg, 73%) as a light yellow oil. ¹H NMR (300 MHz, CDCl₃) δ 7.26-7.16 (m, 2H), 7.00-6.95 (m, 2H), 4.28-4.11 (m, 4H), 3.10-3.05 (m, 1H), 2.85 (t, J=6.6 Hz, 2H), 2.59 (s, 3H), 2.54 (s, 3H), 2.37 (s, 3H), 2.11-1.98 (m, 2H), 1.31 (d, J=6.9 Hz, 3H), 1.12 (s, 9H). ESIMS m/z [M+H]⁺ 471.3.

Example 27

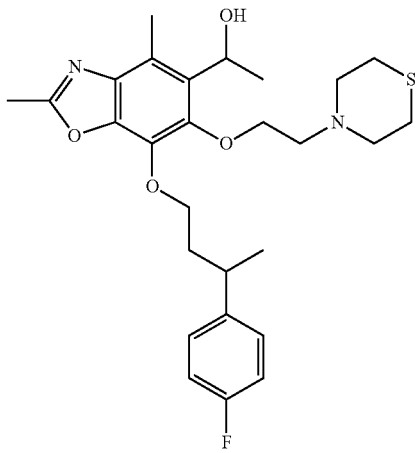 [SMILES: Cc1nc2c(C)c(C(C)O)c(OCCN3CCSCC3)c(OCCC(C)c3ccc(F)cc3)c2o1]

4-(1-Hydroxyethyl)-7-[3-(4-fluorophenyl)butoxy]-2,4-dimethyl-6-(2-thiomorpholin-4-ylethoxy)-benzo[d]oxazole Sodium borohydride (3 mg, 0.092 mmol) was added to a solution of Example 13) (42 mg, 0.084 mmol) in ethanol (2 mL) and the reaction mixture was heated at reflux for 2 h. Further sodium borohydride (3 mg, 0.092 mmol) was added and the reaction mixture was heated at reflux for 2 h. The reaction mixture was concentrated in vacuo and the resulting residue was partitioned over ethyl acetate/water. The organics were washed with water (2×10 mL), dried over MgSO₄ and concentrated in vacuo. The crude product was purified by flash chromatography (silica gel, EtOAc/CH₂Cl₂, 1:4) to give the title compound (12 mg, 29%). ¹H NMR (300 MHz, CDCl₃) δ 7.26-7.16 (m, 2H), 7.02-6.94 (m, 2H), 6.48 (bs, 1H), 5.14-5.08 (m, 1H), 4.62-4.56 (m, 1H), 4.27-4.13 (m, 2H), 3.87 (bs, 1H), 3.12-2.77 (m, 7H), 2.62-2.54 (m, 3H), 2.48 (s, 3H), 2.15-1.94 (m, 2H), 1.63-1.57 (m, 7H), 1.32 (d, J=6.9 Hz, 3H), ESIMS m/z [M+H]⁺ 503.3.2.

Example 28c

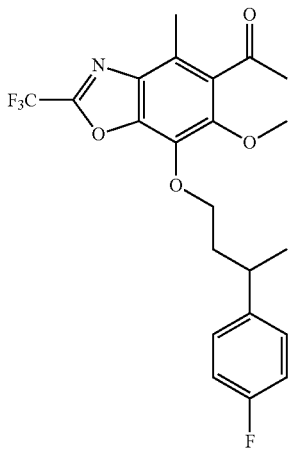

28a) 5-Acetyl-7-[3-(4-fluorophenyl)butoxy]-6-methoxy-4-methyl-2-trifluoromethyl-benzo[d]oxazole A solution of carbon tetrabromide (2.3 g, 6.9 mmol) in CH$_2$Cl$_2$ (1 mL) was added to a solution of Example 2b) (1g), trifluoroacetic acid (234 uL, 3.0 mmol), triphenylphosphine (2.18 g, 8.3 mmol) and triethylamine (1.92 mL, 13.9 mmol) in CH$_2$Cl$_2$ (20 mL) and the reaction mixture was stirred at room temperature for 6.5 h. The reaction mixture was partitioned over CH$_2$Cl$_2$ and water. The organics were dried over MgSO$_4$ and concentrated in vacuo. The crude product was purified by flash chromatography (silica gel, hexane/CH$_2$Cl$_2$, 1:1) to give the title compound (0.67 g, 55%). $^1$H NMR (300 MHz, CDCl$_3$) δ 7.25-7.16 (m, 2H), 7.01-6.95 (m, 2H), 4.30-4.19 (m, 2H), 3.90 (s, 3H), 3.13-3.06 (m, 1H), 2.51 (s, 3H), 2.44 (s, 3H), 2.14-2.03 (m, 2H), 1.33 (d, J=6.9 Hz, 3H), ESIMS m/z [M+H]$^+$ 440.2.

28b) 5-Acetyl-7-[3-(4-fluorophenyl)butoxy]-6-hydroxy-4-methyl-2-trifluoromethyl-benzooxazole Example 28a) (670 mg, 1.52 mmol) was reacted as described under General Procedure C to give the title compound (659 mg, 100%). $^1$H NMR (300 MHz, CDCl$_3$) δ 9.80 (s, 1H), 7.21-7.15 (m, 2H), 7.02-6.95 (m, 2H), 4.33-4.15 (m, 2H), 3.13-3.02 (m, 1H), 2.70 (s, 3H), 2.69 (s, 3H), 2.20-1.95 (m, 2H), 1.33 (d, J=6.9 Hz, 3H), ESIMS m/z [M+H]$^+$ 426.2.

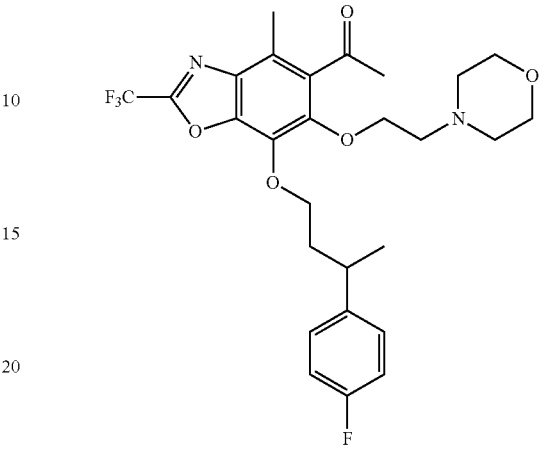

28c) 5-Acetyl-7-[3-(4-fluorophenyl)butoxy]-4-methyl-6-(2-morpholin-4-yl-ethoxy)-2-trifluoromethyl-benzooxazole Example 28b) (106 mg, 0.25 mmol) was reacted with 2-(2-chloroethyl)morpholine as described under General Procedure F to give the title compound (19 mg, 14%) as a brown oil. $^1$H NMR (300 MHz, CDCl$_3$) δ 7.21-7.16 (m, 2H), 7.01-6.95 (m, 2H); 4.32-4.15 (m, 2H); 4.13 (t, J=5.7 Hz, 2H), 3.72 (t, J=5.1 Hz, 2H), 3.10-3.03 (m, 1H), 2.70 (t, J=5.7 Hz, 2H), 2.60 (s, 3H), 2.52-2.49 (m, 4H), 2.43 (s, 3H), 2.15-1.97 (m, 2H), 1.33 (d, J=6.9 Hz, 3H), ESIMS m/z [M+H]$^+$ 539.2.

Example 29

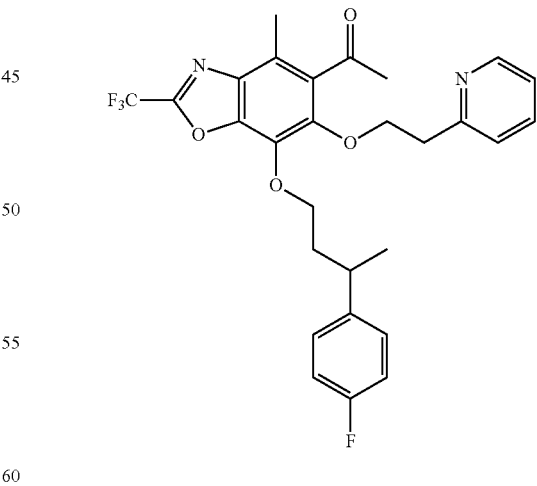

5-Acetyl-7-[3-(4-fluorophenyl)butoxy]-4-methyl-6-(2-pyridin-2-yl-ethoxy)-2-trifluoromethyl-benzo[d]oxazole 2-(2-Hydroxyethyl)-pyridine (38 mg, 0.31 mmol), PPh$_3$ (78 mg, 0.30 mmol) and diisopropylazodicarboxylate (61 mg, 0.30 mmol) were added to a solution of Example 28b) (99 mg, 023 mmol) in anhydrous toluene (3.5 mL) at room temperature. After 1 h (LCMS) the reaction mixture was partitioned between DCM and H$_2$O and the aqueous phase further extracted with DCM. The pooled organics were dried over Na$_2$SO$_4$, filtered and concentrated in vacuo. The crude material was purified by flash chromatography (silica gel, EtOAc/petroleum spirits 4:6) to give the title compound (103 mg, 84%) as a pale yellow oil. $^1$H NMR (300 MHz, CDCl$_3$) δ 8.56-8.54 (m, 1H), 7.64-7.59 (m, 1H), 7.23 (s, 1H), 7.21 (s, 1H), 7.19-7.12 (m, 2H), 7.00-6.92 (m, 2H), 4.48 (t, J=6.5 Hz, 2H), 4.25-4.07 (m, 2H), 3.18 (t, J=6.5 Hz, 2H), 3.05-3.02 (m, 1H), 2.40 (s, 3H), 2.32 (s, 3H), 2.08-1.94 (m, 2H), 1.26 (d, J=6.3 Hz, 3H), ESIMS m/z [M+H]$^+$ 531.2.

Example 30c

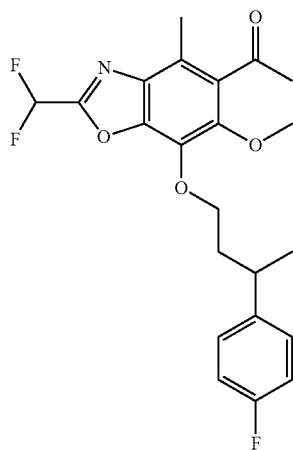 [SMILES: COc1c(C(C)=O)c(C)c2nc(C(F)F)oc2c1OCCC(C)c1ccc(F)cc1]

30a) 5-Acetyl-7-[3-(4-fluorophenyl)butoxy]-6-methoxy-4-methyl-2-difluoromethyl-benzo[d]oxazole A solution of Example 2b) (593 mg, 1.64 mmol), difluoroaceticanhydride (0.612 mL, 4.92 mmol) and p-TsOH (165 mg) in toluene (20 mL) was heated at reflux. After 2 h (LCMS) the reaction mixture was cooled to room temperature and partitioned between DCM and NaHCO$_3$ and the aqueous phase further extracted with DCM. The pooled organics were dried over MgSO$_4$ and concentrated in vacuo. The crude material was purified by flash chromatography (silica gel, DCM) to give the title compound (242 mg, 35%) as a yellow oil. $^1$H NMR (300 MHz, CDCl$_3$) 7.22-7.18 (m, 2H), 7.01-6.93 (m, 2H), 6.76 (t, J=52 Hz, 1H), 4.34-4.15 (m, 2H), 3.89 (s, 3H), 3.04-3.16 (m, 1H), 2.52 (s, 3H), 2.42 (s, 3H), 2.21-1.96 (m, 2H), 1.33 (d, J=7.2 Hz, 3H), ESIMS m/z [M+H]$^+$ 422.2.

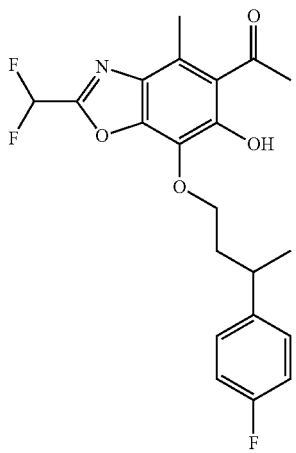 [SMILES: CC(=O)c1c(O)c(OCCC(C)c2ccc(F)cc2)c2oc(C(F)F)nc2c1C]

30b) 5-Acetyl-7-[3-(4-fluorophenyl)butoxy]-6-hydroxy-4-methyl-2-difluoromethyl-benzo[d]oxazole Example 30a) (267 mg, 0.634 mmol) was reacted as described under General Procedure C to give the title compound (256 mg, 99%) without further purification. $^1$H NMR (300 MHz, CDCl$_3$) 9.86 (s, 1H), 7.22-7.17 (m, 2H), 7.02-6.95 (m, 2H), 6.75 (t, J=52 Hz, 1H), 4.33-4.18 (m, 2H), 3.14-3.02 (m, 1H), 2.69 (s, 3H), 2.68 (s, 3H), 2.19-1.95 (m, 2H), 1.32 (d, J=7.2 Hz, 3H), ESIMS m/z [M+H]$^+$ 408.3.

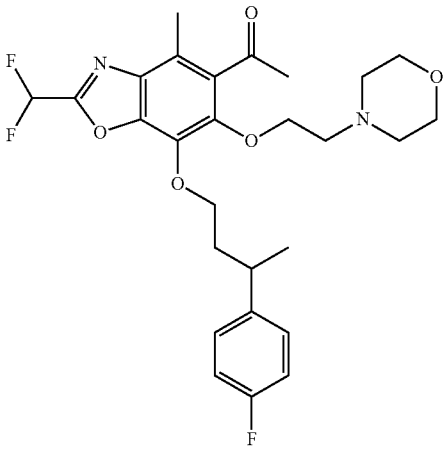

30c) 5-Acetyl-7-[3-(4-fluorophenyl)butoxy]-6-(2-morphin-4-yl-ethoxy)-4-methyl-2-difluoromethyl-benzo[d]oxazole Example 30b) (50 mg, 0.122 mmol) was reacted with 4-(2-chloroethyl)morpholine hydrochloride (27 mg, 0.146 mmol) as described under General Procedure F to give the title compound (39 mg, 61%) as a yellow oil. $^1$H NMR (300 MHz, CDCl$_3$) 7.22-7.17 (m, 2H), 7.01-6.95 (m, 2H), 6.76 (t, J=52 Hz, 1H), 4.34-4.18 (m, 2H), 4.12 (t, J=5.7 Hz, 2H), 3.72 (t, J=4.8 Hz, 2H), 3.14-3.01 (m, 1H), 2.67 (t, J=5.7 Hz, 2H), 2.56 (s, 3H), 2.51 (t, J=4.8 Hz, 4H), 2.42 (s, 3H), 2.20-1.95 (m, 2H), 1.33 (d, J=6.9 Hz, 3H), ESIMS m/z [M+H]$^+$ 521.3.

Example 31b

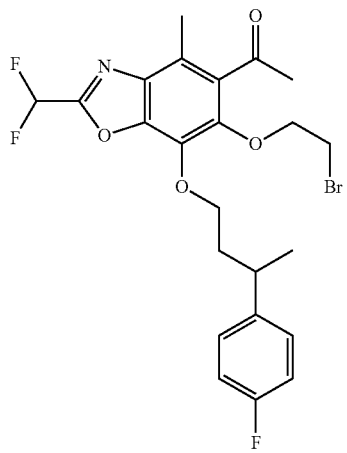 [SMILES: CC(=O)c1c(OCCBr)c(OCCC(C)c2ccc(F)cc2)c2oc(C(F)F)nc2c1C]

31a) 5-Acetyl-7-[3-(4-fluorophenyl)butoxy]-6-(2-bromoethoxy)-4-methyl-2-difluoromethyl-benzo[d]oxazole Example 30b) (192 mg, 0.473 mmol) was reacted with dibromoethane (excess) as described under General Procedure D. The crude material was purified by flash chromatography (silica gel, Et$_2$O/hexane 3:7) to give the title compound (217 mg, 89%) as a pale yellow oil. $^1$H NMR (300 MHz, CDCl$_3$) 7.23-7.18 (m, 2H), 7.02-6.96 (m, 2H), 6.76 (t, J=52 Hz, 1H), 4.38-4.18 (m, 4H), 3.55 (t, J=6.0 Hz, 2H), 3.15-3.03 (m, 1H), 2.55 (s, 3H), 2.42 (s, 3H), 2.21-1.96 (m, 2H), 1.33 (d, J=6.9 Hz, 3H), ESIMS m/z [M+H]$^+$ 514.3.

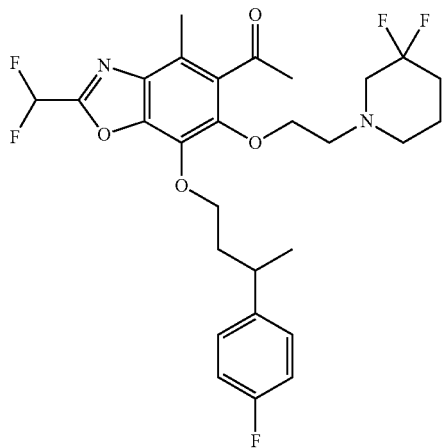 [SMILES: CC(=O)c1c(OCCN2CCCC(F)(F)C2)c(OCCC(C)c2ccc(F)cc2)c2oc(C(F)F)nc2c1C]

31b) 5-Acetyl-7-[3-(4-fluorophenyl)butoxy]-6-(2-(3,3-difluoropiperidin-1-yl)-ethoxy)-4-methyl-2-difluoromethyl-benzo[d]oxazole A solution of Example 31a) (56 mg, 109 mmol), NaH (13 mg, 0.327 mmol), 3,3-difluoropiperidine hydrochloride (52 mg, 0.327 mmol) and NaI (cat.) in DMF was heated to 65° C. overnight. The reaction mixture was cooled to room temperature, diluted with EtOAc and washed twice with water and brine, dried over MgSO$_4$ and concentrated in vacuo. The crude product was purified by column chromatography (silica gel, Et$_2$O/hexane, 2:3) to give the title compound as a clear colourless oil (36 mg, 60%). $^1$H NMR (300 MHz, CDCl$_3$) 7.22-7.17 (m, 2H), 7.00-6.93 (m, 2H), 6.75 (t, J=52 Hz, 1H), 4.34-4.19 (m, 2H), 4.15 (t, J=5.4 Hz, 2H), 3.12-3.01 (m, 1H), 2.80-2.73 (m, 4H), 2.54-2.48 (m, 5H), 2.41 (s, 3H), 2.20-1.74 (m, 6H), 1.33 (d, J=7.2 Hz, 3H), ESIMS m/z [M+H]$^+$ 555.2.

Example 32c

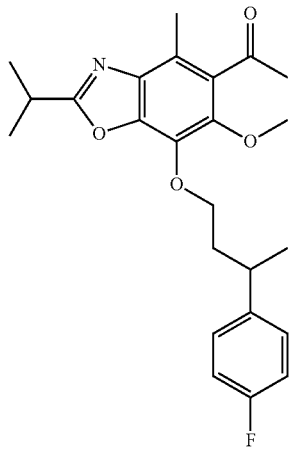 [SMILES: COc1c(C(C)=O)c(C)c2nc(C(C)C)oc2c1OCCC(C)c1ccc(F)cc1]

32a) 5-Acetyl-7-[3-(4-fluorophenyl)butoxy]-2-isopropyl-6-methoxy-4-methylbenzo[d]oxazole A stirred solution of Example 2b) (525 mg, 1.45 mmol), isobutyric anhydride (0.654 mL, 4.35 mmol), and p-TsOH (100 mg) in toluene (30 mL) was heated at reflux. After 48 h the reaction mixture was cooled to room temperature and partitioned between chloroform and NaHCO$_3$. The pooled organics were dried over MgSO$_4$ and concentrated in vacuo. The crude material was purified by flash chromatography (neutral alumina, EtOAc/hexane 5:95) to give the title compound (476 mg, 79%), as an oil. $^1$H NMR (300 MHz, CDCl$_3$) δ 7.22-7.17 (m, 2H), 7.01-6.95 (m, 2H), 4.31-4.13 (m, 2H), 3.86 (s, 3H), 3.26-3.03 (m, 2H), 2.51 (s, 3H), 2.40 (s, 3H), 2.18-1.94 (m, 2H), 1.40 (d, J=7 Hz, 6H), 1.33 (d, J=7.0 Hz, 3H), ESIMS m/z [M+H]$^+$ 414.2.

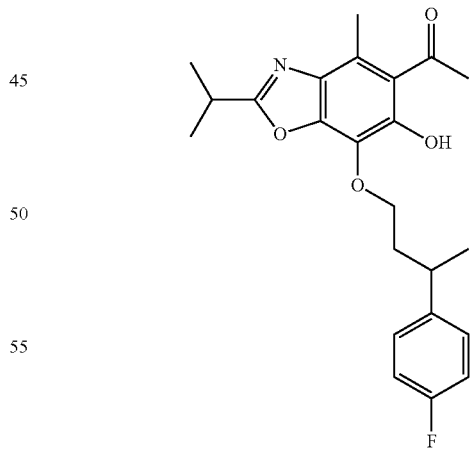

32b) 5-Acetyl-7-[3-(4-fluorophenyl)butoxy]-6-hydroxy-2-isopropyl-4-methylbenzo[d]oxazole Example 32a) (260 mg, 0.63 mmol) was reacted as described under General Procedure C using BCl$_3$ (2.5 eq.). The crude residue was purified by flash chromatography (silica gel, EtOAc/hexane 1:9) to give the title compound (234 mg, 93%) as a crystalline solid. ¹H NMR (300 MHz, CDCl₃) δ 10.89 (s, 1H), 7.21-7.16 (m, 2H), 7.00-6.94 (m, 2H), 4.25-4.13 (m, 2H), 3.23-3.04 (m, 2H), 2.73 (s, 3H), 2.68 (s, 3H), 2.18-1.94 (m, 2H), 1.40 (d, J=7 Hz, 6H), 1.31 (d, J=6.5 Hz, 3H), ESIMS m/z [M+H]⁺ 400.2.

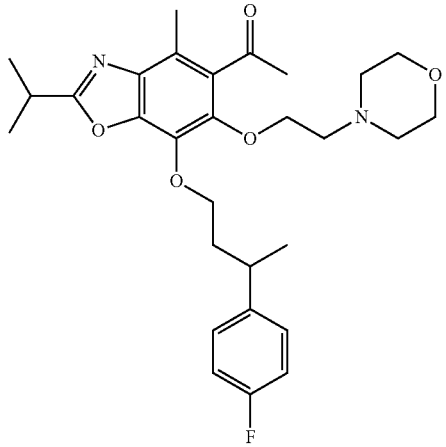 [SMILES: CC(=O)c1c(OCCN2CCOCC2)c(OCCC(C)c2ccc(F)cc2)c2oc(C(C)C)nc2c1C]

32c) 5-Acetyl-7-[3-(4-fluorophenyl)butoxy]-2-isopropyl-4-methyl-6-(2-morpholin-4-O-ethoxy)-benzo[d]oxazole Example 32b) (66 mg, 0.165 mmol) was reacted with 4-(2-chloroethyl)morpholine hydrochloride (41 mg, 0.223 mmol) as described under General Procedure F. The crude residue was purified by flash chromatography (silica gel, EtOAc/hexane 7:3) to give the title compound (72 mg, 85%) as an oil. ¹H NMR (300 MHz, CDCl₃) δ 7.21-7.16 (m, 2H), 7.01-6.98 (m, 2H), 4.26-4.18 (m, 2H), 4.08 (t, J=5.5 Hz, 2H), 3.73 (m, 4H), 3.19 (hep, J=7 Hz, 1H), 3.06 (m, 1H), 2.67 (t, J=5.5 Hz, 2H), 2.53 (s, 3H), 2.53-2.50 (m, 4H) 2.39 (s, 3H), 2.11-1.98 (m, 2H), 1.39 (d, J=7.0 Hz, 6H), 1.32 (d, J=7.0 Hz, 3H), ESIMS m/z [M+H]⁺ 513.5.

Example 33b

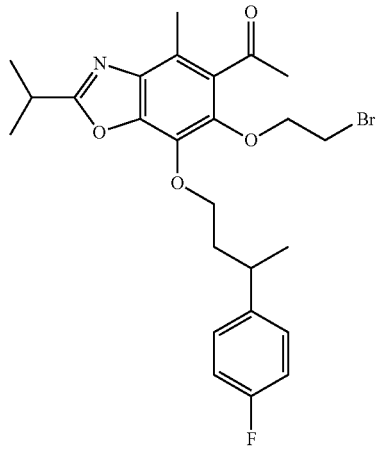 [SMILES: CC(=O)c1c(OCCBr)c(OCCC(C)c2ccc(F)cc2)c2oc(C(C)C)nc2c1C]

33a) 5-Acetyl-6-(2-bromoethoxy)-7-[3-(4-fluorophenyl)butoxy]-2-isopropyl-4-methylbenzo[d]oxazole Example 32b) (165 mg, 0.0.41 mmol) was reacted with dibromoethane (excess) as described under General Procedure D. The crude residue was concentrated in vacuo to give the title compound (201 mg, 96%) as a pale yellow oil which was used in subsequent steps without further purification. ¹H NMR (300 MHz, CDCl₃) δ 7.22-7.17 (m, 2H), 7.01-6.95 (m, 2H), 4.31-4.19 (m, 4H), 3.55 (t, J=6.0 Hz, 2H), 3.19 (hep, J=7 Hz, 1H), 3.08 (m, 1H), 2.53 (s, 3H), 2.39 (s, 3H), 2.13-1.96 (m, 2H), 1.39 (d, J=7.0 Hz, 6H), 1.33 (d, J=7.0 Hz, 3H), ESIMS m/z [M+H]⁺ 506.2, 508.3.

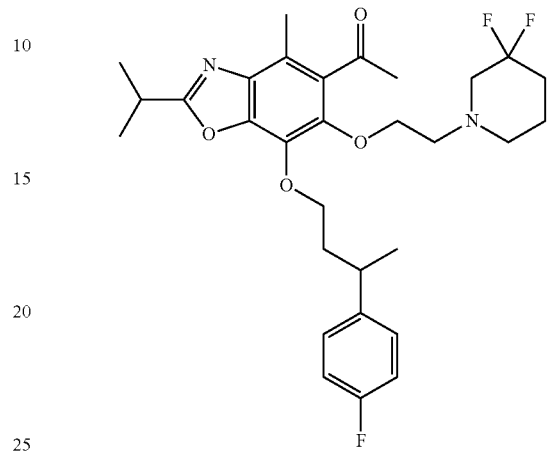

33b) 5-Acetyl-6-[2-(3,3-difluoropiperidin-1-yl)ethoxy]-7-[3-(4-fluorophenyl)butoxy]-2-isopropyl-4-methylbenzo[d]oxazole A solution of Example 33a) (109 mg, 0.215 mmol), sodium carbonate (160 mg, 1.51 mmol), 3,3-difluoropiperidine hydrochloride (250 mg, 1.58 mmol) and NaI (cat.) in DMF was heated to 65° C. for 4 d. The reaction mixture was cooled to room temperature, diluted with water and extracted with ether. The pooled organics were dried over MgSO₄ and concentrated in vacuo. The crude product was purified by preparative thin layer chromatography (silica gel, EtOAc/hexane, 2:8) to give the title compound as a clear colourless oil (87 mg, 74%). ¹H NMR (300 MHz, CDCl₃) δ 7.21-7.16 (m, 2H), 7.00-6.95 (m, 2H), 4.29-4.17 (m, 2H), 4.10 (t, J=5.5 Hz, 2H), 3.18 (hep, J=7 Hz, 1H), 3.16-2.98 (m, 1H), 2.82-2.74 (m, 4H), 2.54-2.51 (m, 2H), 2.52 (s, 3H), 2.38 (s, 3H), 2.16-1.74 (m, 6H), 1.39 (d, J=7.0 Hz, 6H), 1.32 (d, J=7.0 Hz, 3H), ESIMS m/z [M+H]⁺ 547.2.

Example 34

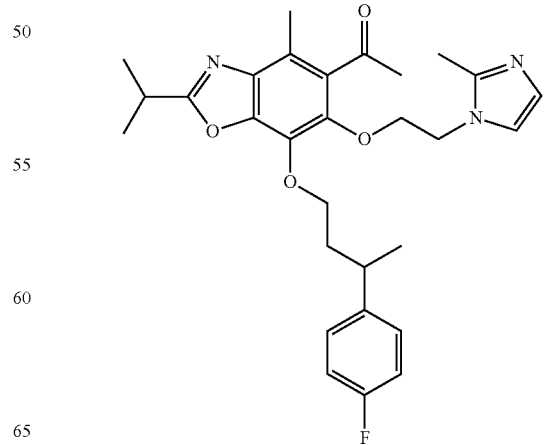

5-Acetyl-7-[3-(4-fluorophenyl)butoxy]-2-isopropyl-1-4-methyl-6-[2-(2-methyl-1H-imidazol-1-yl)ethoxy]-benzo[d]oxazole Example 33a) (94 mg, 0.186 mmol) was reacted with 2-methylimidazole (153 mg, 1.86 mmol) as described under General Procedure E. The crude material was purified by preparative thin layer chromatography (silica gel, MeOH/CHCl$_3$ 5:95) to give the title compound (74 mg, 79%) as an oil. $^1$H NMR (300 MHz, CDCl$_3$) δ 7.17-7.12 (m, 2H), 7.00-6.91 (m, 4H), 4.21-4.06 (m, 6H), 3.18 (hep, J=7 Hz, 1H), 2.96 (m, 1H), 2.41 (s, 3H), 2.37 (s, 3H), 2.36 (s, 3H), 2.05-1.86 (m, 2H), 1.39 (d, J=7.0 Hz, 6H), 1.30 (d, J=7.0 Hz, 3H), ESIMS m/z [M+H]$^+$ 508.3.

Example 35d

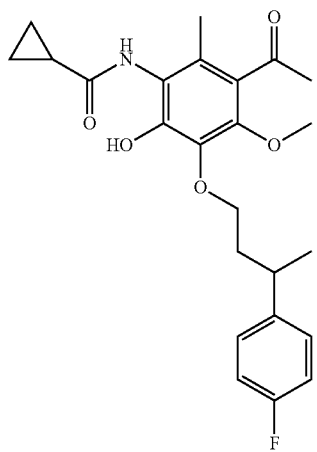 [SMILES: COc1c(OCCC(C)c2ccc(F)cc2)c(O)c(NC(=O)C2CC2)c(C)c1C(C)=O]

35a) N-(3-acetyl-5-(3-(4-fluorophenyl)butoxy)-6-hydroxy-4-methoxy-2-methylphenyl)cyclopropanecarboxamide To a stirred solution of Example 2b) (739 mg, 2.04 mmol) and pyridine (197 pt, 2.45 mmol) in EtOAc (16 mL) at room temperature was added cyclopropanecarbonyl chloride (186 µL, 2.04 mmol). After 1 h (LCMS) the reaction was diluted with EtOAc and washed twice with HCl (2M aq.). the organic layer was dried over MgSO$_4$, concentrated in vacuo and the crude residue purified by flash chromatography (silica gel, Et$_2$O/DCM 1:4) to give the title compound (0.83), slightly contaminated with the corresponding o-acylated regioisomer (0.17) (0.7 g, 80% yield). $^1$H NMR (300 MHz, CDCl$_3$) (title compound) 7.76 (s, 1H), 7.21-7.15 (m, 2H), 7.00-6.94 (m, 2H), 3.98-3.92 (m, 2H), 3.81 (s, 3H), 3.08-2.95 (m, 1H), 2.46 (s, 3H), 2.08 (s, 3H), 2.05-1.99 (m, 2H), 1.71-1.60 (m, 2H, 1.29 (d, J=6.9 Hz, 3H), 1.18-1.11 (m, 2H), 0.97-0.92 (m, 2H), ESIMS m/z [M+H]$^+$ 430.2.

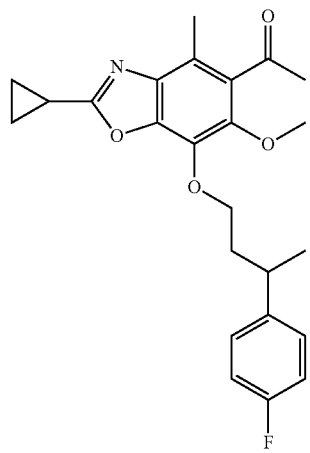 [SMILES: COc1c(C(C)=O)c(C)c2nc(C3CC3)oc2c1OCCC(C)c1ccc(F)cc1]

35b) 5-Acetyl-7-[3-(4-fluorophenyl)butoxy]-2-cyclopropyl-6-methoxy-4-methylbenzo[d]oxazole To a solution of Example 35a) (0.665 g, 1.55 mmol) in chlorobenzene (6 mL) at room temperature was added TFA (3 drops). The mixture was heated to reflux overnight. The solution was cooled to room temperature and concentrated in vacuo and the residue partitioned between DCM and NaHCO$_3$. The aqueous phase was extracted twice with DCM, dried over MgSO$_4$ and concentrated in vacuo. The crude product was purified by flash chromatography (silica gel, Et$_2$O/hexane 1:1) to give the title compound (454 mg, 71%). $^1$H NMR (300 MHz, CDCl$_3$) 7.21-7.16 (m, 2H), 7.02-6.96 (m, 2H), 4.25-4.08 (m, 2H), 3.84 (s, 3H), 3.13-3.01 (m, 1H), 2.50 (s, 3H), 2.36 (s, 3H), 2.20-1.93 (m, 3H), 1.32 (d, J=6.9 Hz, 3H), 1.15 (d, J=3.6 Hz, 4H), ESIMS m/z [M+H]$^+$ 412.2.

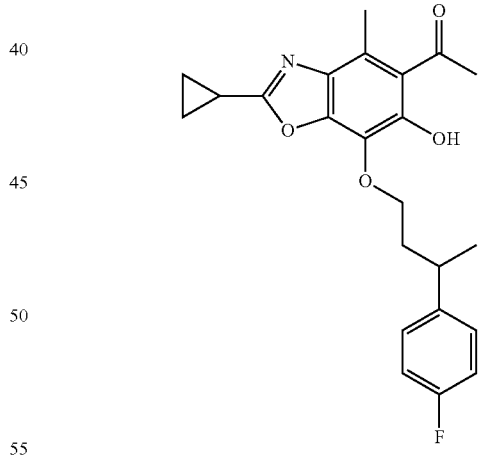

35c) 5-Acetyl-7-[3-(4-fluorophenyl)butoxy]-2-cyclopropyl-6-hydroxy-4-methylbenzo[d]oxazole Example 35b) (469 mg, 1.14 mmol) was reacted as described under General Procedure C to give the title compound (453 mg, 100%) without further purification. $^1$H NMR (300 MHz, CDCl$_3$) 10.91 (s, 1H), 7.21-7.16 (m, 2H), 7.01-6.95 (m, 2H), 4.21-4.06 (m, 2H), 3.12-3.00 (m, 1H), 2.68 (s, 6H), 2.19-1.92 (m, 3H), 1.31 (d, J=6.9 Hz, 3H), 1.19-1.20 (m, 4H), ESIMS m/z [M+H]$^+$ 398.3.

4H), 3.54 (t, J=6.0 Hz, 2H), 3.12-3.00 (m, 1H), 2.53 (s, 3H), 2.35 (s, 3H), 2.19-1.93 (m, 3H), 1.32 (d, J=6.9 Hz, 3H), 1.16-1.14 (m, 4H), ESIMS m/z [M+H]+ 504.2.

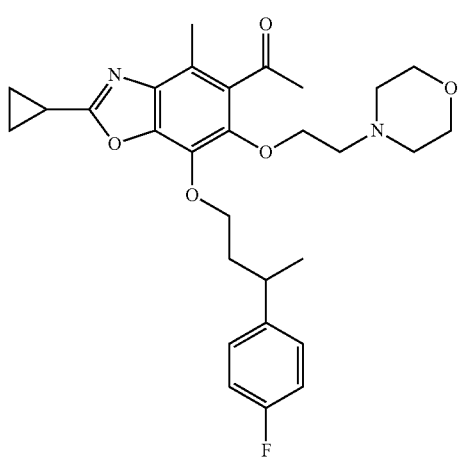 [SMILES: CC(=O)c1c(OCCN2CCOCC2)c(OCCC(C)c2ccc(F)cc2)c2oc(C3CC3)nc2c1C]

35d) 5-Acetyl-7-[3-(4-fluorophenyl)butoxy]-2-cyclopropyl-4-methyl-6-(2-morpholin-4-yl-ethoxy)-benzo[d]oxazole Example 35c) (54 mg, 0.135 mmol) was reacted with 4-(2-chloroethyl)morpholine hydrochloride (30 mg, 0.162 mmol) as described under General Procedure F to give the title compound (44 mg, 64%) as a yellow oil. $^1$H NMR (300 MHz, CDCl$_3$) 7.20-7.15 (m, 2H), 7.01-6.96 (m, 2H), 4.24-4.10 (m, 2H), 4.06 (t, J=5.7 Hz, 2H), 3.72 (t, J=4.8 Hz, 4H), 3.10-2.98 (m, 1H), 2.66 (t, J=5.4 Hz, 2H), 2.54 (s, 3H), 2.51 (br t, J=4.5 Hz, 4H), 2.35 (s, 3H), 2.18-1.92 (m, 3H), 1.31 (d, J=6.9 Hz, 3H), 1.16-1.13 (m, 4H), ESIMS m/z [M+H]+ 511.2.

Example 36b

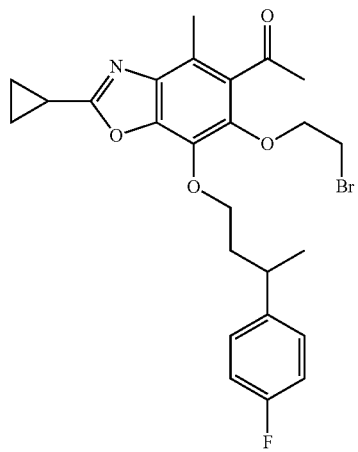 [SMILES: CC(=O)c1c(OCCBr)c(OCCC(C)c2ccc(F)cc2)c2oc(C3CC3)nc2c1C]

36a) 5-Acetyl-7-[3-(4-fluorophenyl)butoxy]-2-cyclopropyl-4-methyl-6-(2-bromoethoxy)-benzo[d]oxazole Example 35c) (209 mg, 0.526 mmol) was reacted with dibromoethane (excess) as described under General Procedure D. The crude material was purified by flash chromatography (silica gel, Et$_2$O/hexane 1:1) to give the title compound (180 mg, 68%) as a pale yellow oil. $^1$H NMR (300 MHz, CDCl$_3$) 7.21-7.16 (m, 2H), 7.02-6.96 (m, 2H), 4.29-4.11 (m,

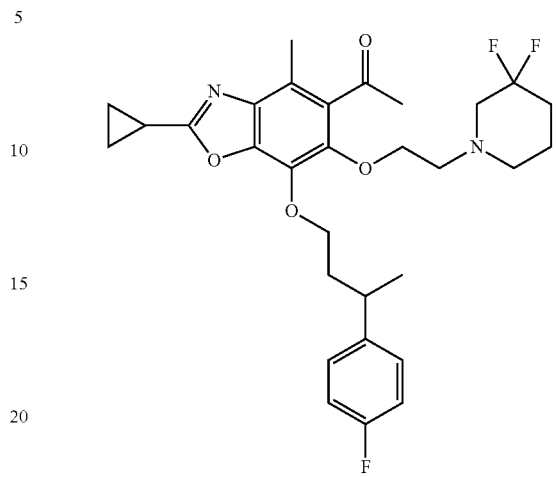

36b) 5-Acetyl-6-[2-(3,3-difluoropiperidin-1-yl)ethoxy]-7-[3-(4-fluorophenyl)butoxy]-2-isopropyl-4-methylbenzo[d]oxazole A solution of Example 36a) (54 mg, 106 mmol), NaH (12 mg, 0.319 mmol), 3,3-difluoropiperidine hydrochloride (50 mg, 0.319 mmol) and NaI (cat.) in DMF was heated to 65° C. overnight. The reaction mixture was cooled to room temperature, diluted with EtOAc and washed twice with water and brine, dried over MgSO$_4$ and concentrated in vacuo. The crude product was purified by column chromatography (silica gel, Et$_2$O/hexane, 1:1) to give the title compound as a clear, colourless oil (39 mg, 68%). $^1$H NMR (300 MHz, CDCl$_3$) 7.20-7.16 (m, 2H), 7.02-6.96 (m, 2H), 4.24-4.11 (m, 2H), 4.08 (t, J=5.4 Hz, 2H), 3.09-2.98 (m, 1H), 2.81-2.74 (m, 4H), 2.55-2.48 (m, 5H), 2.35 (s, 3H), 2.19-1.73 (m, 7H), 1.32 (d, J=6.9 Hz, 3H), 1.16-1.13 (m, 4H), ESIMS m/z [M+H]+ 545.3.

Example 37j

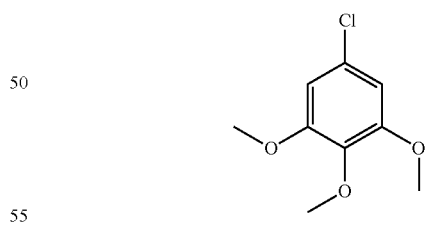

37a) 5-Chloro-1,2,3-trimethoxybenzene

To a stirred suspension of 3,4,5-trimethoxyaniline (6.27 g, 34.2 mmol) in 37% HCl:H$_2$O (75:25) at 0° C. was added dropwise a solution of NaNO$_2$ (2.51 g, 36.4 mmol) in H$_2$O. The temperature was maintained below 5° C. during the addition. Upon complete addition of NaNO$_2$, an ice cold solution of CuCl (4.41 g, 44.6 mmol) in 37% HCl was added and the solution allowed to warm to room temperature. The stirred suspension was warmed to 60° C. until evolution of N$_2$ ceased. The product was filtered and washed with cold H₂O. The crude product was purified by flash chromatography (silica gel, EtOAc/Petroleum Spirit 3:17) to give the title compound as a white solid (4.68 g, 67%). ¹H NMR (300 MHz, CDCl₃) δ 6.58 (s, 2H), 3.85 (s, 6H), 3.82 (s, 3H), ESIMS m/z [M+H]⁺ 203.2.

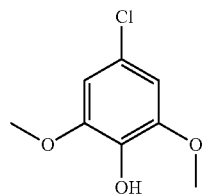

37b) 4-Chloro-2,6-dimethoxyphenol

To a stirred solution 37a) (4.67 g, 23.1 mmol) in dry DCM (40 mL) at 0° C. under nitrogen was added BCl₃ (1M in DCM, 24 mL, 24.0 mmol) drop-wise. The solution was allowed to warm to room temperature over 3.5 h. The reaction was quenched with the addition of H₂O (40 mL) and the product extracted with EtOAc (3×30 mL). The organics were pooled, dried over Na₂SO₄, filtered and concentrated in vacuo. The crude product was purified by flash chromatography (silica gel, EtOAc/Petroleum Spirit, 2:8) to give the title compound as a white solid (4.29 g, 98%). ¹H NMR (300 MHz, CDCl₃) δ 6.58 (s, 2H), 5.41 (s, 1H), 3.88 (s, 6H), ESIMS m/z [M+H]⁺ 187.3.

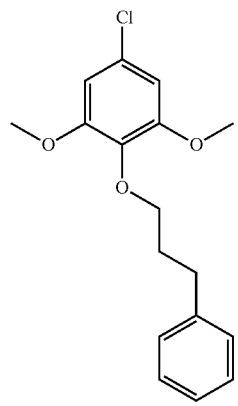 [SMILES: COc1cc(Cl)cc(OC)c1OCCCc1ccccc1]

37c) 5-Chloro-1,3-dimethoxy-2-(3-phenylpropoxy)benzene

Example 37b) (4.30 g, 20.6 mmol) was reacted with 3-phenylbromopropane (5.12 g, 25.7 mmol) as described under General Procedure D. The crude product was purified by flash chromatography (silica gel, diethyl ether/petroleum spirit 1:9) to give the title compound (6.29 g, 90%) as a colourless oil. ¹H NMR (300 MHz, CDCl₃) δ 7.30-7.10 (m, 5H), 6.64 (s, 2H), 4.03-3.99 (t, J=6.3 Hz, 2H), 3.89 (s, 3H), 3.84 (s, 3H), 2.85-2.80 (m, 2H), 2.11-2.31 (m, 2H), ESIMS m/z [M+H]⁺ 306.8.

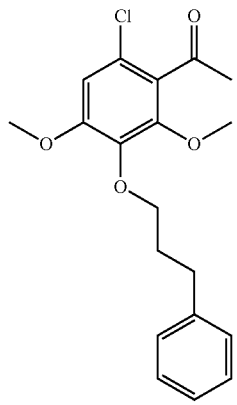 [SMILES: COc1cc(Cl)c(C(C)=O)c(OC)c1OCCCc1ccccc1]

37d) 1-(6-Chloro-2,4-dimethoxy-3-(3-phenylpropoxy)phenyl)ethanone

Example 37c) (2.57 g, 8.39 mmol) was reacted as described under General Procedure B using SnCl₄ (1M DCM) in place of TiCl₄. The crude product was purified by flash chromatography (silica gel, diethyl ether/petroleum spirit 1:9) to give the title compound (1.04 g, 35%) as a pale yellow oil. ¹H NMR (300 MHz, CDCl₃) δ 7.30-7.10 (m, 5H), 6.68 (s, 1H), 4.03-3.99 (t, J=6.3 Hz, 2H), 3.89 (s, 3H), 3.84 (s, 3H), 2.85-2.80 (m, 2H), 2.51 (s, 3H), 2.11-2.31 (m, 2H), ESIMS m/z [M+H]⁺ 349.2.

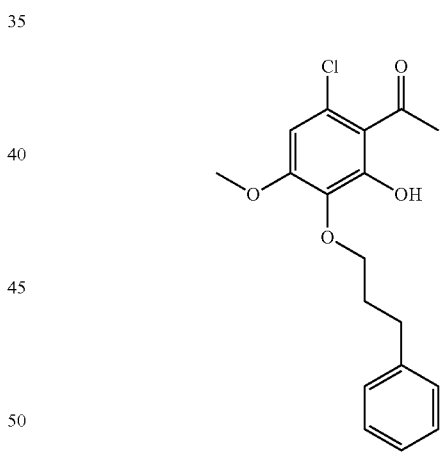

37e) 1-(6-Chloro-2-hydroxy-4-methoxy-3-(3-phenylpropoxy)phenyl)ethanone

Example 37d) (162.1 mg, 0.46 mmol) was reacted as described under General Procedure C. The crude product was purified by flash chromatography (silica gel, diethyl ether/petroleum spirit 3:17) to give the title compound (136 mg, 88%). ¹H NMR (300 MHz, CDCl₃) δ 12.82 (s, 1H), 7.29-7.18 (m, 5H), 6.57 (s, 1H), 4.04-4.00 (t, J=6.3 Hz, 2H), 3.89 (s, 3H), 2.86-2.80 (m, 5H), 2.11-2.31 (m, 2H), ESIMS m/z [M+H]⁺ 335.2.

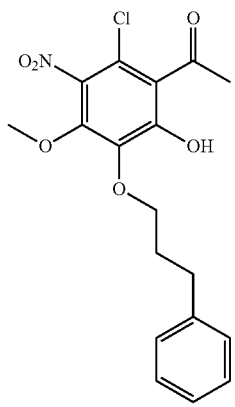 [SMILES: COc1c(OCCCc2ccccc2)c(O)c(C(C)=O)c(Cl)c1[N+](=O)[O-]]

37f) 1-(2-Chloro-6-hydroxy-4-methoxy-3-nitro-5-(3-phenylpropoxy)phenyl)ethanone A suspension of Example 37e) (130.0 mg, 0.39 mmol) and acidic clay supported $Cu(NO_3)_2$ (208 mg, 0.74 mmol) in anhydrous DCM (5 mL) was stirred at room temperature for 3 h. The suspension was filtered and concentrated in vacuo. The crude product was purified by flash chromatography (silica gel, ethyl acetate/petroleum spirit 1:9) to give the title compound as a yellow solid (54 mg, 37%). $^1$H NMR (300 MHz, $CDCl_3$) δ 12.85 (s, 1H), 7.30-7.20 (m, 5H), 4.12-4.08 (m, 5H), 2.86-2.80 (m, 5H), 2.15-2.07 (m, 2H), ESIMS m/z [M–H]$^+$ 378.3.

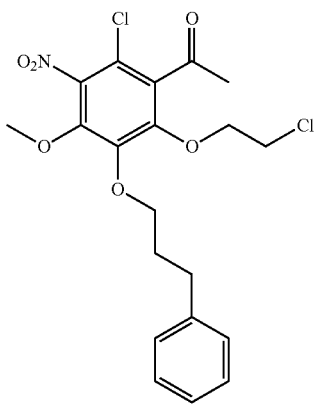 [SMILES: COc1c(OCCCc2ccccc2)c(OCCCl)c(C(C)=O)c(Cl)c1[N+](=O)[O-]]

37g) 1-(2-Chloro-6-(2-chloroethoxy)-4-methoxy-3-nitro-5-(3-phenylpropoxy)phenyl)ethanone Example 37f) (95 mg, 0.25 mmol) and 1-bromo-2-chloroethane (259 mg, 1.80 mmol) were reacted as described under General Procedure D. The crude product was purified by flash chromatography (silica gel, diethyl ether/petroleum spirit 3:7) to give the title compound (104 mg, 94%). $^1$H NMR (300 MHz, $CDCl_3$) δ 7.31-7.19 (m, 5H), 4.34-4.31 (t, J=5.1 Hz, 2H), 4.14-4.09 (t, J=6.6 Hz, 2H), 3.98 (s, 3H), 3.71-3.68 (t, J=6.0 Hz, 2H), 2.83-2.78 (t, J=7.5 Hz, 2H), 2.56 (s, 3H), 2.16-2.08 (m, 2H), ESIMS m/z [M+NH$_4$]$^+$ 459.2.

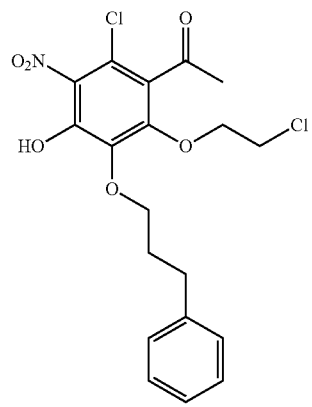 [SMILES: CC(=O)c1c(Cl)c([N+](=O)[O-])c(O)c(OCCCc2ccccc2)c1OCCCl]

37h) 1-(2-Chloro-6-(2-chloroethoxy)-4-hydroxy-3-nitro-5-(3-phenylpropoxy)phenyl)ethanone LiCl (59 mg, 1.40 mmol) was added to a solution of Example 37g) (101 mg, 0.23 mmol) in dry DMF (5 mL). The mixture was stirred at 90° C. for 16 h (TLC). The solution was concentrated in vacuo and the residue was dissolved in EtOAc (10 mL) and this solution was washed with water. The organic layer was dried over $MgSO_4$ and concentrated in vacuo and the crude product was purified by flash chromatography (silica gel, ethyl acetate/petroleum spirit 3:17) to give the title compound (87 mg, 87%). $^1$H NMR (300 MHz, $CDCl_3$) δ 8.71 (s, 1H), 7.32-7.20 (m, 5H), 4.40-4.36 (m, 2H), 4.16-4.11 (t, J=6.3 Hz, 2H), 3.71-3.67 (m, 2H), 2.84-2.79 (t, J=7.5 Hz, 2H), 2.55 (s, 3H), 2.19-2.09 (m, 2H). ESIMS m/z [M+H]$^+$ 428.2.

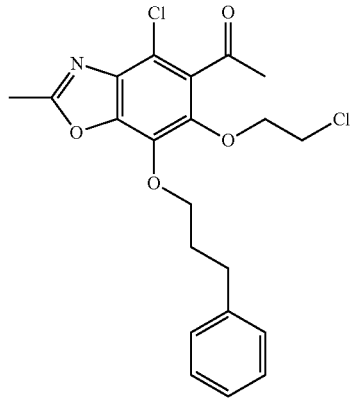 [SMILES: CC(=O)c1c(OCCCl)c(OCCCc2ccccc2)c2oc(C)nc2c1Cl]

37i) 5-Acetyl-4-chloro-6-(2-chloroethoxy)-7-(3-phenylpropoxy)-2-methyl-benzo[d]oxazole To a stirred solution 37h) (46 mg, 0.11 mmol) in dry EtOH (5 mL) under nitrogen was added $SnCl_2.2H_2O$ (241 mg, 1.07 mmol). The solution was heated to reflux for 4 h. The solution was concentrated in vacuo and the residue was dissolved in EtOAc (5 mL) and treated with sodium potassium tartrate (1M, 5 mL). The mixture was warmed to 50° C. heated at this temperature until the layers visibly separated. The organic layer was separated and the aqueous further extracted with EtOAc (2×5 mL). The organics were pooled, dried over $Na_2SO_4$, filtered and concentrated in vacuo. The crude material was taken up in dry DMF (3 mL) and to this solution triethyl orthoacetate (3 mL, excess) was added. The solution was stirred at reflux for 1 h. The solution was concentrated in vacuo and the residue was taken in CH$_2$Cl$_2$ (5 mL) and washed with water. The organic layer was dried over Na$_2$SO$_4$ and concentrated in vacuo. The crude product was purified by flash chromatography (silica gel, ethyl acetate/petroleum spirit 3:18) to give the title compound (30 mg, 64%). $^1$H NMR (300 MHz, CDCl$_3$) δ 7.33-7.21 (m, 5H), 4.45-4.40 (t, J=6.6 Hz, 2H), 4.29-4.25 (m, 2H), 3.75-3.72 (t, J=5.7 Hz, 2H), 2.89-2.84 (t, J=7.2 Hz, 2H), 2.65 (s, 3H), 2.59 (s, 3H), 2.19-2.09 (m, 2H), ESIMS m/z [M+H]$^+$ 422.2.

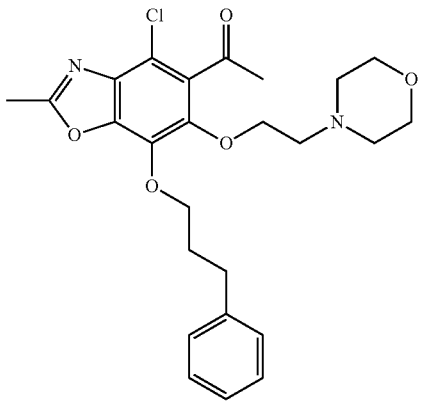 [SMILES: CC(=O)c1c(OCCN2CCOCC2)c(OCCCc2ccccc2)c2oc(C)nc2c1Cl]

37j) 5-Acetyl-4-chloro-6-(2-(morpholin-4-yl)ethoxy)-2-methyl-7-(3-phenyl)propoxy)benzo[d]oxazole To a stirred solution of Example 37i) (9.2 mg, 0.02 mmol) in dry DMF (1 mL) under N$_2$ were added morpholine (20 μL, 0.23 mmol) and NaI (15.1 mg, 0.10 mmol). The solution was heated to 60° C. for 24 h. After this time the reaction was cooled, diluted with EtOAc (5 mL) and washed with water (3×2 mL). The organic layer was dried over MgSO$_4$, concentrated in vacuo. The crude product was purified by flash chromatography (silica gel, methanol/ethyl acetate/petroleum spirit 2:18:80) to give the title compound (5 mg, 47%). $^1$H NMR (300 MHz, CDCl$_3$) δ 7.30-7.20 (m, 5H), 4.43-4.39 (t, J=6.6 Hz, 2H), 4.16-4.12 (t, J=5.4 Hz, 2H), 3.73-3.70 (t, J=4.5 Hz, 4H), 2.88-2.83 (t, J=7.5 Hz, 2H), 2.64 (s, 3H), 2.60 (s, 3H), 2.54-2.51 (m, 4H), 2.19-2.09 (m, 2H), ESIMS m/z [M+H]$^+$ 473.2.

Example 38h

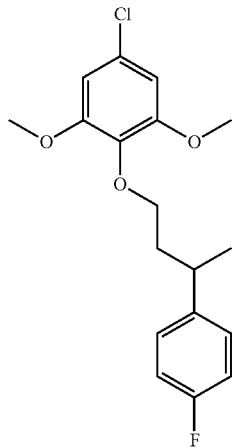 [SMILES: COc1cc(Cl)cc(OC)c1OCCC(C)c1ccc(F)cc1]

38a) 5-Chloro-2-(3-(4-fluorophenyl)butoxy)-1,3-dimethoxybenzene

Example 37b) (3.20 g, 17.0 mmol) was reacted with 1-(3-bromo-1-methyl-propyl)-4-fluorobenzene (4.11 g, 17.8 mmol) as described under General Procedure D. The crude product was purified by flash chromatography (silica gel, diethyl ether/petroleum spirit 1:9) to give the title compound (5.01 g, 96%) as a colourless oil. $^1$H NMR (300 MHz, CDCl$_3$) δ 7.21-7.16 (m, 2H), 7.00-6.94 (m, 2H), 6.64 (s, 2H), 4.03-3.99 (m, 2H), 3.89 (s, 6H), 3.13-3.01 (m, 1H), 2.10-1.90 (m, 2H), 1.30-1.28 (d, J=7.0 Hz, 3H), ESIMS m/z [M+H]$^+$ 356.3.

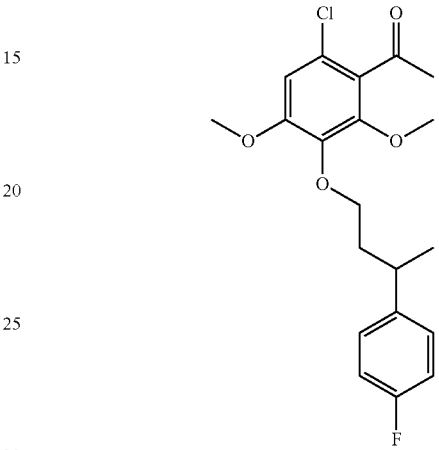

38b) 1-(6-Chloro-3-(3-(4-fluorophenyl)butoxy)-2,4-dimethoxyphenyl)ethanone

Example 38a) (6.98 g, 20.6 mmol) was reacted as described under General Procedure B using SnCl$_4$ (1M in DCM) in place of TiCl$_4$. The crude product was purified by flash chromatography (silica gel, diethyl ether/petroleum spirit 1:9) to give the title compound (4.47 g, 57%) as a pale yellow oil. $^1$H NMR (300 MHz, CDCl$_3$) δ 7.20-7.15 (m, 2H), 7.00-6.94 (m, 2H), 6.61 (s, 1H), 3.94-3.80 (m, 8H), 3.10-2.99 (m, 1H), 2.49 (s, 3H), 2.10-1.90 (m, 2H), 1.30-1.28 (d, J=7.0 Hz, 3H), ESIMS m/z [M+H]$^+$ 381.2.

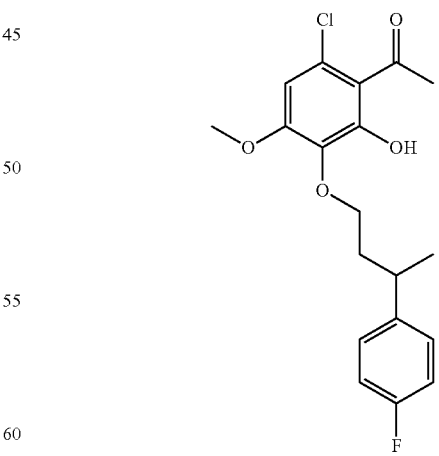

38c) 1-(6-chloro-3-(3-(4-fluorophenyl)butoxy)-2-hydroxy-4-methoxyphenyl) ethanone Example 38b) (4.47 g, 11.7 mmol) was reacted as described under General Procedure C. The crude product was purified by flash chromatography (silica gel, diethyl ether/petroleum spirit 3:17) to give the title compound (3.60 g, 84%). $^1$H NMR (300 MHz, CDCl$_3$) δ 12.79 (s, 1H), 7.21-7.16 (m, 2H), 7.00-6.94 (m, 2H), 6.55 (s, 1H), 3.94-3.80 (m, 5H), 3.13-3.01 (m, 1H), 2.80 (s, 3H), 2.10-1.90 (m, 2H), 1.30-1.28 (d, J=7.0 Hz, 3H), ESIMS m/z [M+H]$^+$ 367.3.

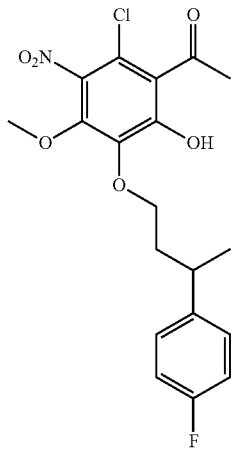 [SMILES: COc1c(OCCC(C)c2ccc(F)cc2)c(O)c(C(C)=O)c(Cl)c1[N+](=O)[O-]]

38d) 1-(2-chloro-5-(3-(4-fluorophenyl)butoxy)-6-hydroxy-4-methoxy-3-nitrophenyl)ethanone To a stirred solution of Example 38c) (495 mg, 1.35 mmol) in Ac$_2$O (5 mL) at 0° C. under nitrogen was added NH$_4$NO$_3$ (108 mg, 1.35 mmol). The solution was allowed to warm to room temperature over 24 h. The reaction was quenched with the addition of H$_2$O (20 mL) and the product extracted with EtOAc (3×10 mL). The organics were pooled, dried over Na$_2$SO$_4$, filtered and concentrated in vacuo. The crude product was purified by flash chromatography (silica gel, diethyl ether/petroleum spirit, 3:17) to give the title compound as a yellow oil (132 mg, 24%). $^1$H NMR (300 MHz, CDCl$_3$) δ 12.83 (s, 1H), 7.19-7.14 (m, 2H), 7.01-6.95 (m, 2H), 4.04 (s, 3H), 3.98-3.93 (t, J=6.6 Hz, 2H), 3.03-2.95 (m, 1H), 2.82 (s, 3H), 2.11-1.97 (m, 2H), 1.31-1.28 (d, J=7.2 Hz, 3H), ESIMS m/z [M-H]$^+$ 410.2.

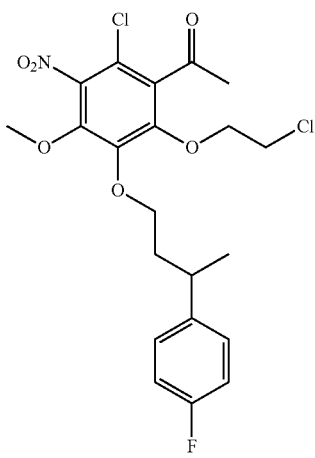 [SMILES: COc1c(OCCC(C)c2ccc(F)cc2)c(OCCCl)c(C(C)=O)c(Cl)c1[N+](=O)[O-]]

38e) 1-(2-chloro-6-(2-chloroethoxy)-5-(3-(4-fluorophenyl)butoxy)-4-methoxy-3-nitrophenyl)ethanone Example 38d) (267 mg, 0.65 mmol) and 1-bromo-2-chloroethane (600 µL, 7.21 mmol) were reacted as described under General Procedure D. The crude product was purified by flash chromatography (silica gel, diethyl ether/petroleum spirit 3:7) to give the title compound (294 mg, 95%). $^1$H NMR (300 MHz, CDCl$_3$) δ 7.18-7.13 (m, 2H), 7.02-6.96 (m, 2H), 4.29-4.25 (t, J=5.4 Hz, 2H), 4.01-3.92 (m, 5H), 3.69-3.65 (m, 2H), 2.98-2.88 (m, 1H), 2.54 (s, 3H), 2.09-2.01 (m, 2H), 1.31-1.29 (d, J=7.0 Hz, 3H), ESIMS m/z [M+H]$^+$ 474.2.

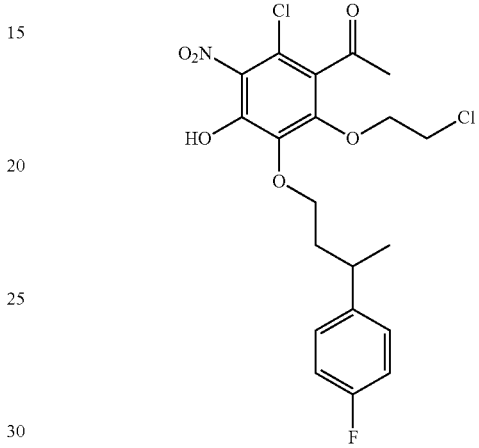

38f) 1-(2-Chloro-6-(2-chloroethoxy)-5-(3-(4-fluorophenyl)butoxy)-4-hydroxy-3-nitrophenyl)ethanone LiCl (223 mg, 5.27 mmol) was added to a solution of Example 38e) (293 mg, 0.62 mmol) in dry DMF (5 mL). The mixture was stirred at 90° C. for 16 h (TLC). The solution was concentrated in vacuo and the residue was dissolved in EtOAc (5 mL). The organics were washed with water, dried over MgSO$_4$ and concentrated in vacuo and the crude product was purified by flash chromatography (silica gel, ethyl acetate/petroleum spirit 2:8) to give the title compound (242 mg, 85%). $^1$H NMR (300 MHz, CDCl$_3$) δ 8.68 (s, 1H), 7.19-7.15 (m, 2H), 7.03-6.97 (m, 2H), 4.35-4.31 (m, 2H), 4.04-3.96 (m, 2H), 3.68-3.65 (m, 2H), 3.02-2.90 (m, 1H), 2.53 (s, 3H), 2.17-1.98 (m, 2H), 1.32-1.29 (d, J=7.0 Hz, 3H), ESIMS m/z [M-H]$^+$ 458.3.

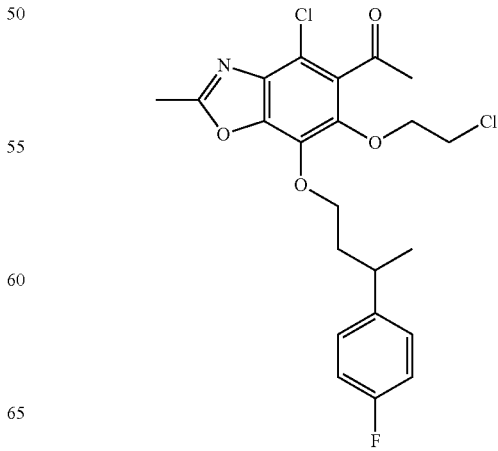

38g) 5-Acetyl-4-chloro-6-(2-chloroethoxy)-7-(3-(4-fluorophenyl)butoxy)-2-methyl-benzo[d]oxazole To a stirred solution 38f) (242 mg, 0.52 mmol) in dry EtOH (10 mL) under nitrogen was added SnCl$_2$.2H$_2$O (1.11 g, 4.92 mmol). The solution was heated at reflux for 4 h. The solution was concentrated in vacuo and the residue was dissolved in EtOAc (10 mL) and treated with sodium potassium tartrate (1M, 10 mL). The mixture was warmed at 50° C. until the layers visibly separated. The organic layer was separated and the aqueous further extracted with EtOAc (2×5 mL). The organics were pooled, dried over Na$_2$SO$_4$, filtered and concentrated in vacuo. The crude material was taken up in dry DMF (5 mL) and to this was added triethyl orthoacetate (5 mL, excess). The solution was stirred at reflux for 1 h. The solution was concentrated in vacuo and the residue was taken in CH$_2$Cl$_2$ (5 mL) and washed with water. The organic layer was dried over Na$_2$SO$_4$ and concentrated in vacuo. The crude product was purified by flash chromatography (silica gel, ethyl acetate/petroleum spirit 2:8) to give the title compound (151 mg, 64%). $^1$H NMR (300 MHz, CDCl$_3$) δ 7.21-7.16 (m, 2H), 7.02-6.96 (m, 2H), 4.36-4.19 (m, 4H), 3.74-3.71 (m, 2H), 3.30-3.11 (m, 1H), 2.62 (s, 3H), 2.58 (s, 3H) 2.16-1.97 (m, 2H), 1.34-1.31 (d, J=7.0 Hz, 3H), ESIMS m/z [M+H]$^+$ 454.2.

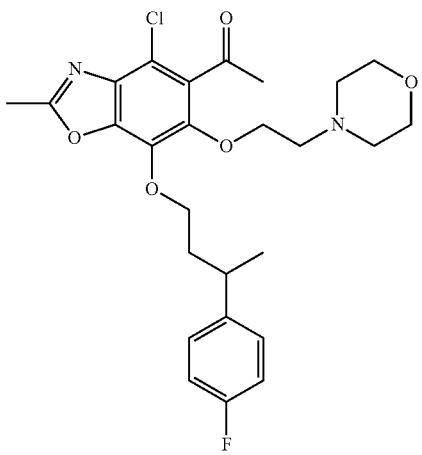 [SMILES: CC(=O)c1c(OCCN2CCOCC2)c(OCCC(C)c2ccc(F)cc2)c2oc(C)nc2c1Cl]

38h) 5-Acetyl-4-chloro-7-(3-(4-fluorophenyl)butoxy)-6-(2-(morpholin-4-yl)ethoxy)-2-methyl-benzo[d]oxazole To a stirred solution of Example 38g) (60.8 mg, 0.13 mmol) in dry DMF (5 mL) under N$_2$ were added morpholine (110 μL, 1.26 mmol) and NaI (114 mg, 0.76 mmol). The solution was heated to 60° C. for 24 h. After this time the reaction was cooled, diluted with EtOAc (10 mL) and washed with water (3×5 mL). The organic layer was dried over MgSO$_4$, concentrated in vacuo. The crude product was purified by flash chromatography (silica gel, methanol/ethyl acetate/petroleum spirit 2:18:80) to give the title compound (33 mg, 51%). $^1$H NMR (300 MHz, CDCl$_3$) δ 7.20-7.15 (m, 2H), 7.02-6.96 (m, 2H), 4.33-4.19 (m, 2H), 4.12-4.09 (m, 2H), 3.74-3.71 (m, 4H), 3.09-2.98 (m, 1H), 2.70-2.66 (m, 2H), 2.61 (s, 3H), 2.58 (s, 3H) 2.54-2.50 (m, 4H), 2.16-1.94 (m, 2H), 1.33-1.31 (d, J=7.0 Hz, 3H). ESIMS m/z [M+H]$^+$ 505.2.

Example 39

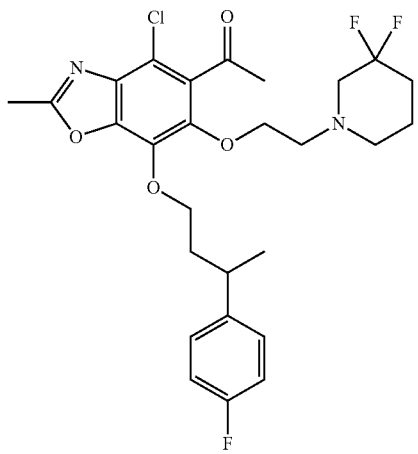 [SMILES: CC(=O)c1c(OCCN2CCCC(F)(F)C2)c(OCCC(C)c2ccc(F)cc2)c2oc(C)nc2c1Cl]

5-Acetyl-4-chloro-7-(3-(4-fluorophenyl)butoxy)-6-(2-(3,3-difluoropiperidin-1-yl)ethoxy)-2-methyl-benzo[d]oxazole To a stirred solution of Example 38g) (97 mg, 0.21 mmol) in dry acetone (3 mL) under N$_2$ was added NaI (352 mg, 2.35 mmol). The solution was heated to reflux for 3 days. After this time the reaction was cooled to room temperature and diluted with Et$_2$O (10 mL). The etheral layer was washed with water (3×5 mL), brine (5 mL), dried over Na$_2$SO$_4$, filtered and concentrated in vacuo. The crude material was dissolved in dry DMF (2 mL) and this solution was added to a stirred suspension of 3,3-difluoropiperidine hydrochloride (155 mg, 0.98 mmol), NaH (60% dispersion in oil, 38 mg, 0.93 mmol) and NaI (33 mg, 0.22 mmol) in dry DMF (5 mL). The solution was heated to 60° C. for 24 hours. After this time the reaction was cooled, diluted with sat. NH$_4$Cl(aq) and the product extracted with Et$_2$O (3×5 mL). The extracts were combined, dried over Na$_2$SO$_4$, filtered and concentrated in vacuo. The crude product was purified by flash chromatography (silica gel, methanol/ethyl acetate/petroleum spirit 2:18:80) to give the title compound (53 mg, 47%). NMR (300 MHz, CDCl$_3$) δ 7.20-7.15 (m, 2H), 7.01-6.95 (m, 2H), 4.33-4.19 (m, 2H), 4.12-4.09 (m, 2H), 3.74-3.71 (m, 4H), 3.09-2.98 (m, 1H), 2.70-2.66 (m, 2H), 2.61 (s, 3H), 2.58 (s, 3H) 2.54-2.50 (m, 4H), 2.16-1.94 (m, 2H), 1.33-1.31 (d, J=7.0 Hz, 3H), ESIMS m/z [M+H]$^+$ 539.2.

Example 40c

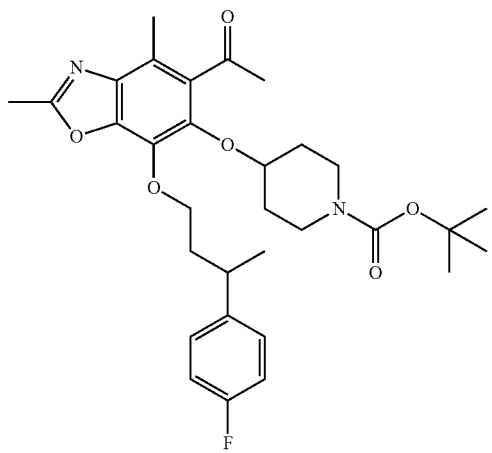 [SMILES: CC(=O)c1c(OC2CCN(C(=O)OC(C)(C)C)CC2)c(OCCC(C)c2ccc(F)cc2)c2oc(C)nc2c1C]

40a 5-Acetyl-2,4-dimethyl-7-(3-(4-fluorophenyl)butoxy)-6-[(N-Boc-piperidin-4-yl)oxy]-benzo[d]oxazole To a solution of Example 6b) (106 mg, 0.28 mmol) and tert-butyl 4-hydroxypiperidine-1-carboxylate (87 mg, 0.43 mmol) in anhydrous toluene (3 mL), under nitrogen, was added triphenylphosphine (96 mg, 0.36 mmol) and diisopropylazodicarboxylate (82 mg, 80 μL, 0.40 mmol). After stirring at room temperature for 4 h the reaction was quenched by addition of H$_2$O (20 mL), and the product extracted into DCM (3×20 mL). The pooled extracts were dried over Na$_2$SO$_4$ and concentrated in vacuo. The crude material was purified by column chromatography (silica gel, 1:1 EtOAc/petroleum spirit) giving a mixture of starting material and product. The residue was then taken up in Et$_2$O (25 mL) and washed with NaOH (1M, 3×25 mL), dried over Na$_2$SO$_4$ and concentrated in vacuo, yielding 114 mg (74%) of the title compound. $^1$H NMR (300 MHz, CDCl$_3$) δ 7.20-7.16 (m, 2H), 7.01-6.96 (m, 2H), 4.96 (m, 1H), 4.30-4.14 (m, 2H), 3.88-3.77 (m, 2H), 3.10-2.94 (m, 2H), 2.59 (s, 3H), 2.51 (s, 3H), 2.36 (s, 3H), 2.12-1.93 (m, 2H), 2.90-1.77 (m, 2H), 1.68-1.54 (m, 2H), 1.45 (s, 9H), 1.32 (d, J=6.9 Hz, 3H), MS (ES$^+$) m/z [M+H]$^+$ 555.2.

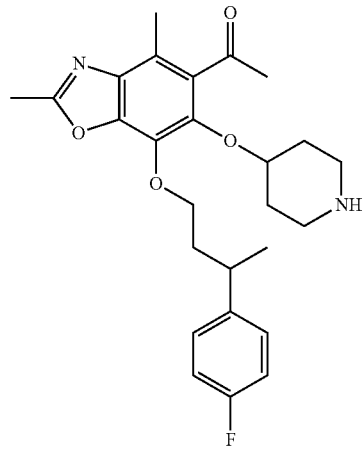 [SMILES: CC(=O)c1c(OC2CCNCC2)c(OCCC(C)c2ccc(F)cc2)c2oc(C)nc2c1C]

40b 5-Acetyl-2,4-dimethyl-7-(3-(4-fluorophenyl)butoxy)-6-[piperidin-4-yl]-benzo[d]oxazole A solution of Example 40a) (39 mg, 0.070 mmol), in DCM (0.5 mL) was cooled to 0° C. and trifluoroacetic acid (0.5 mL) was added dropwise. The solution was stirred at 0° C. for 0.08 h before diluting with EtOAc (20 mL) and washing with NaHCO$_3$ (2×20 mL), dried over MgSO$_4$, and concentrated in vacuo. The product was then taken up in DCM (20 mL) and washed with NaOH (1M, 20 mL), dried over MgSO$_4$ and concentrated in vacuo. The crude material was purified by column chromatography (silica gel, MeOH/DCM, 1:19 to 1:1) yielding the title compound (22 mg, 68%) as a clear yellow oil. $^1$H NMR (300 MHz, CDCl$_3$) δ 7.20-7.00 (m, 2H), 7.03-6.97 (m, 2H), 4.34 (br s, 1H), 4.23 (t, J=6.0 Hz, 2H), 3.40-3.07 (m, 4H), 3.01 (m, 1H), 2.58 (s, 3H), 2.51 (s, 3H), 2.35 (s, 3H), 2.22-1.93 (m, 6H), 1.33 (d, J=6.9 Hz, 3H), MS (ES$^+$) m/z [M+H]$^+$ 455.3.

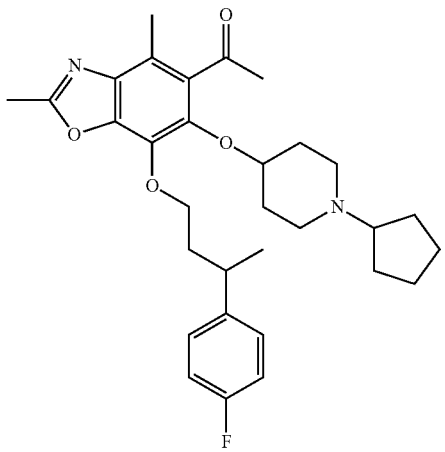 [SMILES: CC(=O)c1c(OC2CCN(C3CCCC3)CC2)c(OCCC(C)c2ccc(F)cc2)c2oc(C)nc2c1C]

40c 5-Acetyl-2,4-dimethyl-7-(3-(4-fluorophenyl)butoxy)-6-[1-cyclopentylpiperidin-4-yl)oxy]-benzo[d]oxazole To the solution of Example 40b) (20 mg, 0.042 mmol) in dry DMF (100 μL) at room temperature, cesium carbonate (21.5 mg, 0.066 mmol) was added and stirred for 10 min. Bromocyclopentane (9.4 μL, 0.083 mmol) was added and the resulting mixture was stirred for 5 d at room temperature. After completion, reaction was diluted with ethyl acetate and the organic layer was washed with water. The organic layer was separated, dried (MgSO$_4$) and concentrated in vacuo. The crude residue was purified by preparative thin layer chromatography (silica gel, EtOAc) to afford the title compound (8.5 mg, 37%) as a colourless oil. $^1$H NMR (300 MHz, CDCl$_3$) δ 7.26-7.17 (m, 2H), 7.01-6.96 (m, 2H), 4.26-4.10 (m, 3H), 3.10-3.02 (m, 1H), 2.87-2.81 (m, 1H), 2.58 (s, 3H), 2.51 (s, 3H), 2.36 (s, 3H), 2.17-1.41 (m, 18H), 1.27 (d, J=6.9 Hz, 3H), ESIMS m/z [M+H]$^+$ 523.2.

Example 41b

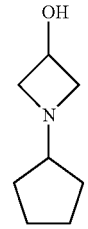

41a 1-Cyclopentylazetidin-3-ol

To a solution of 1-chloro-2,3-epoxypropane (784 μL, 10 mmol) and amino cyclopentane (988 μL, 10 mmol) in dry acetonitrile (10 ml), sodium bicarbonate (1.68 g, 20 mmol) was added, and the resulting mixture was heated to reflux until the completion of reaction (TLC, 5h). The reaction mixture was cooled to room temperature and filtered through Celite. Filtrate was concentrated in vacuo to afford an oily residue, which was purified by flash chromatography (silica gel, EtOAC/MeOH, 9:1) to furnish the title compound (565 mg, 40%) as a colourless oil. $^1$H NMR (300 MHz, CDCl$_3$) δ 4.40-4.32 (m, 1H), 3.58-3-53 (m, 2H), 2.90-2.84 (m, 2H), 2.72-2.65 (m, 1H), 1.70-1.23 (m, 8H), ESIMS m/z [M+H]$^+$ 142.5.

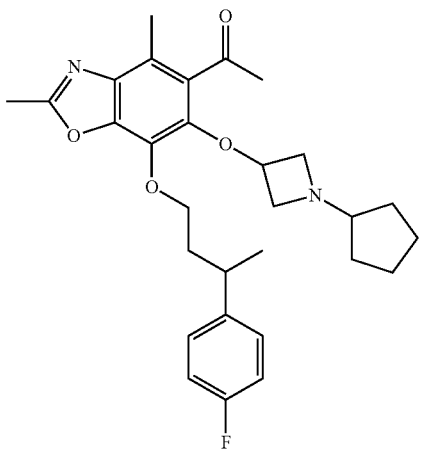 [SMILES: CC(=O)c1c(OC2CN(C3CCCC3)C2)c(OCCC(C)c2ccc(F)cc2)c2oc(C)nc2c1C]

41b 5-Acetyl-2,4-dimethyl-7-(3-(4-fluorophenyl)
butoxy)-6-[(1-cyclopentylazetidin-3-yl]oxyl-benzo
[d]oxazole To a solution of Example 6b) (100 mg, 0.16 mmol) and Example 41a) (57 mg, 0.24 mmol) in dry toluene (5 mL), polymer bound triphenylphosphene (70 mg, 0.21 mmol) and diisopropylazodicarboxylate (45 μL, 0.23 mmol) were added sequentially and resulting reaction mixture was stirred at 40° C. for 4 d under nitrogen. Polymer bound triphenylphosphene oxide was filtered and the filtrate was concentrated in vacuo. The crude residue was purified by preparative thin layer chromatography (silica gel, EtOAc) to give title compound (17 mg, 22%). $^1$H NMR (300 MHz, CDCl$_3$) δ 7.21-7.16 (m, 2H), 7.02-6.96 (m, 2H), 4.77-4.69 (m, 1H), 4.22-4.15 (m, 2H), 3.67-3.62 (m, 2H), 3.07-2.98 (m, 3H), 2.76-2.68 (m, 1H), 2.57 (s, 3H), 2.51 (s, 3H), 2.36 (s, 3H), 2.09-1.97 (m, 2H), 1.63-1.52 (m, 8H), 1.32 (d, J=6.9 Hz, 3H), ESIMS m/z [M+H]$^+$ 495.2.

Example 42

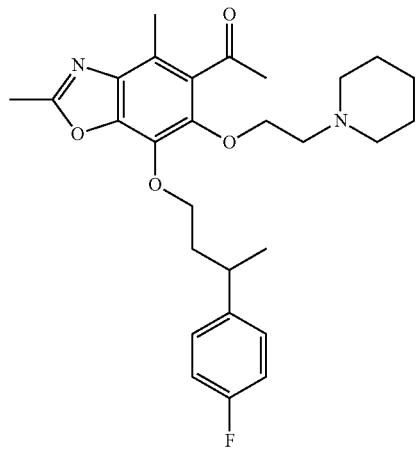 [SMILES: CC(=O)c1c(OCCN2CCCCC2)c(OCCC(C)c2ccc(F)cc2)c2oc(C)nc2c1C]

5-Acetyl-7-[3-(4-fluorophenyl)butoxy]-6-[2-(piperi-
din-1-yl)-ethoxy]-2,4-dimethyl-benzooxazole Example 10a) (106 mg, 0.22 mmol) was reacted with piperidine (189 mg, 2.22 mmol) as described under General Procedure E. The crude material was purified by flash chromatography (silica gel, Et$_2$O) to give the title compound (62 mg, 58%) as a light brown oil. $^1$H NMR (300 MHz, CDCl$_3$) δ 7.21-7.17 (m, 2H), 7.01-6.95 (m, 2H), 4.26-4.16 (m, 2H), 4.09 (t, J=6.0 Hz, 2H), 3.07 (m, 1H), 2.65 (t, J=6.0 Hz, 2H), 2.58 (s, 3H), 2.55 (s, 3H), 2.46-2.42 (m, 4H), 2.37 (s, 3H), 2.15-1.95 (m, 2H), 1.63-1.55 (m, 4H), 1.48-1.39 (m, 2H), 1.32 (d, J=6.9 Hz, 3H). ESIMS m/z [M+H]$^+$ 483.5.

Example 43

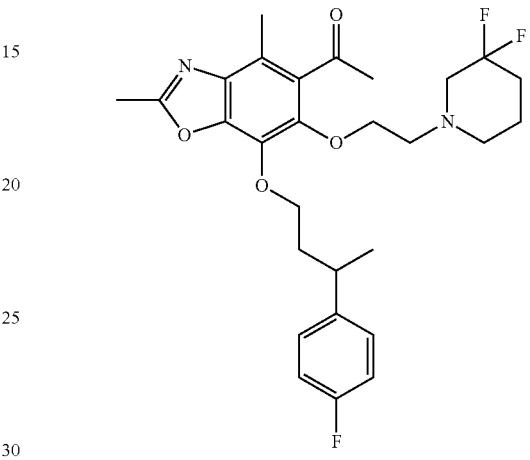

5-Acetyl-7-[3-(4-fluorophenyl)butoxy]-6-[2-(3,3-
difluoropiperidin-1-yl)-ethoxy]-2,4-dimethyl-ben-
zooxazole A solution of Example 10a) (102 mg, 0.21 mmol), NaH (26 mg, 0.64 mmol) and 3,3-difluoropiperidine hydrochloride (85 mg, 0.54 mmol) in DMF was heated to 65° C. overnight. The reaction mixture was cooled to room temperature, diluted with EtOAc and washed twice with water and brine, dried over MgSO$_4$ and concentrated in vacuo. The crude product was purified by column chromatography (silica gel, Et$_2$O/DCM, 1:9) to give the title compound as a clear, colourless oil (55 mg, 51%). $^1$H NMR (300 MHz, CDCl$_3$) δ 7.21-7.16 (m, 2H), 7.01-6.95 (m, 2H), 4.27-4.19 (m, 2H), 4.09 (t, J=5.6 Hz, 2H), 3.05 (m, 1H), 2.81-2.70 (m, 4H), 2.58 (s, 3H), 2.53 (s, 3H), 2.57-2.50 (m, 2H), 2.37 (s, 3H), 2.17-1.77 (m, 6H), 1.32 (d, J=6.9 Hz, 3H). ESIMS m/z [M+H]$^+$ 519.2.

Biological Activity

The effectiveness of the generated compounds in blocking the Kv1.3 current was assayed on CHO cells stably expressing hKv1.3. Cells were grown in F12 Kaighns' medium supplemented with 10% fetal calf serum, 2 mM L-glutamine, 1 mM Na$^+$ pyruvate, 100 units/ml penicillin, 100 Fg/ml streptomycin and 500 μg/ml G418 (to keep them under selection pressure). Kv1.3 currents were measured using the whole-cell configuration of the patch-clamp technique and were evoked by 500 ms depolarising voltage pulses to +40 mV from a holding potential of −80 mV at 30 sec intervals. Cells were continuously bathed in Ringers solution containing (mM): 160 NaCl, 4.5 KCl, 2.5 CaCl$_2$, 1 MgCl$_2$, 10 HEPES, pH 7.4, 290-310 mOsm. The internal (pipette) solution contained (mM): 134 KF, 2 MgCl$_2$, 10 HEPES, 10 EGTA (pH 7.2, 290-310 mOsm). Series resistance compensation (60-80%) was applied when the peak current amplitude exceeded 2 nA. Compounds initially dissolved in DMSO were diluted in bath solution (final DMSO concentration 0.5%) and applied directly to the recording chamber at increasing concentrations allowing ample time for steady state block to be achieved between each concentration. Each compound was tested at 4-5 different concentrations in triplicate. IC$_{50}$ values were determined by fitting the average normalised reduction of the current integral to the Hill equation.

The doses that have a half-maximal effect on the Kv1.3 current for a range of compounds of the invention tested for binding to Kv1.3 are depicted below in Table 1.

TABLE 1

| Example Numbers | Structure | IC$_{50}$ (Kv1.3) |
|---|---|---|
| 1i | 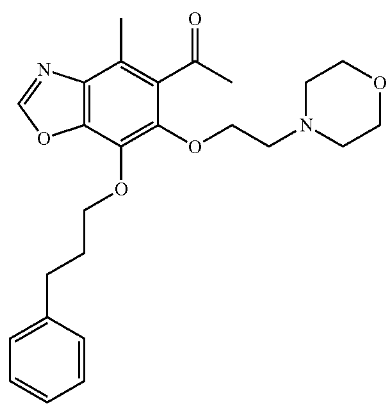 [SMILES: CC(=O)c1c(OCCN2CCOCC2)c(OCCCc2ccccc2)c2ocnc2c1C] | 50-200 nM |
| 2d | 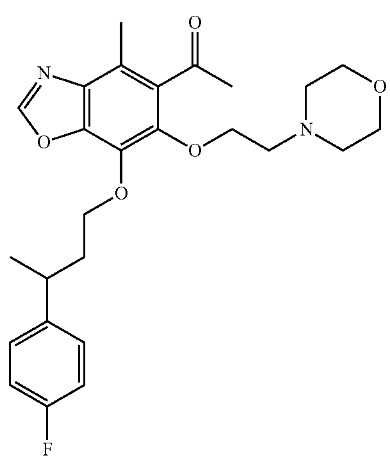 [SMILES: CC(=O)c1c(OCCN2CCOCC2)c(OCCC(C)c2ccc(F)cc2)c2ocnc2c1C] | <50 nM |
| 3 | 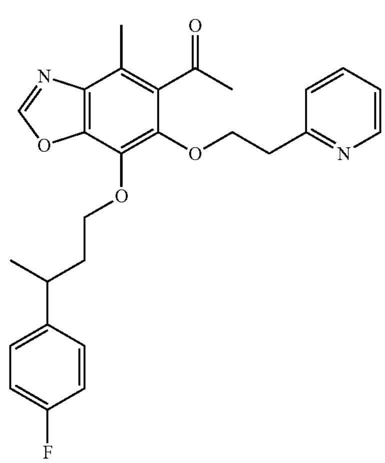 [SMILES: CC(=O)c1c(OCCc2ccccn2)c(OCCC(C)c2ccc(F)cc2)c2ocnc2c1C] | <50 nM |

TABLE 1-continued
| Example Numbers | Structure | IC$_{50}$ (Kv1.3) |
|---|---|---|
| 4b | 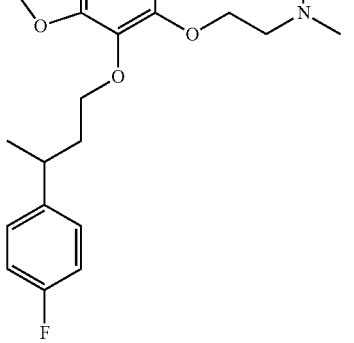 | 200-1000 nM |
| 5 | 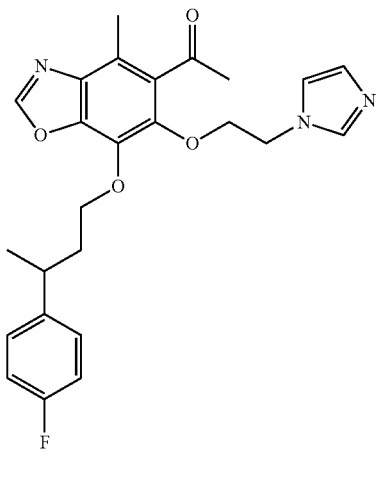 [SMILES: CC(=O)c1c(OCCn2ccnc2)c(OCCC(C)c2ccc(F)cc2)c2ocnc2c1C] | <50 nM |
| 6c | 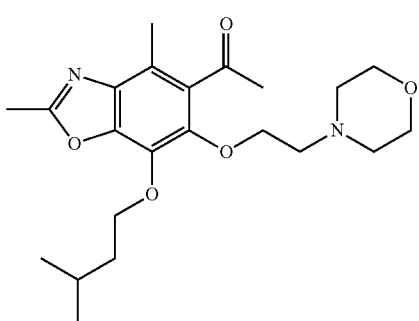 | <50 nM |

TABLE 1-continued

| Example Numbers | Structure | IC$_{50}$ (Kv1.3) |
|---|---|---|
| 7 | 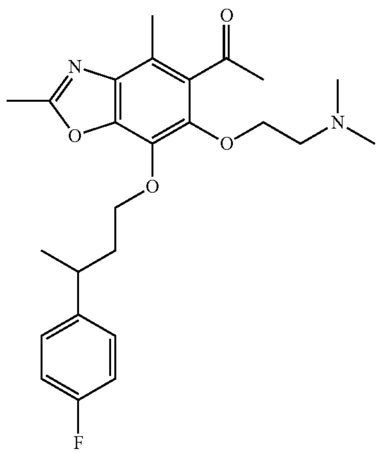 | 200-1000 nM |
| 8 | 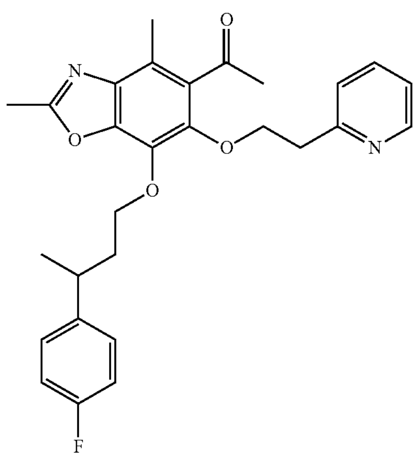 [SMILES: CC(=O)c1c(OCCc2ccccn2)c(OCCC(C)c2ccc(F)cc2)c2oc(C)nc2c1C] | <50 nM |
| 9 | 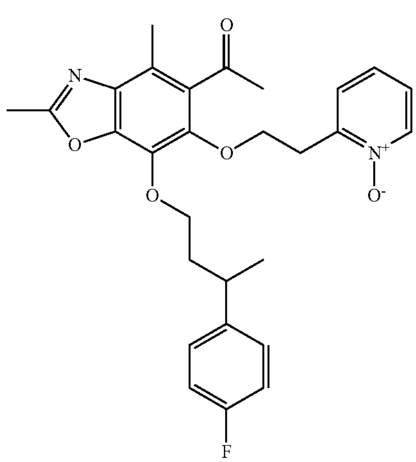 [SMILES: CC(=O)c1c(OCCc2cccc[n+]2[O-])c(OCCC(C)c2ccc(F)cc2)c2oc(C)nc2c1C] | 200-1000 nM |

TABLE 1-continued

| Example Numbers | Structure | IC$_{50}$ (Kv1.3) |
| --- | --- | --- |
| 10b | 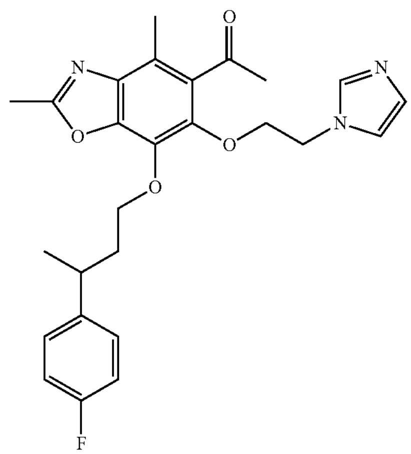 [SMILES: CC(=O)c1c(OCCn2ccnc2)c(OCCC(C)c2ccc(F)cc2)c2oc(C)nc2c1C] | 50-200 nM |
| 11a | 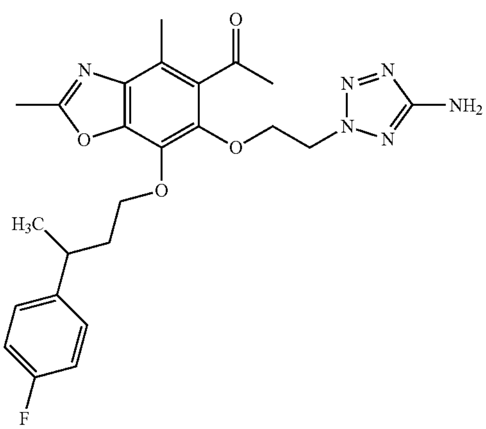 [SMILES: CC(=O)c1c(OCCn2nnc(N)n2)c(OCCC(C)c2ccc(F)cc2)c2oc(C)nc2c1C] | <50 nM |
| 11b | 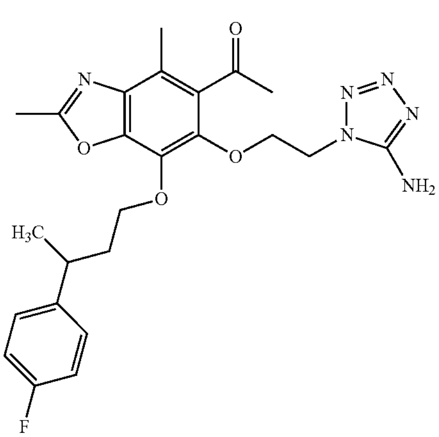 [SMILES: CC(=O)c1c(OCCn2nnnc2N)c(OCCC(C)c2ccc(F)cc2)c2oc(C)nc2c1C] | 50-200 nM |

TABLE 1-continued

| Example Numbers | Structure | IC$_{50}$ (Kv1.3) |
|---|---|---|
| 12 | 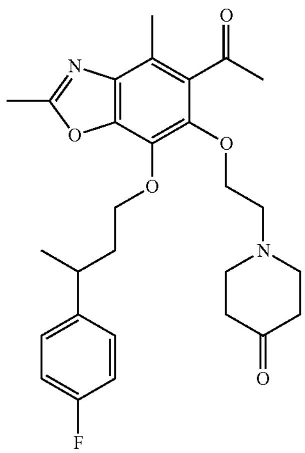 [SMILES: CC(=O)c1c(OCCN2CCC(=O)CC2)c(OCCC(C)c2ccc(F)cc2)c2oc(C)nc2c1C] | 50-200 nM |
| 13 | 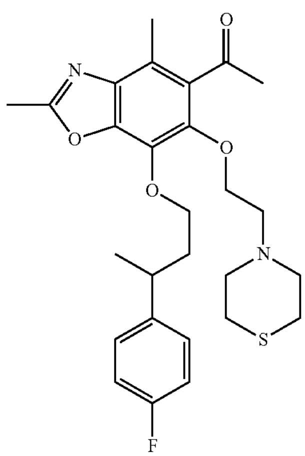 [SMILES: CC(=O)c1c(OCCN2CCSCC2)c(OCCC(C)c2ccc(F)cc2)c2oc(C)nc2c1C] | <50 nM |
| 14 | 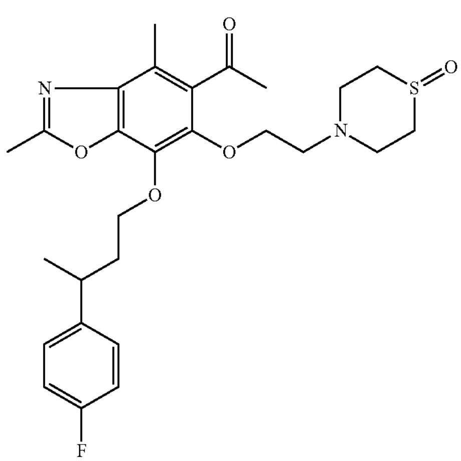 [SMILES: CC(=O)c1c(OCCN2CCS(=O)CC2)c(OCCC(C)c2ccc(F)cc2)c2oc(C)nc2c1C] | 50-200 nM |

TABLE 1-continued
| Example Numbers | Structure | IC$_{50}$ (Kv1.3) |
|---|---|---|
| 15 | 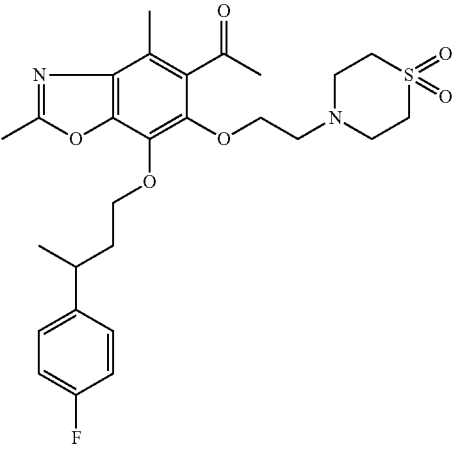 [SMILES: CC(=O)c1c(OCCN2CCS(=O)(=O)CC2)c(OCCC(C)c2ccc(F)cc2)c2oc(C)nc2c1C] | <50 nM |
| 16 | 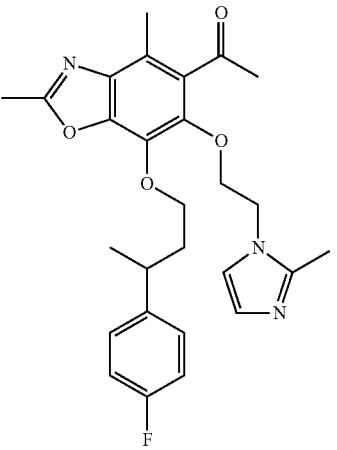 | 50-200 nM |
| 17a and 17b | 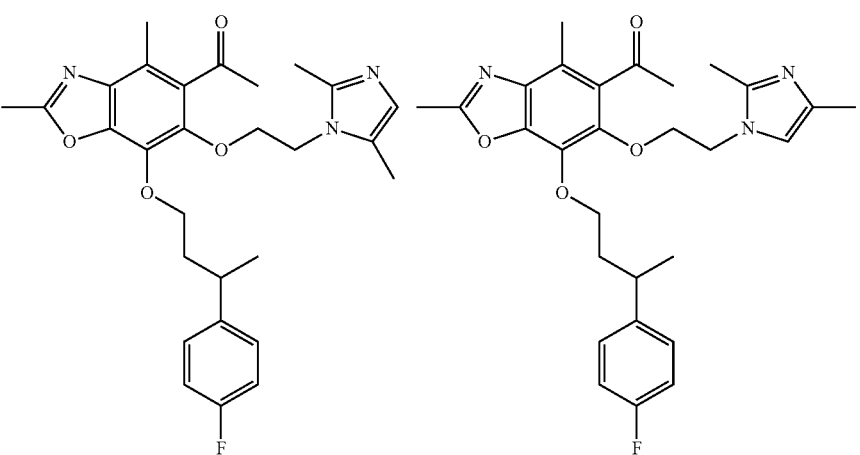 | 50-200 nM |

TABLE 1-continued

| Example Numbers | Structure | $IC_{50}$ (Kv1.3) |
|---|---|---|
| 18 | 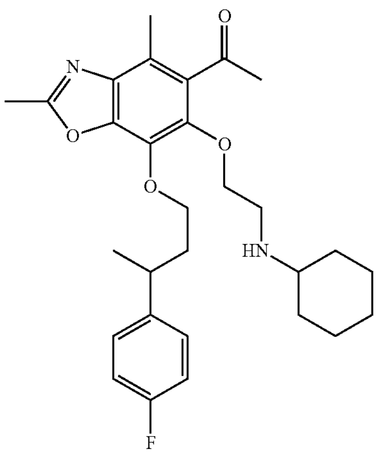 [SMILES: CC(=O)c1c(OCCNC2CCCCC2)c(OCCC(C)c2ccc(F)cc2)c2oc(C)nc2c1C] | <50 nM |
| 19 | 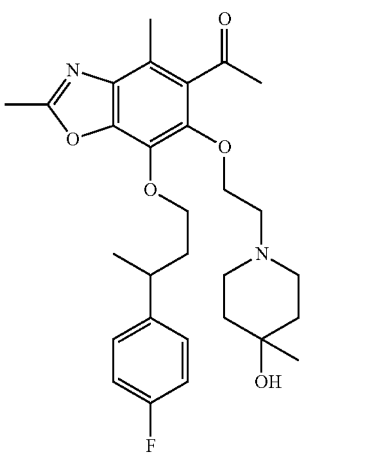 | 50-200 nM |
| 20 | 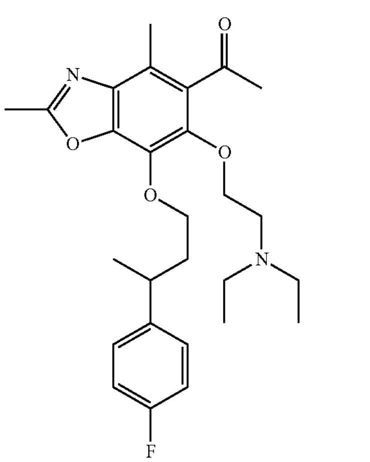 [SMILES: CCN(CC)CCOc1c(C(C)=O)c(C)c2nc(C)oc2c1OCCC(C)c1ccc(F)cc1] | 200-1000 nM |

TABLE 1-continued
| Example Numbers | Structure | IC$_{50}$ (Kv1.3) |
|---|---|---|
| 21 | 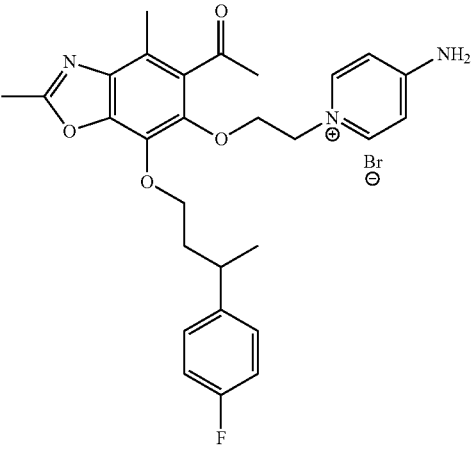 [SMILES: CC(=O)c1c(OCC[n+]2ccc(N)cc2)c(OCCC(C)c2ccc(F)cc2)c2oc(C)nc2c1C ; [Br-]] | >1000 nM |
| 22 | 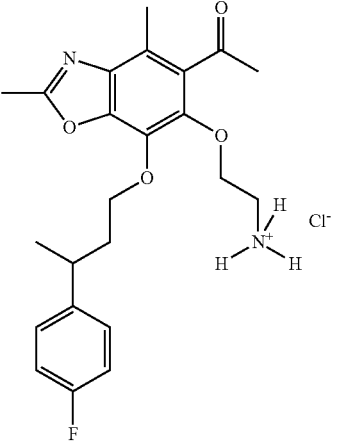 [SMILES: CC(=O)c1c(OCC[NH3+])c(OCCC(C)c2ccc(F)cc2)c2oc(C)nc2c1C ; [Cl-]] | 200-1000 nM |
| 23 | 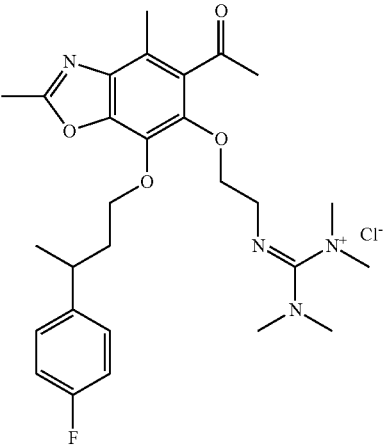 | 200-1000 nM |

TABLE 1-continued
| Example Numbers | Structure | IC$_{50}$ (Kv1.3) |
|---|---|---|
| 24 | 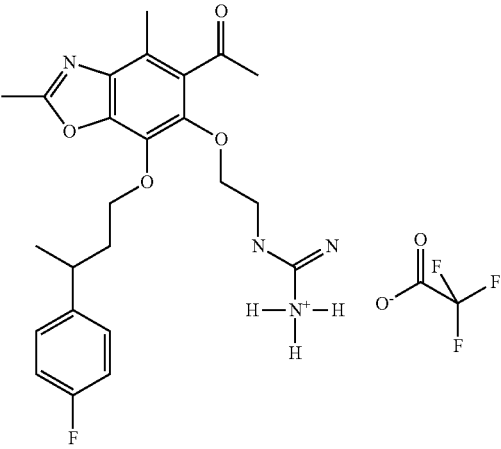 [SMILES: CC(=O)c1c(OCCNC(=N)[NH3+])c(OCCC(C)c2ccc(F)cc2)c2oc(C)nc2c1C ; O=C([O-])C(F)(F)F] | |
| 25 | 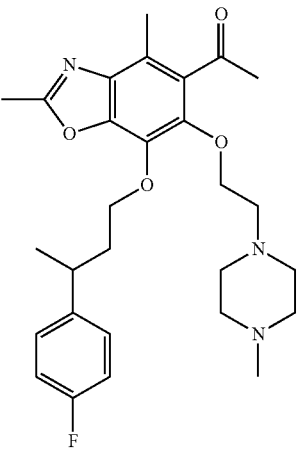 [SMILES: CC(=O)c1c(OCCN2CCN(C)CC2)c(OCCC(C)c2ccc(F)cc2)c2oc(C)nc2c1C] | 200-1000 nM |
| 26 | 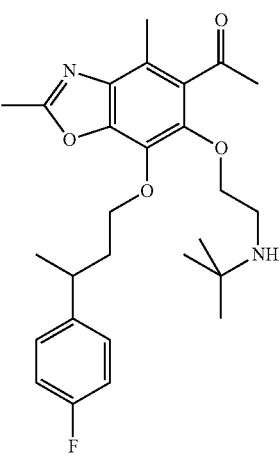 [SMILES: CC(=O)c1c(OCCNC(C)(C)C)c(OCCC(C)c2ccc(F)cc2)c2oc(C)nc2c1C] | 200-1000 nM |

TABLE 1-continued
| Example Numbers | Structure | IC$_{50}$ (Kv1.3) |
|---|---|---|
| 27 | 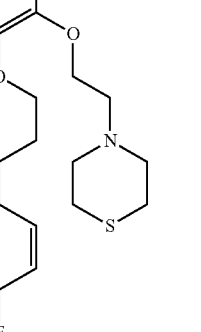 | <50 nM |
| 28c | 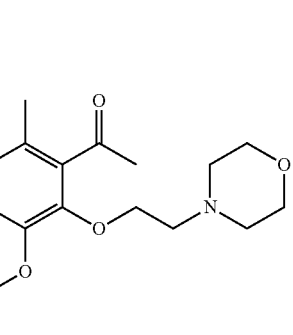 | 50-200 nM |
| 29 | 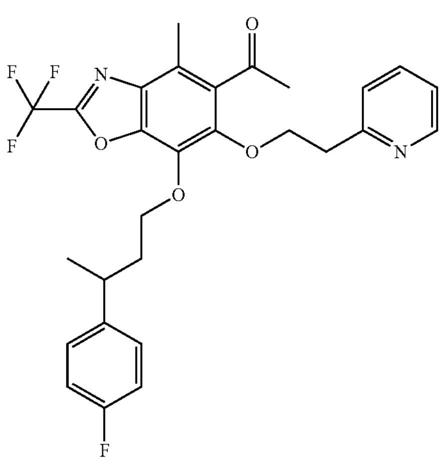 [SMILES: CC(=O)c1c(OCCc2ccccn2)c(OCCC(C)c2ccc(F)cc2)c2oc(C(F)(F)F)nc2c1C] | 50-200 nM |

TABLE 1-continued

| Example Numbers | Structure | IC$_{50}$ (Kv1.3) |
|---|---|---|
| 30c | 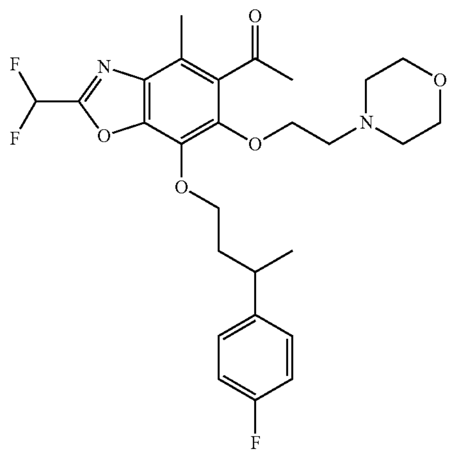 [SMILES: CC(=O)c1c(OCCN2CCOCC2)c(OCCC(C)c2ccc(F)cc2)c2oc(C(F)F)nc2c1C] | 50-200 nM |
| 31b | 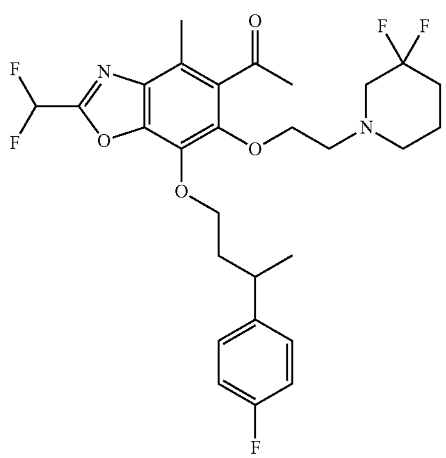 [SMILES: CC(=O)c1c(OCCN2CCCC(F)(F)C2)c(OCCC(C)c2ccc(F)cc2)c2oc(C(F)F)nc2c1C] | <50 nM |
| 32c | 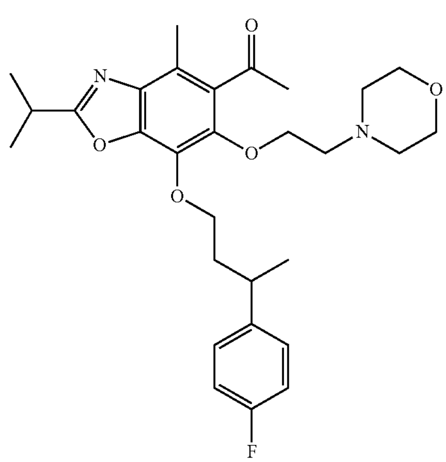 [SMILES: CC(=O)c1c(OCCN2CCOCC2)c(OCCC(C)c2ccc(F)cc2)c2oc(C(C)C)nc2c1C] | <50 nM |

TABLE 1-continued

| Example Numbers | Structure | IC$_{50}$ (Kv1.3) |
|---|---|---|
| 33b | 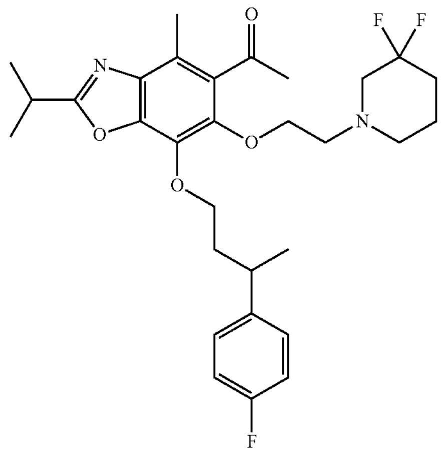 [SMILES: CC(=O)c1c(OCCN2CCCC(F)(F)C2)c(OCCC(C)c2ccc(F)cc2)c2oc(C(C)C)nc2c1C] | 50-200 nM |
| 34 | 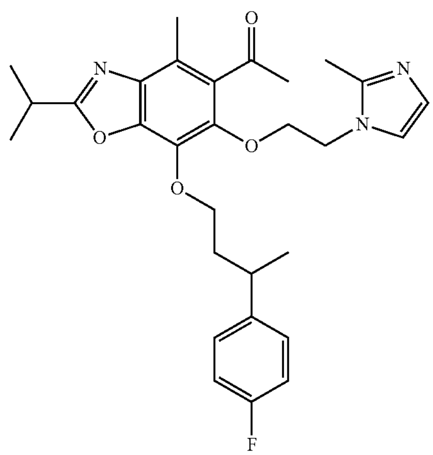 [SMILES: CC(=O)c1c(OCCn2ccnc2C)c(OCCC(C)c2ccc(F)cc2)c2oc(C(C)C)nc2c1C] | 200-1000 nM |
| 35d | 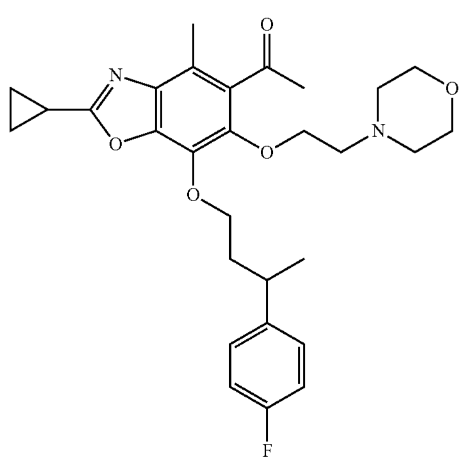 [SMILES: CC(=O)c1c(OCCN2CCOCC2)c(OCCC(C)c2ccc(F)cc2)c2oc(C3CC3)nc2c1C] | 50-200 nM |

TABLE 1-continued

| Example Numbers | Structure | IC$_{50}$ (Kv1.3) |
|---|---|---|
| 36b | 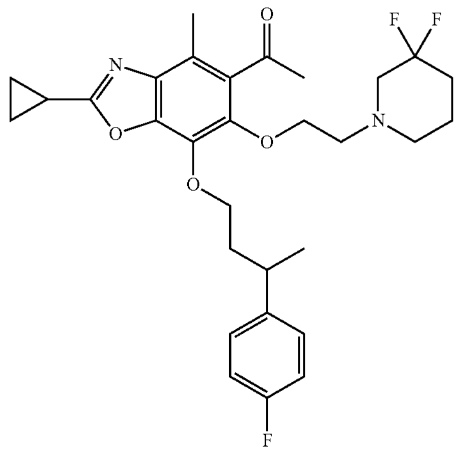 | 50-200 nM |
| 37j | 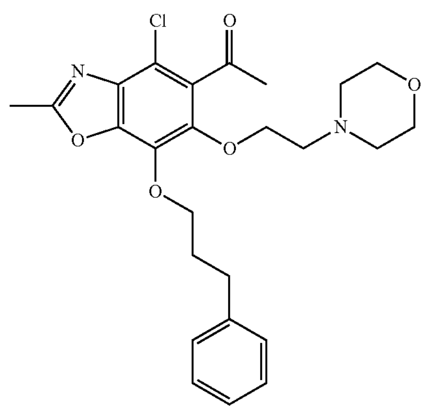 [SMILES: CC(=O)c1c(OCCN2CCOCC2)c(OCCCc2ccccc2)c2oc(C)nc2c1Cl] | 200-1000 nM |
| 38h | 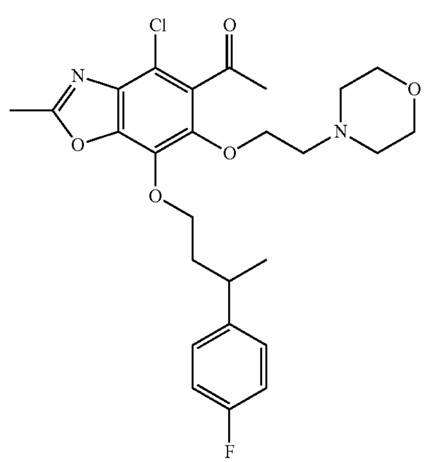 | 50-200 nM |

TABLE 1-continued
| Example Numbers | Structure | IC$_{50}$ (Kv1.3) |
|---|---|---|
| 39 | 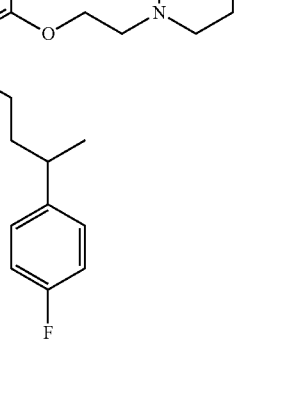 | 50-200 nM |
| 40c | 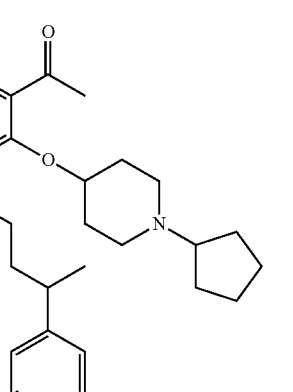 | 50-200 nM |
| 41b | 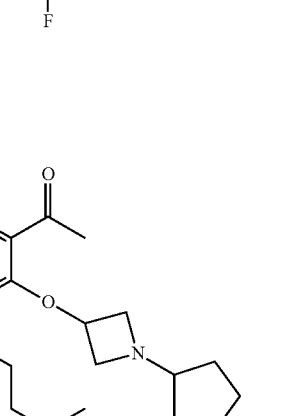 | 50-200 nM |

| Example Numbers | Structure | IC$_{50}$ (Kv1.3) |
|---|---|---|
| 42 | 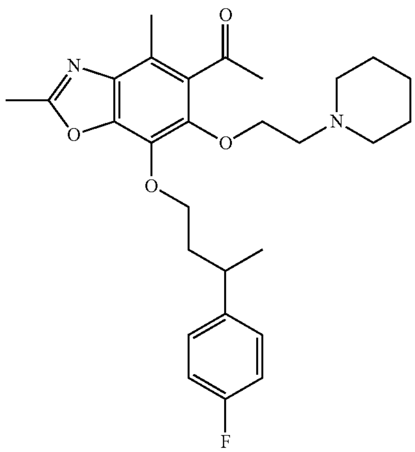 [SMILES: CC(=O)c1c(OCCN2CCCCC2)c(OCCC(C)c2ccc(F)cc2)c2oc(C)nc2c1C] | <50 nM |
| 43 | 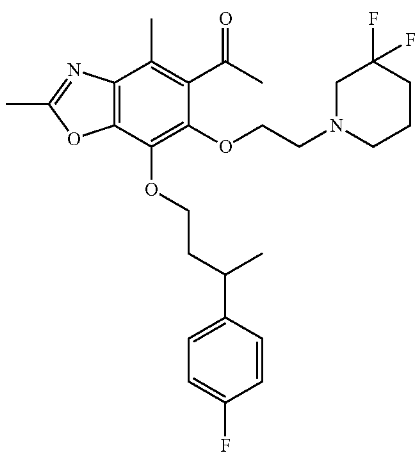 [SMILES: CC(=O)c1c(OCCN2CCCC(F)(F)C2)c(OCCC(C)c2ccc(F)cc2)c2oc(C)nc2c1C] | <50 nM |

Potency and Selectivity Data

IC$_{50}$ values for inhibition of Kv1.3 currents were determined as described above. IC$_{50}$ values for inhibition of Kv1.1 and Kv1.5 currents were determined by the method above using Chinese Hamster Ovary (CHO) cells stably transfected with hKv1.1 and hKv1.5.

Example 13

Potency for Kv1.3<50 nM
Selectivity for Kv1.3 over Kv1.1: 15-fold, selectivity for Kv1.3 over Kv1.5: 11-fold.

Example 18

Potency for Kv1.3<50 nM
Selectivity for Kv1.3 over Kv1.1: 11-fold, selectivity for Kv1.3 over Kv1.5: 12-fold.

Example 31b

Potency for Kv1.3<50 nM
Selectivity for Kv1.3 over Kv1.1: 21-fold, selectivity for Kv1.3 over Kv1.5: 29-fold.

Example 42

Potency for Kv1.3<50 nM

Selectivity for Kv1.3 over Kv1.1: 25-fold, selectivity for Kv1.3 over Kv1.5: 24-fold.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

What is claimed is:

1. A compound of formula (I) or salt thereof,

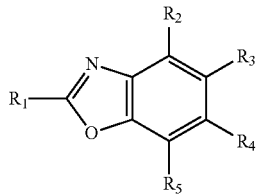

wherein
R₁ is selected from the group consisting of hydrogen, halo, optionally substituted lower alkyl, optionally substituted aryl, optionally substituted heteroaryl, optionally substituted heterocyclyl, optionally substituted C₃₋₇ cycloalkyl, —OR, —C(O)R, —C(O)OR and —OC(O)R (where R is selected from the group consisting of optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from the group consisting of hydrogen, lower alkyl and aryl);

R₂ is selected from the group consisting of halo, cyano, optionally substituted lower alkyl, optionally substituted aryl, optionally substituted heteroaryl, optionally substituted heterocyclyl, optionally substituted C₃₋₇ cycloalkyl, —OR, —C(O)R, —C(O)OR, —OC(O)R (where R is selected from the group consisting of hydrogen, optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from the group consisting of hydrogen, lower alkyl and aryl);

R₃ is selected from the group consisting of:
—C(O)R₆, where R₆ is selected from the group consisting of lower haloalkyl, optionally substituted alkyl, optionally substituted C₃₋₇ cycloalkyl, optionally substituted heterocyclyl, optionally substituted heteroaryl, optionally substituted aryl, —OR, —C(O)R, —C(O)OR, —OC(O)R, SR (where R is selected from the group consisting of hydrogen, optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl), —C(O)NR'R'', —NR'C(O)R'' and —NR'R'' (where R' and R'' are independently selected from the group consisting of hydrogen or lower alkyl);
—S(O)ₘR''' (where m is 1 or 2 and R''' is independently selected from the group consisting of NH₂, dialkylamino, monoalkylamino, optionally substituted alkyl, optionally substituted C₃₋₇ cycloalkyl, optionally substituted heterocyclyl, optionally substituted heteroaryl and optionally substituted aryl);
—SR (where R is selected from the group consisting of hydrogen, optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl);
—C(OH)HR (where R is selected from the group consisting of hydrogen, optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl);
optionally substituted heterocyclyl;
optionally substituted heteroaryl;
NR'R'' (where R' and R'' are independently selected from the group consisting of hydrogen and lower alkyl);
NR'C(O)R'' (where R' and R'' are independently selected from the group consisting of hydrogen and lower alkyl); and
—C(O)NR'R'' (where R' and R'' are independently selected from the group consisting of hydrogen and lower alkyl);

R₄ is XR₇, where X is —O—, —S—, —CH₂—, —CH=CH—, —C≡C— or NR' (where R' is selected from the group consisting of hydrogen and lower alkyl) and where R₇ is selected from the group consisting of optionally substituted alkyl, optionally substituted alkenyl, optionally substituted aryl, optionally substituted heteroaryl, optionally substituted heterocyclyl, optionally substituted alkynyl, optionally substituted C₃₋₇ cycloalkyl, optionally substituted C₄₋₇ cycloalkenyl, —C(O)R, (where R is selected from hydrogen, optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl), and —C(O)NR'R'(where R' and R'' are independently selected from the group consisting of hydrogen and lower alkyl); and R₅ is selected from the group consisting of optionally substituted alkyl, optionally substituted aryl, optionally substituted heteroaryl, optionally substituted heterocyclyl, —OR, —C(O)R, —C(O)OR, —OC(O)R, —C(O)NRR', —NRC(O)R', —NRR', SR, SOR, SO₂R, and SO₂NRR' (where R is selected from the group consisting of optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl and R' is selected from the group consisting of hydrogen, optionally substituted alkyl, optionally substituted alkenyl, optionally substituted alkynyl, optionally substituted C₃₋₇ cycloalkyl, optionally substituted heterocyclyl, optionally substituted heteroaryl, and optionally substituted aryl).

2. A compound according to claim 1 or salt thereof, wherein R₃ is selected from the group consisting of:
—C(O)—R₆ where R₆ is lower haloalkyl, optionally substituted alkyl, optionally substituted C₃₋₇ cycloalkyl, optionally substituted heterocyclyl, optionally substituted heteroaryl, optionally substituted aryl or NR'R'' (where R' and R'' are independently selected from the group consisting of hydrogen, lower alkyl, and optionally substituted heteroaryl);
—S(O)ₘR''' (where m is 1 or 2 and where R''' is independently selected from the group consisting of NH₂, dialkylamino, monoalkylamino, optionally substituted alkyl, optionally substituted C₃₋₇ cycloalkyl, optionally substituted heterocyclyl, optionally substituted heteroaryl and optionally substituted aryl); and
—C(OH)HR (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

3. A compound according to claim 1 or salt thereof, wherein $R_4$ is $OR_7$ where $R_7$ is selected from the group consisting of optionally substituted alkyl, optionally substituted alkenyl, optionally substituted aryl, optionally substituted heteroaryl, optionally substituted heterocyclyl, optionally substituted alkynyl, optionally substituted $C_{3-7}$ cycloalkyl, optionally substituted $C_{4-7}$ cycloalkenyl, —C(O)R, (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and —C(O)NR'R" (where R' and R" are independently selected from the group consisting of hydrogen and lower alkyl).

4. A compound according to claim 1 or salt thereof, wherein $R_4$ is selected from the group consisting of a terminally substituted $C_{1-10}$ alkoxy, optionally substituted heteroaryloxy, optionally substituted heterocyclyloxy, and optionally substituted cycloalkyloxy.

5. A compound according to claim 1 or salt thereof, wherein $R_5$ is defined by the group —Y-L-$R_8$ wherein:
Y is selected from the group consisting of a single bond, —O—, —C(O)—, —S—, —NR'''—, —C(O)NR'''—, and —NR'''C(O)— (where R''' is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);
L is a divalent linker group of 2-6 atoms in length selected from the group consisting of optionally substituted $C_{2-6}$ alkylene, optionally substituted $C_{3-6}$ cycloalkylene, optionally substituted $C_{2-6}$ alkenylene, and optionally substituted $C_{2-6}$ alkynylene; and
$R_8$ is selected from the group consisting of optionally substituted aryl, optionally substituted heterocyclyl, optionally substituted heteroaryl, optionally substituted aryloxy, optionally substituted heterocyclyloxy, optionally substituted heteroaryloxy, —NHR''' (where R''' is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and SR''' (where is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

6. A compound according to claim 1, which is a compound of formula (Ia) or salt thereof,

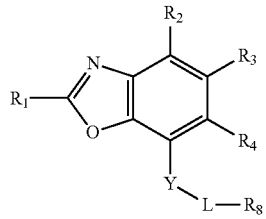

(Ia)

wherein:
$R_1$ is selected from the group consisting of hydrogen, halo, optionally substituted lower alkyl, optionally substituted aryl, optionally substituted heteroaryl, optionally substituted heterocyclyl, optionally substituted $C_{3-7}$ cycloalkyl, —OR, —C(O)R, —C(O)OR, —OC(O)R (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from the group consisting of hydrogen, lower alkyl and aryl);
$R_2$ is selected from the group consisting of halo, cyano, optionally substituted lower alkyl, optionally substituted aryl, optionally substituted heteroaryl, optionally substituted heterocyclyl, optionally substituted $C_{3-7}$ cycloalkyl, —OR, —C(O)R, —C(O)OR, —OC(O)R (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'''R'''', —NR'''C(O)R'''' and —NR'''R'''' (where R''' and R'''' are independently selected from the group consisting of hydrogen, lower alkyl and aryl);
$R_3$ is selected from the group consisting of:
—C(O)$R_6$, where $R_6$ is selected from the group consisting of lower haloalkyl, optionally substituted alkyl, optionally substituted $C_{3-7}$ cycloalkyl, optionally substituted heterocyclyl, optionally substituted heteroaryl, optionally substituted aryl, —OR, —C(O)R, —C(O)OR, —OC(O)R, SR, (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from the group consisting of hydrogen and lower alkyl);
—S(O)$_m$R''' (where m is 1 or 2 and R''' is independently selected from the group consisting of $NH_2$, dialkylamino, monoalkylamino, optionally substituted alkyl, optionally substituted $C_{3-7}$ cycloalkyl, optionally substituted heterocyclyl, optionally substituted heteroaryl and optionally substituted aryl);
—SR (where and R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);
—C(OH)HR (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);
optionally substituted heterocyclyl;
optionally substituted heteroaryl;
NR'R" (where R' and R" are independently selected from the group consisting of hydrogen and lower alkyl);
NR'C(O)R" (where R' and R" are independently selected from the group consisting of hydrogen and lower alkyl); and
—C(O)NR'R" (where R' and R" are independently selected from the group consisting of hydrogen and lower alkyl);
$R_4$ is $XR_7$, where X is —O—, —S—, —CH$_2$—, —CH=CH—, —C≡C— or NR' (where R' is selected from the group consisting of hydrogen and lower alkyl) and where $R_7$ is selected from the group consisting of optionally substituted alkyl, optionally substituted alkenyl, optionally substituted aryl, optionally substituted heteroaryl, optionally substituted heterocyclyl, optionally substituted alkynyl, optionally substituted $C_{3-7}$ cycloalkyl, optionally substituted $C_{4-7}$ cycloalkenyl, —C(O)R (where R is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and —C(O)NR'R" (where R' and R" are independently selected from the group consisting of hydrogen and lower alkyl);
Y is selected from the group consisting of a single bond, —O—, —C(O)—, —S—, —NR'''—, —C(O)NR'''—, and —NR'''C(O)— (where R''' is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);
L is a divalent linker group of 2-6 atoms in length selected from the group consisting of optionally substituted $C_{2-6}$ alkylene, optionally substituted $C_{3-6}$ cycloalkylene, optionally substituted $C_{2-6}$ alkenylene, and optionally substituted $C_{2-6}$ alkynylene; and
$R_8$ is selected from the group consisting of optionally substituted aryl, optionally substituted heterocyclyl, optionally substituted heteroaryl, optionally substituted aryloxy, optionally substituted heterocyclyloxy, optionally substituted heteroaryloxy, —NHR''' (where R''' is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and SR''' (where R''' is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).
7. A compound according to claim 4 or salt thereof, wherein Y is O or single bond;
L is optionally substituted $C_{2-6}$ alkylene or optionally substituted $C_{3-6}$ cycloalkylene; and
$R_8$ is selected from the group consisting of optionally substituted aryl, optionally substituted heterocyclyl, optionally substituted heteroaryl, optionally substituted aryloxy, optionally substituted heterocyclyloxy, optionally substituted heteroaryloxy, —NHR''' (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), or SR''' (where is selected from the group consisting of hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

8. A compound according to claim 5 or salt thereof, wherein Y is O, L is optionally substituted $C_{2-6}$ alkylene or optionally substituted $C_{3-6}$ cycloalkylene, and $R_8$ is optionally substituted aryl, optionally substituted heteroaryl, or optionally substituted heterocyclyl.

9. A compound according to claim 1 or salt thereof, wherein $R_1$ is selected from the group consisting of $C_{1-4}$ alkyl, $C_{3-6}$ cycloalkyl, and halo $C_{1-3}$ alkyl.

10. A compound according to claim 1 or salt thereof, wherein $R_2$ is $C_{1-4}$ alkyl or halo.

11. A compound according to claim 1 or salt thereof, wherein $R_3$ is selected from the group consisting of —C(O) $C_1$-$C_3$ alkyl, —C(OH)$C_1$-$C_3$ alkyl, —S(O)$_2$ $C_1$-$C_3$alkyl, —C(O)NH($C_1$-$C_3$ alkyl), —C(O)N($C_1$-$C_3$ alkyl)$_2$, and —C(O)halo $C_{2-4}$ alkyl.

12. A compound according to claim 1 or salt thereof, wherein $R_4$ is $C_{1-4}$ alkoxy terminally substituted by a group selected from the group consisting of NH$_2$, dialkylamino, monodialkylamino, guanidino, optionally substituted aryl, optionally substituted heteroaryl, and optionally substituted heterocyclyl group; optionally substituted heterocyclyloxy; and optionally substituted heteroaryloxy.

13. A compound according to claim 1 or salt thereof, wherein $R_4$ is selected from the group consisting of:

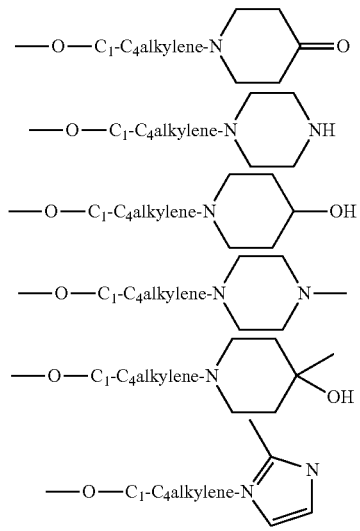

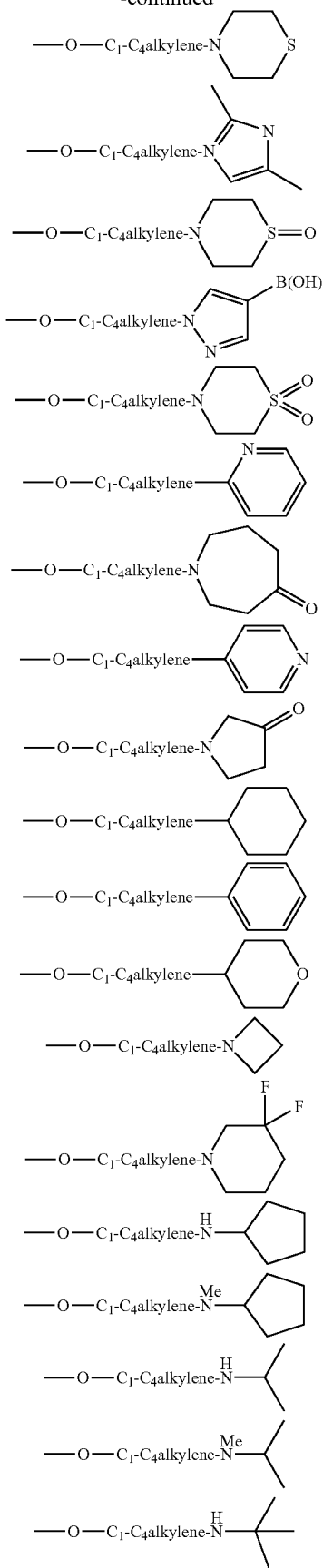
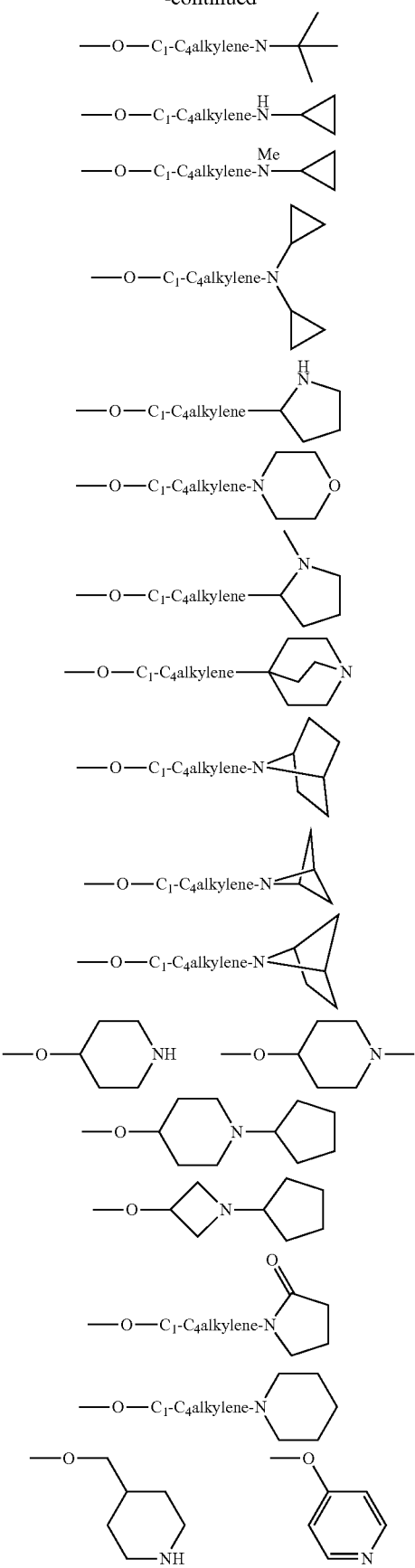

-continued
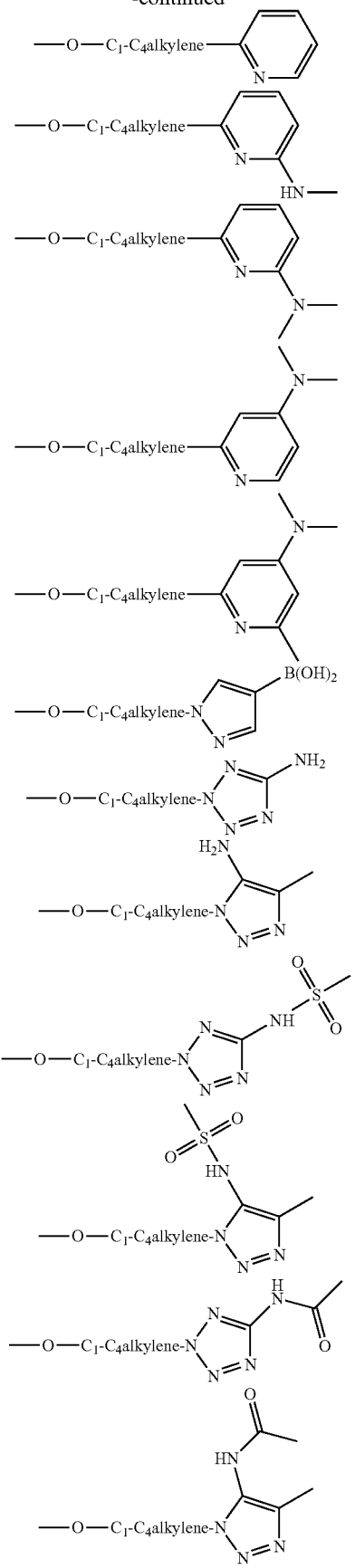
-continued
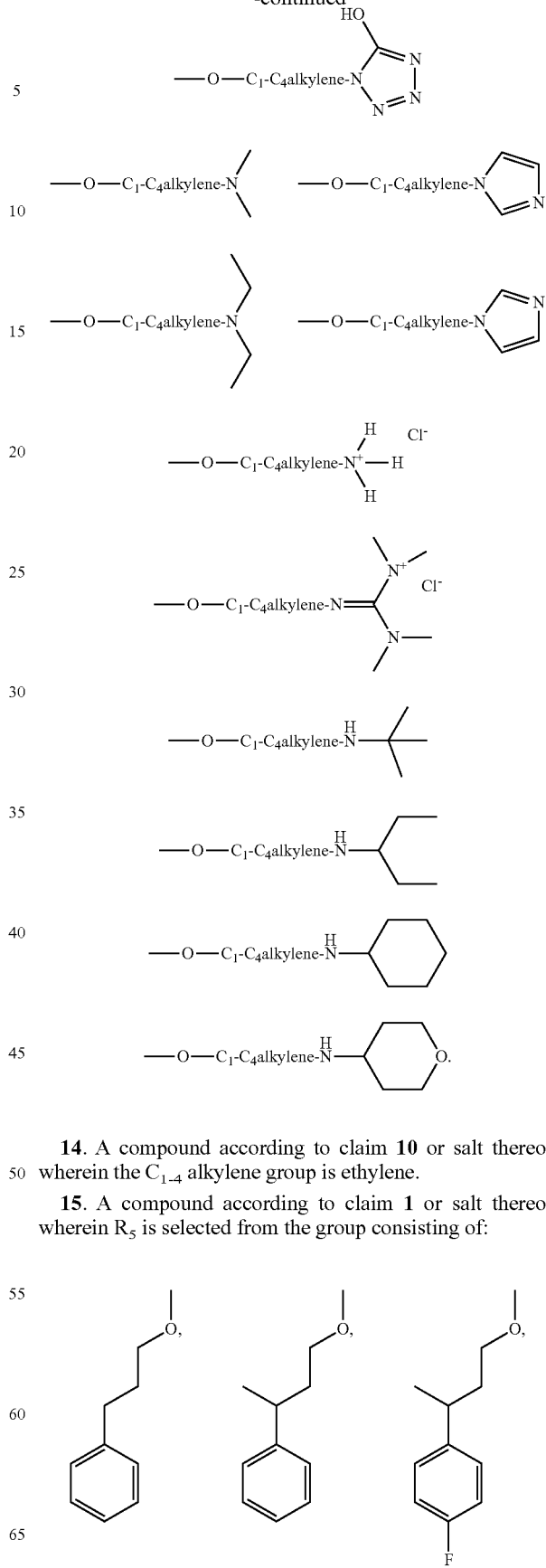
14. A compound according to claim 10 or salt thereof, wherein the $C_{1-4}$ alkylene group is ethylene.
15. A compound according to claim 1 or salt thereof, wherein $R_5$ is selected from the group consisting of:

-continued
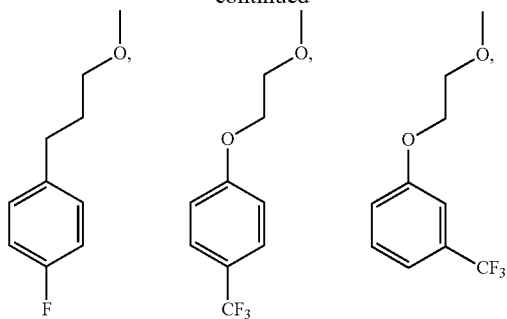
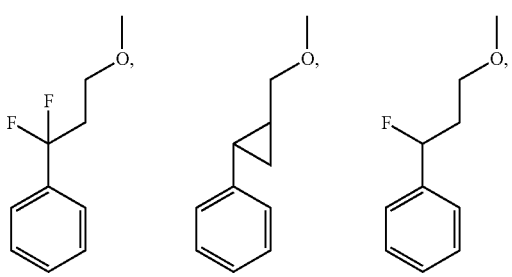
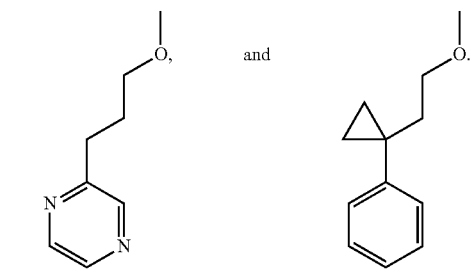
16. A compound according to claim 15 or salt thereof, wherein $R_5$ is
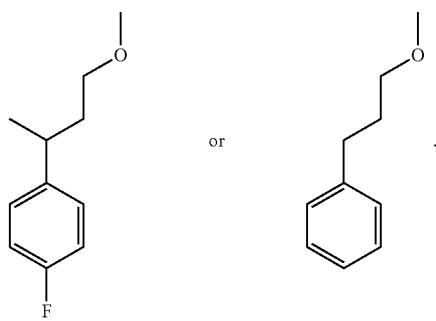
17. A compound according to claim 1 selected from the group consisting of:
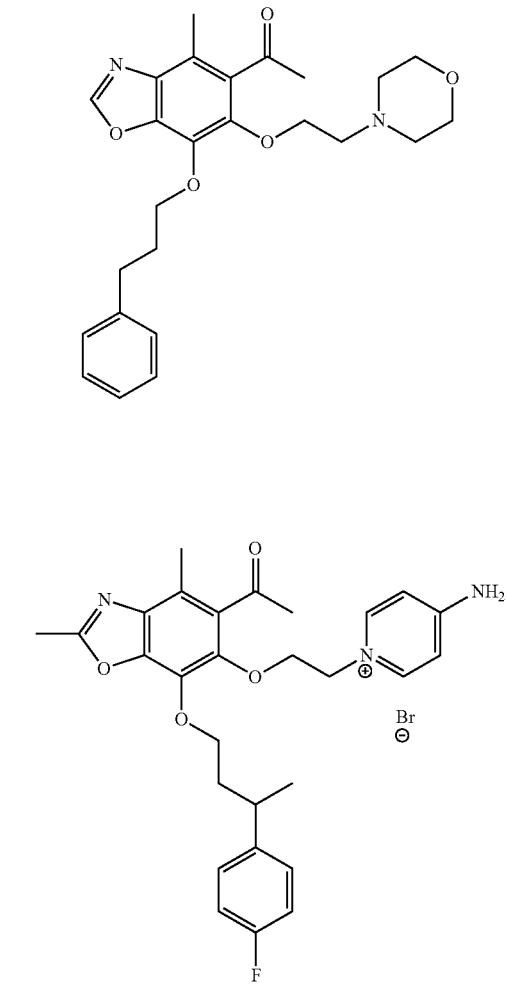
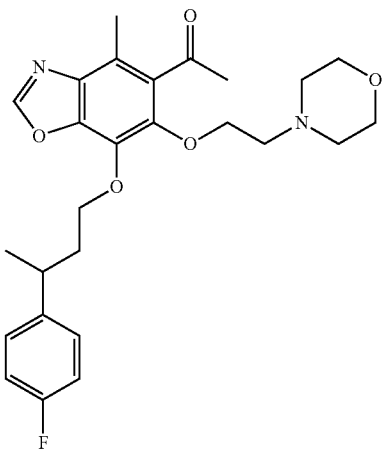

125
-continued
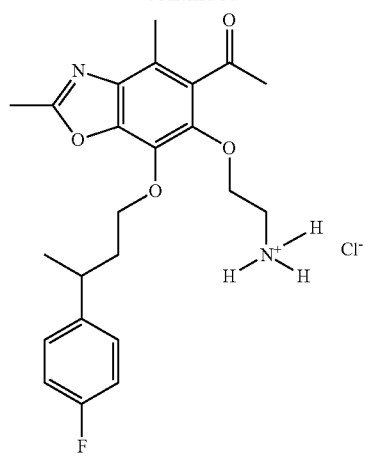
126
-continued
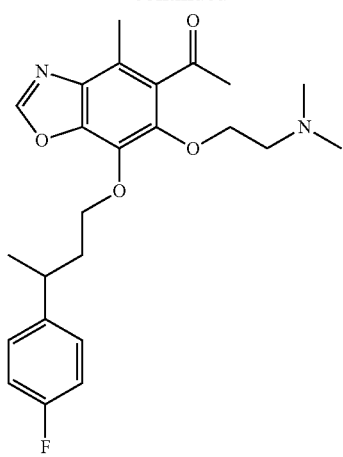
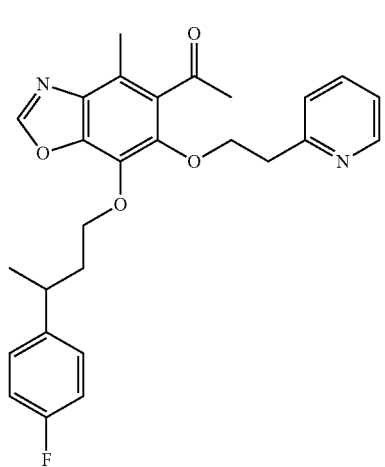
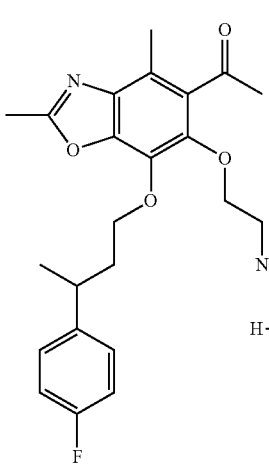
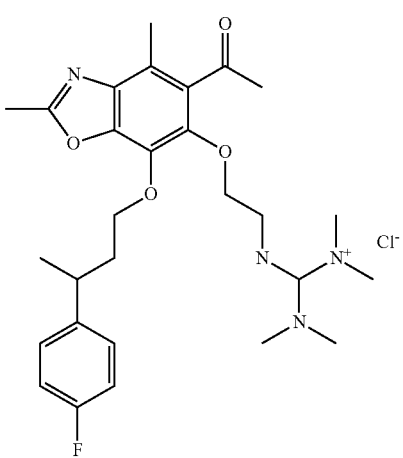
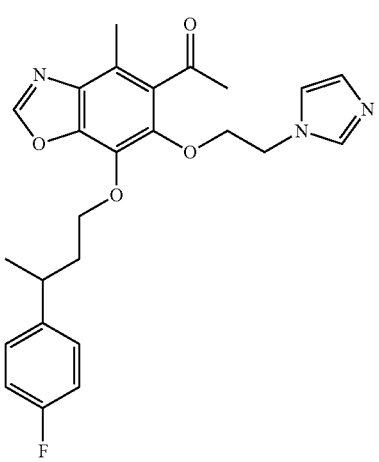

127
-continued
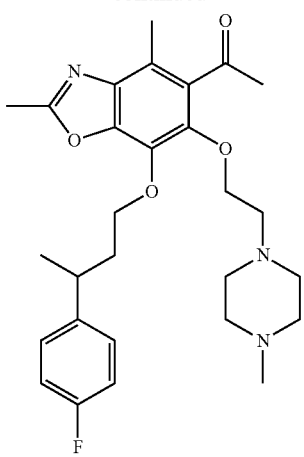
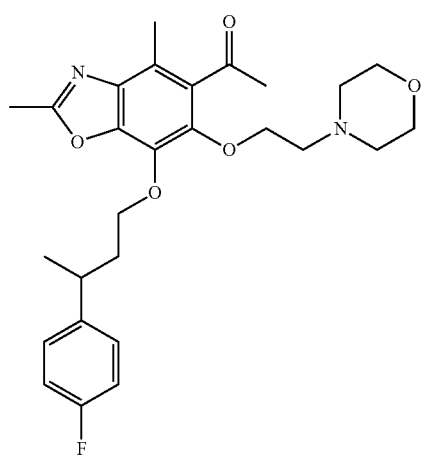
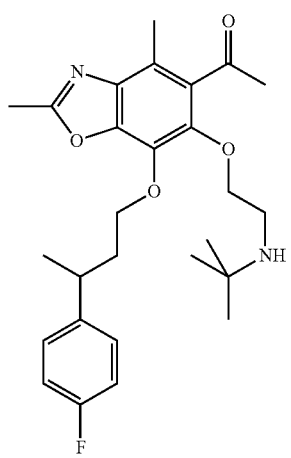
128
-continued
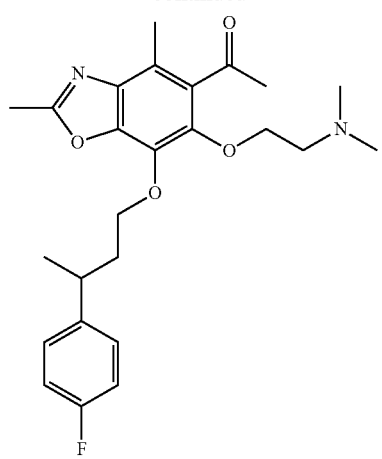
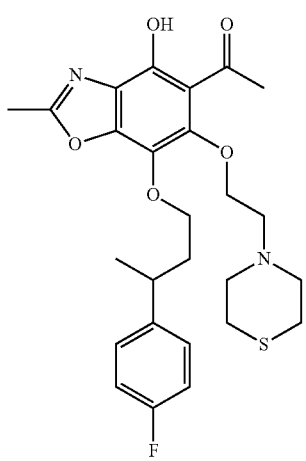
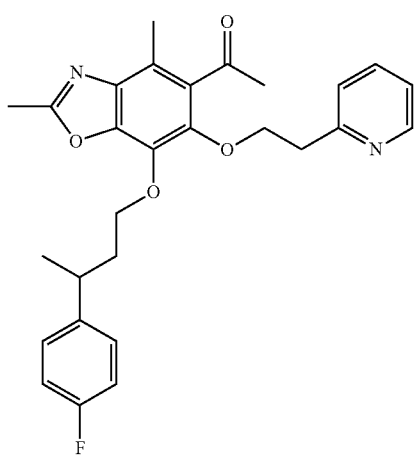

| 129 | 130 |
|---|---|
| -continued | -continued |
| 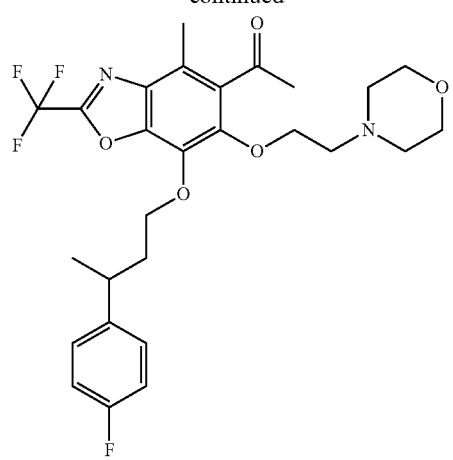 | 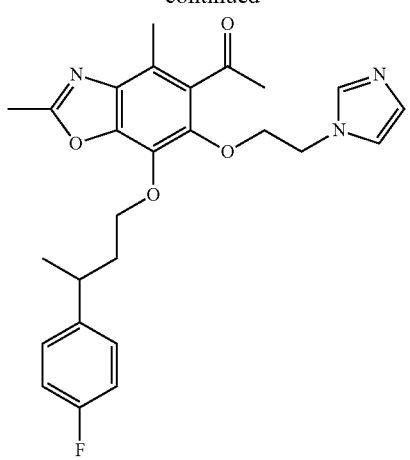 |
| 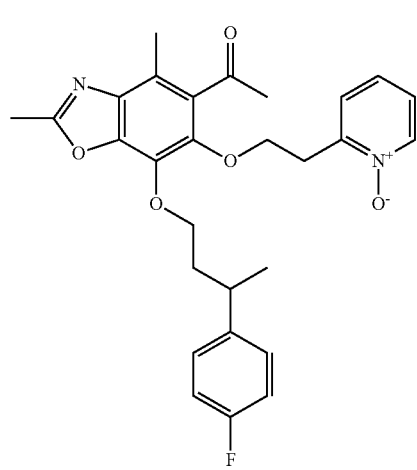 | 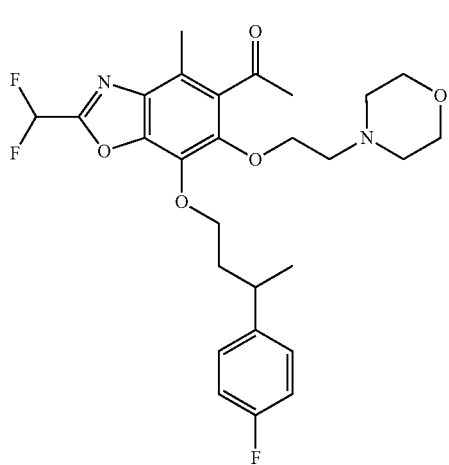 |
| 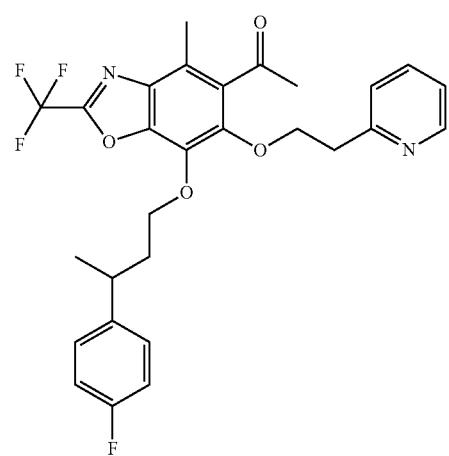 | 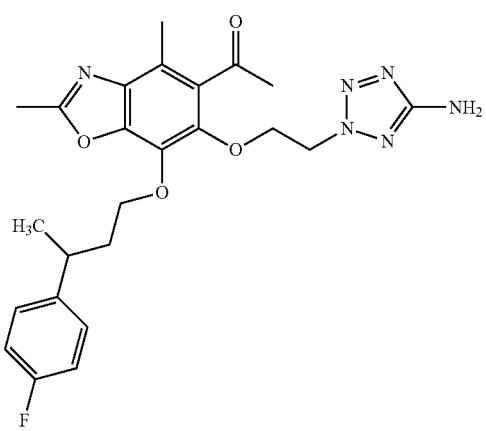 |

131
-continued
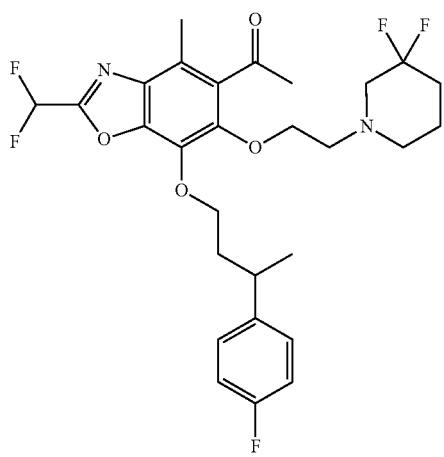
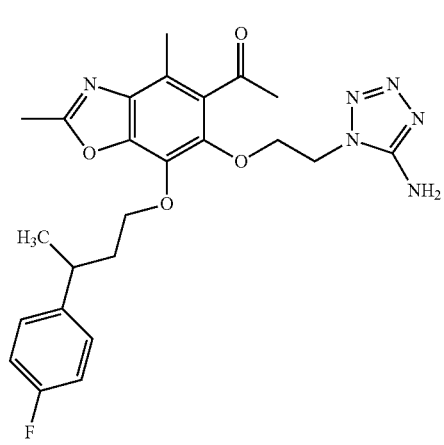
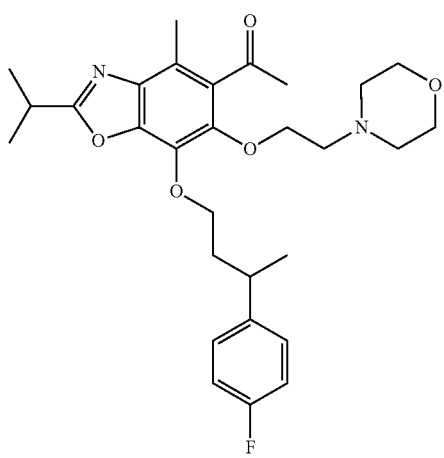
132
-continued
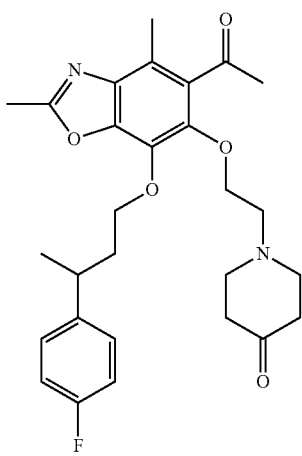
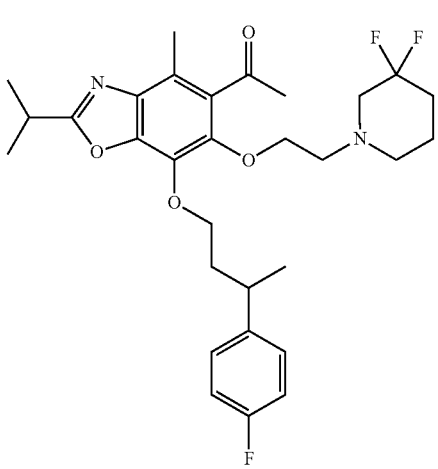
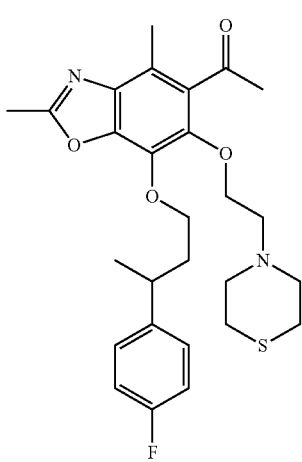

133
-continued
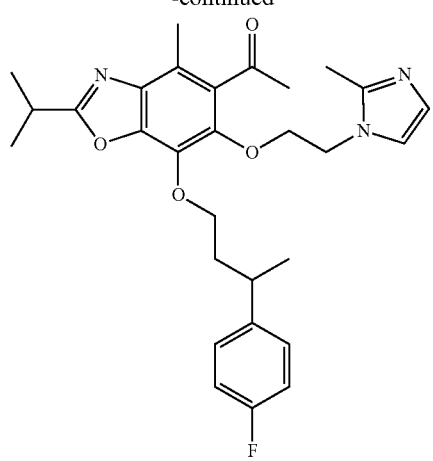
134
-continued
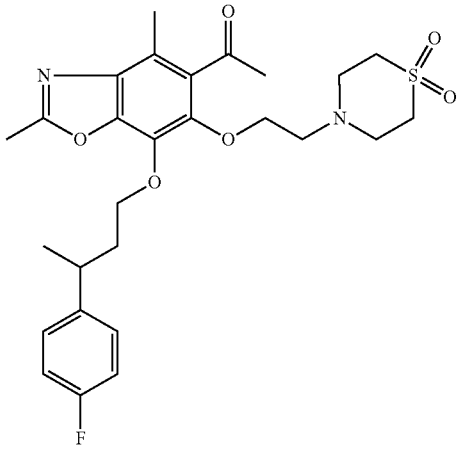
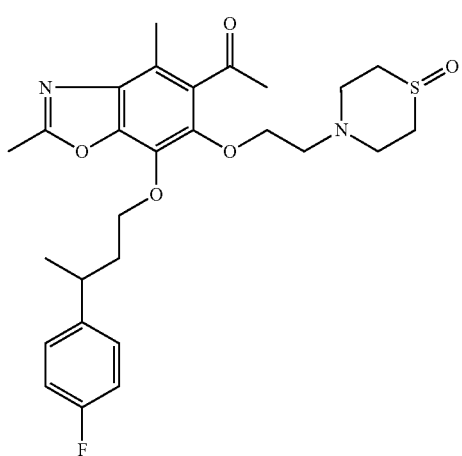
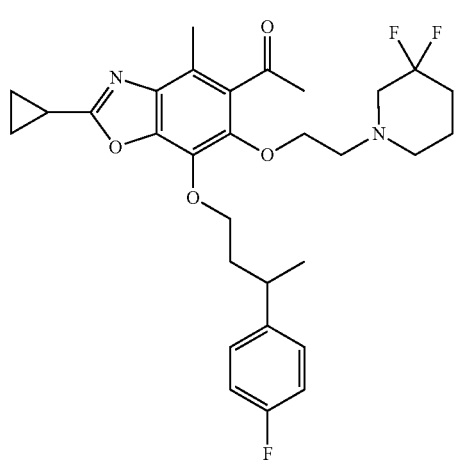
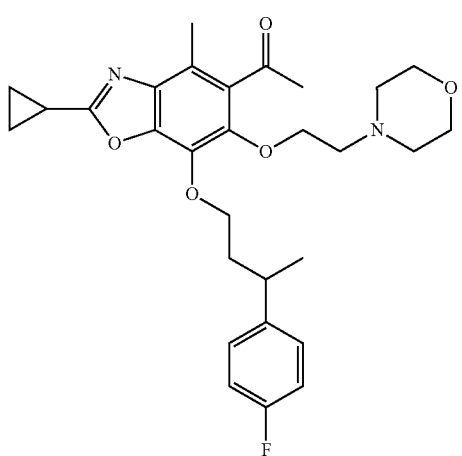
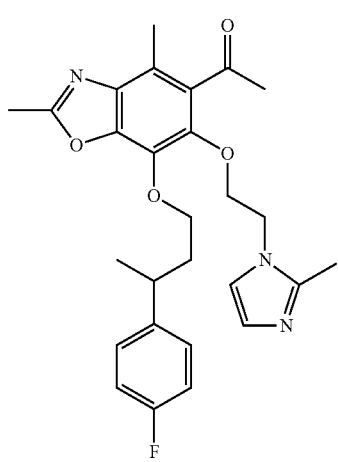

135
-continued
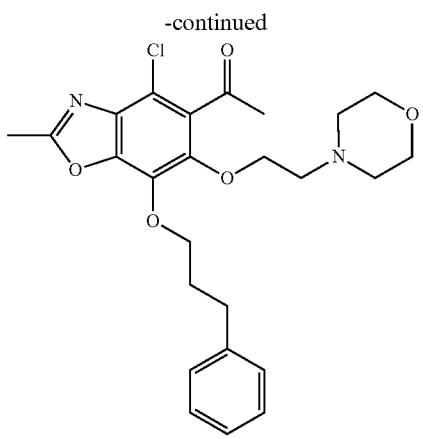
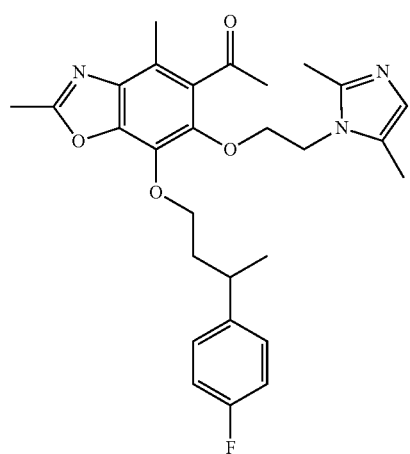
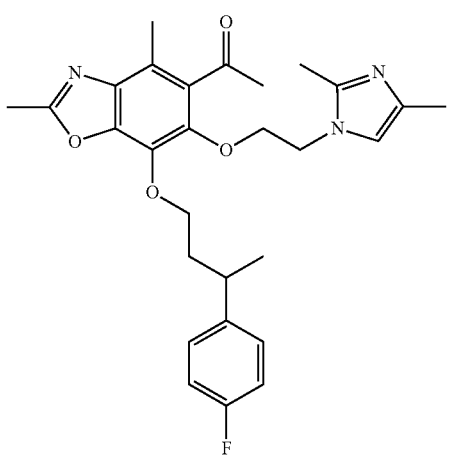
136
-continued
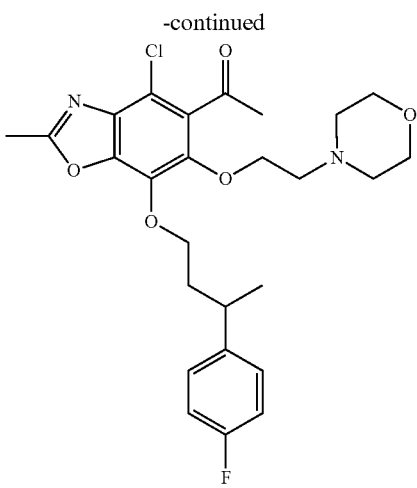
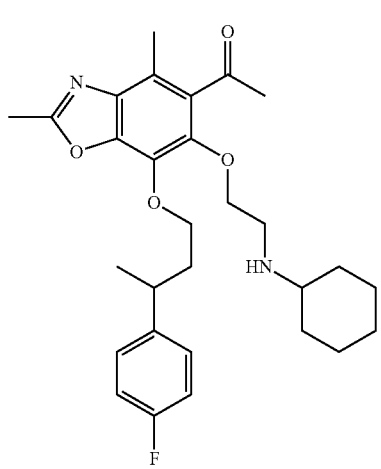
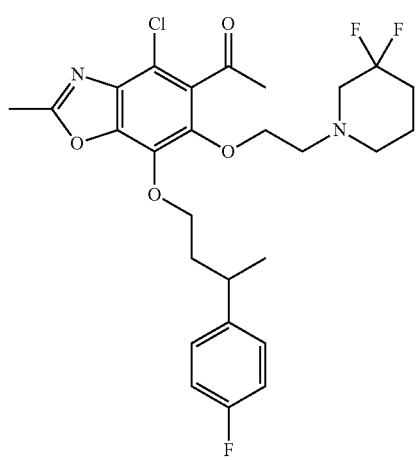

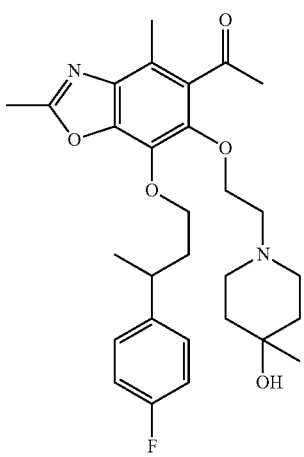

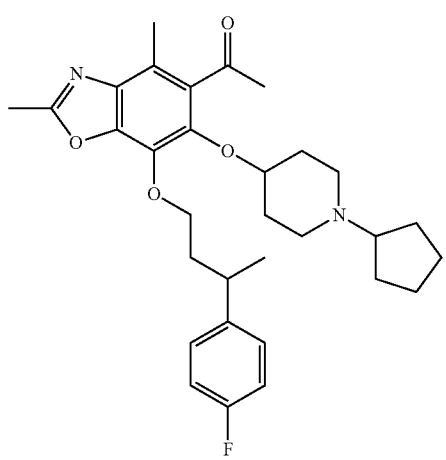

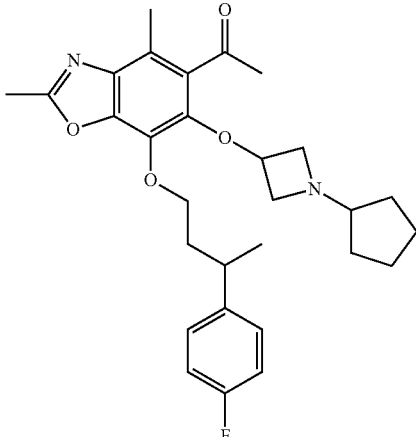

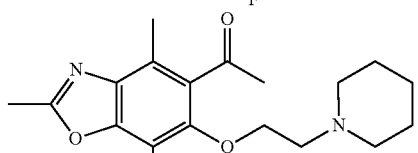

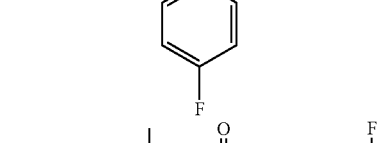

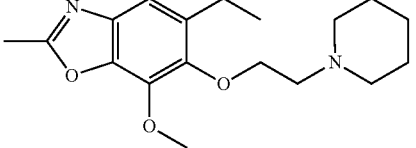

and

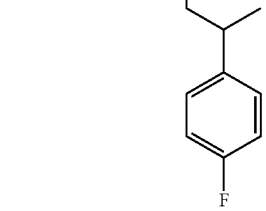

or a salt thereof.

18. A pharmaceutical composition that comprises a therapeutically effective amount of one or more compounds according to claim 1 or pharmaceutically acceptable salts thereof, including pharmaceutically acceptable derivatives thereof, and optionally a pharmaceutically acceptable carrier or diluent.

19. A method of intentionally modulating potassium ion channel activity of T-cells by the application of a compound according to claim 1, or a pharmaceutically acceptable salt thereof, to said T-cells.

20. A compound according to claim 9 or salt thereof, wherein said $C_{3-6}$ cycloalkyl is cyclopropyl.

21. A compound according to claim 9 or salt thereof, wherein said halo $C_{1-3}$ alkyl is $CHF_2$ or $CF_3$.

22. A compound according to claim 10 or salt thereof, wherein said halo is chloro.

* * * * *